(12) United States Patent
Fernandez-Hernando et al.

(10) Patent No.: US 10,053,690 B2
(45) Date of Patent: Aug. 21, 2018

(54) ANTI-MIR-27B AND ANTI-MIR-148A OLIGONUCLEOTIDES AS THERAPEUTIC TOOLS FOR TREATING DYSLIPIDEMIAS AND CARDIOVASCULAR DISEASES

(71) Applicant: New York University, New York, NY (US)

(72) Inventors: Carlos Fernandez-Hernando, Madison, CT (US); Leigh Goedeke, Phoenix, MD (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/898,033

(22) PCT Filed: Jun. 12, 2014

(86) PCT No.: PCT/US2014/042196
§ 371 (c)(1),
(2) Date: Dec. 11, 2015

(87) PCT Pub. No.: WO2014/201301
PCT Pub. Date: Dec. 18, 2014

(65) Prior Publication Data
US 2016/0138018 A1    May 19, 2016

Related U.S. Application Data

(60) Provisional application No. 61/834,389, filed on Jun. 12, 2013.

(51) Int. Cl.
| | | |
|---|---|---|
| *C07H 21/02* | (2006.01) | |
| *C07H 21/04* | (2006.01) | |
| *C12N 15/113* | (2010.01) | |
| *A61K 31/7105* | (2006.01) | |

(52) U.S. Cl.
CPC ........ *C12N 15/113* (2013.01); *A61K 31/7105* (2013.01); *C12N 2310/113* (2013.01); *C12N 2310/141* (2013.01); *C12N 2310/3231* (2013.01); *C12N 2320/31* (2013.01)

(58) Field of Classification Search
CPC .......................... C12N 15/113; C12N 2310/11
See application file for complete search history.

(56) References Cited

U.S. PATENT DOCUMENTS

| | | |
|---|---|---|
| 2005/0261218 A1 | 11/2005 | Esau et al. |
| 2007/0161004 A1 | 7/2007 | Brown et al. |
| 2009/0143326 A1 | 6/2009 | Obad et al. |
| 2011/0190372 A1* | 8/2011 | Tomic-Canic ....... C12N 15/113 514/44 A |
| 2012/0283319 A1 | 11/2012 | Esau et al. |

FOREIGN PATENT DOCUMENTS

WO      2007/112754 A2    10/2007

OTHER PUBLICATIONS

International Search Report and Written Opinion dated Nov. 19, 2014 during prosecution of International Patent Application No. PCT/US2014/042196.
Arora, Amit et al. "Individual mRNA expression profiles reveal the effects of specific microRNAs". Genome Biology (2008), vol. 9, Issue 5, Article R82, pp. 882.1-R82.16.
Barad, Omer et al., "MicroRNA expression detected by oligonucleotide microarrays: System establishment and expression profiling in human tissues", Genome Res. (2004), vol. 14, pp. 2486-2494.
Benjannet, Suzanne et al., "NARC-1/PCSK9 and Its Natural Mutants, Zymogen Cleavage and Effects on the Low Density Lipoprotein (LDL) Receptor and LDL Cholesterol", The Journal of Biological Chemistry (2004), vol. 279, No. 47, pp. 48855-48875.
Bobard, Alexandre et al., "Differential Regulation of Sterol Regulatory Element-binding Protein 1c Transcriptional Activity by Insulin and Liver X Receptor during Liver Development", The Journal of Biological Chemistry (2005), vol. 280, No. 1, pp. 199-206.
Chen, Wu-Jun et al., "The magic and mystery of MicroRNA-27 in atherosclerosis", Elsevier—Atherosclerosis (2012), vol. 222, pp. 314-323.
Do, Ron et al., "Common variants associated with plasma triglycerides and risk for coronary artery disease", Nature Genetics (2013), vol. 45, No. 11, pp. 1345-1353.
Dong, Xue-tao et al., "Expression and Distribution Characteristics of Human Ortholog of Mammalian Enabled (hMena) in Glioma", Chin. J. Cancer Res. (2011), vol. 23, No. 4, pp. 312-316.
Elmen, Joacim et al., "LNA-mediated microRNA silencing in non-human primates", Nature (2008), vol. 452, pp. 896-890.
Ernst, Jason et al., "Discovery and characterization of chromatin states for systematic annotation of the human genome", Nature Biotechnology (2010), vol. 28, No. 8, pp. 817-827.
Esau, Christine et al., "miR-122 regulation of lipid metabolism revealed by in vivo antisense targeting", Cell Metabolism (2006), vol. 3, pp. 87-98.
Gailhouste, Luc et al., "miR-148a Plays a Pivotal Role in the Liver by Promoting the Hepatospecific Phenotype and Suppressing the Invasiveness of Transformed Cells", Hepatology (2013), vol. 58, No. 3, pp. 1153-1165.
Gerstein, Mark B. et al., "Architecture of the human regulatory network derived from ENCODE data", Nature (2012), vol. 489, pp. 91-100.
Horton, Jay D. et al. "SREBPs: activators of the complete program of cholesterol and fatty acid synthesis in the liver", The Journal of Clinical Investigation (2002), vol. 109, No. 09, pp. 1125-1131.

(Continued)

*Primary Examiner* — Amy H Bowman
(74) *Attorney, Agent, or Firm* — Troutman Sanders LLP

(57)                         ABSTRACT

The present invention relates to anti-miR-27b and anti-miR-148a oligonucleotides that are capable of decreasing the level and/or activity of miR-27b and miR-148a, respectively. In conjunction with the oligonucleotide molecules of the present invention, the invention also provides a method for decreasing the level and/or activity of miR-27b and/or miR-148a in a cell. In a further embodiment, the invention provides a method for treating a disease, especially dyslipidemias and cardiovascular diseases.

11 Claims, 22 Drawing Sheets

(56) References Cited

OTHER PUBLICATIONS

Hummel, Richard et al. "Mir-148a Improves Response to Chemotherapy in Sensitive and Resistant Oesophageal Adenocarcinoma and Squamous Cell Carcinoma Cells", J. Gastrointest. Surg. (2011), vol. 15, pp. 429-438.
International Preliminary Report on Patentability issued in International Application No. PCT/US2014/042198 dated Dec. 15, 2015, 7 pages.
Karbiener, Michael et al., "microRNA miR-27b impairs human adipocyte differentiation and targets PPARγ", Biochemical and Biophysical Research Communications 390 (2009), pp. 247-251.
Kim, Sang Yun et al. "miR-27a is a negative regulator of adipocyte differentiation via suppressing PPARγ expression", Biochemical and Biophysical Research Communications 392 (2010), pp. 323-328.
Kim, Jaekwang et al. "miR-106b impairs cholesterol efflux and increases Aβ levels by repressing ABCA1 expression", Experimental Neurology 235 (2012), pp. 476-483.
Krützfeldt, Jan et al., "Silencing of microRNAs in vivo with 'antagomirs'", Nature (2005), vol. 438, pp. 685-689.
Landgraf, Pablo et al., "A Mammalian microRNA Expression Atlas Based on Small RNA Library Sequencing", Cell (2007), vol. 129 pp. 1401-1414.
Lanford, Robert et al., "Therapeutic Silencing of MicroRNA-122 in Primates with Chronic Hepatitis C Virus Infection", Science (2010), vol. 327, pp. 198-201.
Li, Tianrun et al., "Identification of miR-130a, miR-27b and miR-210 as serum biomarkers for atherosclerosis obliterans", Clinica Chimica Acta 412 (2010), pp. 66-70.
Lujambio, Amaia et al., "A microRNA DNA methylation signature for human cancer metastasis", PNAS (2008), vol. 105, No. 36, pp. 13556-13561.
Miura, Shiroh et al., "Anhedonia in Japanese patients with Parkinson's disease: Analysis using the Snaith-Hamilton Pleasure Scale", Clinical Neurology and Neurosurgery 114 (2012), pp. 352-355.
Monteys, Alex Mas et al., "Structure and activity of putative intronic miRNA promoters", RNA (2010), vol. 16, No. 03, pp. 495-505.
Najafi-Shoushtari, Hari S. et al., "MicroRNA-33 and the SREBP Host Genes Cooperate to Control Cholesterol Homeostasis", Science (2010), vol. 328, pp. 1566-1569.
Ramirez. Cristina M. et al., "MicroRNA-758 Regulates Cholesterol Efflux Through Posttranscriptional Repression of ATP-Binding Cassette Transporter A1", Arterioscier Thromb Vasc Biol. (2011), pp. 2707-2714.
Ramirez, Cristina M. et al., "MicroRNA 33 Regulates Glucose Metabolism", Molecular and Cellular Biology (2013), vol. 33, No. 15, pp. 2891-2902.
Rayner, Katey J. et al., "Inhibition of miR-33a/b in non-human primates raises plasma HDL and lowers VLDL triglycerides", Nature (2011), vol. 478, pp. 404-407.
Saini, Harpreet Karr et al., "Genomic analysis of human microRNA transcripts", PNAS (2007), vol. 104, No. 45, pp. 17719-17724.
Shirasaki, Takayoshi et al., "MicroRNA-27a Regulates Lipid Metabolism and Inhibits Hepatitis C Virus Replication in Human Hepatorna Cells", Journal of Virology (2013), vol. 87, No. 09, pp. 5270-5286.
Sjouke, B. et al., "Familial Hypercholesterolemia: Present and Future Management", Curr Cardiol Rep (2011) vol. 13, pp. 527-536.
Staszel, Teresa et al., "Role of microRNAs in endothelial cell pathophysiology", Review Article—Polskie Archiwum Medycyny Wewnetrznej (2011), vol. 121, No. 10, pp. 361-367.
De Agular Vallim, Thomas Q. et al., "Pleiotropic Roles of Bile Adds in Metabolism", Cell Metabolism 17 (2013), pp. 657-669.

Vickers, Kasey C. et al., "MicroRNA-27b is a regulatory hub in lipid metabolism and is altered in dyslipidemia", NIH—Hepatology (2013), vol. 57, No. 02, pp. 533-542.
Wang, Fei et al., "Suturing-Free Artificial Dura with Dacron Heart Patch in Decompressive Craniectomy and Cranioplasty", Indian J. Surg. (2015), vol. 77, Suppl 03, pp. S1008-S1011.
Xu, Qing et al., "A regulatory circuit of miR-148a/152 and DNMT1 in modulating cell transformation and tumor angiogenesis through through IGF-IR and IRS1", Journal of Molecular Cell Biology (2013), vol. 05, pp. 3-13.
Zelcer, Noam et al., "LXR Regulates Cholesterol Uptake Through Idol-Dependent Ubiquitination of the LDL Receptor", Science (2009), vol. 325, pp. 100-104.
Zhang, H. et al., "MiR-148a promotes apoptosis by targeting Bcl-2 in colorectal cancer", Cell Death and Differentiation (2011), vol. 18, pp. 1702-1710.
Zheng, Biqiang et al., "MicroRNA-148a Suppresses Tumor Cell Invasions and Metastasis by Downregulating ROCK1 in Gastric Cancer", Clinical Cancer Research (2011), vol. 17, No. 24, pp. 7574-7583.
Zhou, Chang et al., "microRNA-372 maintains oncogene characteristics by targeting TNFAIP1 and affects NFkB signaling in human gastric carcinoma cells", International Journal of Oncology (2013), vol. 42, pp. 635-642.
Chang, Hua et al., "Increased expression of miR-148b in ovarian carcinoma and its clinical significance", Molecular Medicine Reports (2012), vol. 5, No. 05, pp. 1277-1280.
Yang, Muhua et al., "Identification of miR-185 as a regulator of de novo cholesterol biosynthesis and low density lipoprotein uptake", Journal of Lipid Research (2014), vol. 55, pp. 226-238, doi:10.1194/jlr.M041335.
Yu, Jing et al., "MiR-148a inhibits angiogenesis by targeting ERBB3", Journal of Biomedical Research (2011), vol. 25, No. 03, pp. 170-177.
Fernandez-Hernando, C., "Emerging Role of MicroRNAs in the Regulation of Lipid Metabolism", Hepatology (2013), vol. 57, No. 02, pp. 432-434.
Kida, K. et al., "PPARalpha is regulated by miR-21 and miR-27b in human liver", Pharma Res. (2011), vol. 28, No. 10, pp. 2467-2476.
Communication Pursuant to Rule 164(1) EPC, Partial Supplementary European Search Report Issued in EP14811385.5 dated Jan. 18, 2017, 10 pages.
Extended European Search Report issued in EP14811385.5 dated Apr. 21, 2017, 13 pages.
Goedeke, Leigh et al., "MicroRNA-148a regulates LDL receptor and ABCA1 expression to control circulating lipoprotein levels", Nature Medicine (2015), vol. 21, No. 11, pp. 1280-1289.
Guo, Shui-Long et al., "miR-148a Promoted Cell Proliferation by Targeting p27 in Gastric Cancer Cells", International Journal of Biological Sciences (2011), vol. 7, No. 5, pp. 567-574.
Jin, Lianjin et al., "Prooncogenic Factors miR-23b and miR-27b Are Regulated by Her2/Neu, EGH, and TNF-alpha in Breast Cancer", Cancer Research (2013), vol. 73, No. 9, pp. 2884-2896.
Vickers, Kasey C. et al., "Supplemental Table S1: Annotated Mouse Liver miRNA Signature Annotated Mouse Liver miRNA Signature (Small-RNA-seq)" from "MicroRNA-27b is a Regulatory Hub in Lipid Metabolism and is Altered in Dyslipidemia", Hepatology (2012), vol. 57.
Xu, Xiaojie et al., "Hepatitis B virus X protein represses miRNA-148a to enhance tumorigenesis", The Journal of Clinical Investigation (2013), vol. 123, No. 2, pp. 630-645.
Yuan, Ke et al., "Role of miR-148a in Hepatitis B Associated Hepatocellular Carcinoma", PLOS One (2012), vol. 7, No. 4, p. e35331.
Zhang, Jing et al., "MicroRNA-148a Promotes Myogenic Differentiation by Targeting the ROCK1 Gene", The Journal of Biological Chemistry (2012), vol. 287, No. 25, pp. 21093-21101.

* cited by examiner

Figure 10

A  miR-27b

LDLR

Site 1  Position 2472-2478 of *Ldlr* 3'UTR

```
hsa-miR-27b:      3' ...CGUCUUGAAUCGGUGACACUU... 5'
3'UTR hLDLR:      5' ...GCCUGAAUGUCUUACUGUGAU... 3' hsa    UGUCUU-ACUGUGAUCAA
                  ptr    UGUCUU-ACUGUGAUCAA
                  mmu    UAUCAU-ACUGUGAUGGA
                  rno    UAUCAU-ACUGUGAUGGA
                  ocu    GGGGUC-CCUGUGGUUGA
```

ABCA1

Site 1  Position 2285-2292 of *Abca1* 3'UTR

```
hsa-miR-27b:      3' ...CGUCUUGAAUCGGUGACACUU... 5'
3'UTR hABCA1:     5' ...AAAAUCAAAAGGCACUGUGAA... 3' hsa    AAAAGGCACUGUG-----AA
                  ptr    AAAAGGCACUGUG-----AA
                  mmu    CAAAAGUAAGGC-------A
                  rno    CAAAAAUAAGGC-------A
                  ocu    AAAGGGCACUGUG-----AA
```

Site 2  Position 2593-2600 of *Abca1* 3'UTR

```
hsa-miR-27b:      3' ...CGUCUUGAAUCGGUGACACUU... 5'
3'UTR hABCA1:     5' ...AAACUUAUUAACAACUGUGAA... 3' hsa    ---AACAACUGUGAAUAUG
                  ptr    ---AACAACUGUGAAUAUG
                  mmu    ---A---ACUGUGAAUAUG
                  rno    ---A---ACUGUGAAUAUG
                  ocu    -------ACUGUGAAGAUG
```

LDLRAP1

Site 1  Position 349-355 of *Ldlrap1* 3'UTR

```
hsa-miR-27b:      3' ...CGUCUUGAAUCGGUGACACUU... 5'
3'UTR hLDLRAP1:   5' ...UGUGGGUAUCAGGACUGUGAC... 3' hsa    A-UCAGGACUGUGACCAA
                  ptr    A-UCAGGACUGUGACCAA
                  mmu    G-UCAGGACAAUGACCAA
                  rno    G-UCCAGACAAUGACCAA
                  ocu    GCUCAGGACGGCGACCAA
```

Site 2  Position 1321-1327 of *Ldlrap1* 3'UTR

```
hsa-miR-27b:      3' ...CGUCUUGAAUCGGUGACACUU... 5'
3'UTR hLDLRAP1:   5' ...UCUCUUUGCUGACACUGUGAC... 3' hsa    UGCUGACACUGUGA----
                  ptr    UGCUGACACUGUGA----
                  mmu    UUCUGAC-CUGCAGCCGU
                  rno    UCCUGAC-CUGCAGCCUU
                  ocu    UCCCAGCGCCGUGG----
```

Figure 10

B
miR-148a

LDLR

**Site 1  Position 872-878 of *Ldlr* 3'UTR**

```
hsa-miR-148a:        3' ...UGUUUCAAGACAUCACGUGACU... 5'
3'UTR hLDLR:         5' ...UUGUGUUAUUAUUUGCACUGU... 3' hsa    AUUAUUUUGCACUGUUUU
                     ptr    AUUAUUUUGCACUGUUUU
                     mmu    CCUAGGUUGCACUGACC-
                     rno    CCUAGGUUGCACUGUUUG
                     ocu    ------------------
```

**Site 2  Position 1971-1978 of *Ldlr* 3'UTR**

```
hsa-miR-148a:        3' ...UGUUUCAAGACAUCACGUGACU... 5'
3'UTR hLDLR:         5' ...CCGUGUUACUGU--UGCACUGA... 3' hsa    UUACUGUUGCACUGAUGUC
                     ptr    UUACUGUUGCACUGAUGUC
                     mmu    U----GUCACAUGGGUAAC
                     rno    U----GUCACACGGGUGAC
                     ocu    ------------------
```

ABCA1

**Site 1  Position 3112-3118 of *Abca1* 3'UTR**

```
hsa-miR-148a:        3' ...UGUUUCAAGACAUCACGUGACU... 5'
3'UTR hABCA1:        5' ...AUGGGAUCUAUUUUGCACUGG... 3' hsa    CUAUUUUUGCACUGGAAU
                     ptr    CUAUUUUUGCACUGGAAU
                     mmu    CUAUUUUUGCACUGGAAU
                     rno    CUAUUUUUGCACUGGAAU
                     ocu    CUAUUUUUGCACUGGAAU
```

ANTI-MIR-27B AND ANTI-MIR-148A OLIGONUCLEOTIDES AS THERAPEUTIC TOOLS FOR TREATING DYSLIPIDEMIAS AND CARDIOVASCULAR DISEASES

CROSS-REFERENCE TO RELATED APPLICATIONS

This application is the U.S. National Phase of International Patent Application Serial No. PCT/US2014/042196, filed Jun. 12, 2014, which claims priority to U.S. Provisional Application Ser. No. 61/834,389, filed Jun. 12, 2013, both of which are herein incorporated by reference in their entirety.

STATEMENT REGARDING FEDERALLY SPONSORED RESEARCH

This invention was made with government support under HL107953, HL106063, and AG043318, awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 6, 2014, is named 243735.000144_SL.txt and is 29,706 bytes in size.

FIELD OF THE INVENTION

The present invention relates to anti-miR-27b and anti-miR-148a oligonucleotides and their use as therapeutic tools for treating dyslipidemias and cardiovascular diseases.

BACKGROUND OF THE INVENTION

Cellular and plasma cholesterol levels are maintained through tightly controlled mechanisms, which regulate the expression and activity of key metabolic genes at both the transcriptional and post-transcriptional level. Alterations in the control of cholesterol homeostasis can lead to pathological processes, including atherosclerosis, the most common cause of mortality in Western societies (Lusis 2000, Glass and Witztum 2001). Epidemiological studies have identified many environmental and genetic factors that contribute to atherogenesis. In particular, high levels of low-density lipoprotein (LDL) cholesterol and low levels of high-density lipoprotein (HDL) cholesterol are associated with increased cardiovascular disease (CVD) risk (Lusis 2000, Glass and Witztum 2001). As a result, substantial therapeutic progress has resulted from the widespread use of statins (Gould, Rossouw et al. 1998) and other lipid-lowering drugs aimed at lowering plasma LDL-cholesterol (LDL-C). Despite this, statins are not sufficient to prevent the progression of atherosclerosis in many individuals and there is considerable evidence that quantitatively important determinants of disease susceptibility remain to be identified (Hennekens 1998, Sjouke, Kusters et al. 2011).

In humans, the majority of serum cholesterol is transported as cholesterol esters in LDL particles. To ensure that blood cholesterol levels are balanced, LDL is constantly internalized. The uptake of LDL and other ApoE/ApoB containing lipoproteins occurs through the LDL receptor (LDLR) and is a classic example of receptor-mediated endocytosis (Brown and Goldstein 1976, Brown and Goldstein 1986). The circulating level of LDL is determined in large part by its rate of uptake through this pathway, as evidenced by mutations in Ldlr or ApoB, which lead to the massive accumulation of LDL in patients with familial hypercholesterolemia (FH) (Brown and Goldstein 1974, Maxfield and Tabas 2005). The expression of the LDLR is tightly controlled by feedback mechanisms that operate at both transcriptional and post-transcriptional levels. One of the classical transcriptional regulators of the LDLR is the ER-bound sterol regulatory element-binding protein (SREBP). SREBPs are members of the basic helix-loop-helix leucine zipper (bHLH-Zip) family that bind to sterol response elements (SREs) and promote gene expression (Goldstein and Brown 1990, Brown and Goldstein 1997). In mammals there are three isoforms: SREBP1a and SREBP1c, encoded by the Srebp1 gene, and SREBP2, encoded by the Srebp2 gene. While SREBP1c is regulated by insulin and oxysterols and preferentially enhances the transcription of genes involved in fatty acid synthesis, SREBP2 is regulated by intracellular cholesterol concentrations and is the main regulator of de novo cholesterol biosynthesis (Goldstein and Brown 1990, Brown and Goldstein 1997). When intracellular levels of cholesterol are high, the ER-bound sterol regulatory element-binding proteins (SREBPs), such as SREBP2, coordinate the down-regulation of the LDLR, as well as 3-hydroxy-3methylglutaryl coenzyme A reductase (HMGCR), the rate-limiting enzyme of cholesterol biosynthesis (Goldstein and Brown 1990, Brown and Goldstein 1997). Conversely, when sterol concentrations are low, SREBPs, such as SREBP2, upregulate HMGCR and the LDLR, thereby enhancing LDL clearance from the plasma and ensuring that intracellular cholesterol levels are maintained (Goldstein and Brown 1990, Brown and Goldstein 1997). Additionally, the LDLR is also subject to post-transcriptional regulation such as its proprotein convertase sutilisin/kexin type 9 (PCSK9)-dependent degradation and inducible degrader of idol (IDOL)-dependent ubiquitination (Park, Moon et al. 2004, Zelcer, Hong et al. 2009)

While several key transcriptional regulators of cellular and systemic lipid levels have been identified, post-transcriptional mediators of cholesterol metabolism, including microRNAs, are less well-characterized and just beginning to emerge. MicroRNAs (miRNAs) are short (~22 nt), evolutionary conserved, single-stranded RNAs that control the expression of complementary target mRNAs, leading to their transcript destabilization, translational inhibition, or both (Ambros 2004, Filipowicz, Bhattacharyya et al. 2008, Bartel 2009). As such, they are crucial for the development and maintenance of tissues, both in health and disease states. Recently, it has been suggested that miR-122, miR-33, miR-758, miR-106b, and miR-144 are involved in control of lipid metabolism (Krutzfeldt, Rajewsky et al. 2005, Esau, Davis et al. 2006, Najafi-Shoushtari, Kristo et al. 2010, Ramirez, Davalos et al. 2011, Rayner, Esau et al. 2011, Kim, Yoon et al. 2012, de Aguiar Vallim, Tarling et al. 2013, Ramirez, Rotllan et al. 2013). However, the effect of miR-NAs on LDLR activity has not been described.

miRNAs typically control the expression of their target transcripts by binding to the 3'-UTR of mRNAs. In mammals, the most consistent requirement of miRNA:target interaction, although not always essential, is the contiguous and perfect base pairing of nucleotides 2-8 (the 'seed') at the 5' end of the miRNA (Ambros 2004, Bartel 2004, Filipowicz, Bhattacharyya et al. 2008, Bartel 2009). Given the shortness of the seed region, it is no surprise that a single miRNA can potentially regulate hundreds of genes that are involved in multiple signaling cascades or cellular mechanisms (Bartel 2004). While these numbers emphasize the regulatory potential of miRNAs, they also reflect how difficult it is to determine the function of a given miRNA, as not all predicted targets will contribute to a phenotype. Ascertaining the biological function of miRNAs in regulating a physiological process, therefore, is complex and relies on systematic, unbiased experiments in living cells or organisms.

SUMMARY OF THE INVENTION

As specified in the Background Section, above, there is a great need in the art to develop new therapeutic tools for treating dyslipidemias and cardiovascular diseases. The present invention addresses this and other needs by providing novel antisense oligonucleotides which are specific inhibitors of miR-27b or miR-148a.

In one embodiment, the invention provides an isolated oligonucleotide, wherein said oligonucleotide is capable of decreasing the level and/or activity of miR-27b. In one specific embodiment, miR-27b comprises the sequence 5'-UUCACAGUGGCUAAGUUCUGC-3' (SEQ ID NOS: 1, 58-59). In one specific embodiment, miR-27b consists of the sequence 5'-UUCACAGUGGCUAAGUUCUGC-3' (SEQ ID NOS: 1, 58-59). In another specific embodiment, miR-27b consists of the sequence 5'-ACCUCUC-UAACAAGGUGCAGAGCUUAGCUGAUUG-GUGAACAGUGAUUGGUU UCCGCUUUGUUCACA-GUGGCUAAGUUCUGCACCUGAAGAGAAGGUG-3' (SEQ ID NO: 2).

In one embodiment, the invention provides an isolated oligonucleotide, which oligonucleotide comprises the sequence complimentary to nucleotides 2-8 at the 5' end of the mature miRNA sequence of miR-27b. In one specific embodiment, such mature miRNA sequence of miR-27b is 5'-UUCACAGUGGCUAAGUUCUGC-3' (SEQ ID NOS: 1, 58-59).

In one specific embodiment, said oligonucleotide comprises the sequence 5'-AC(T/U)G(T/U)GA-3' (SEQ ID NO: 114). In another specific embodiment, said oligonucleotide comprises the sequence 5'-ACTGTGA-3' (SEQ ID NO: 115). In yet another specific embodiment, said oligonucleotide comprises the sequence 5'-ACUGUGA-3' (SEQ ID NO: 116). In one specific embodiment, said oligonucleotide ranges from 7 to 40 nucleotides in length. In another specific embodiment, said oligonucleotide ranges from 8 to 21 nucleotides in length. In one specific embodiment, said oligonucleotide is capable of decreasing the level and/or activity of miR-27b.

In one embodiment, the invention provides an isolated oligonucleotide, wherein said oligonucleotide is capable of decreasing the level and/or activity of miR-148a. In one specific embodiment, miR-148a comprises the sequence 5'-UCAGUGCACUACAGAACUUUGU-3' (SEQ ID NOS: 6, 60-61). In one specific embodiment, miR-148a consists of the sequence 5'-UCAGUGCACUACAGAACUUUGU-3' (SEQ ID NOS: 6, 60-61). In another specific embodiment, miR-148a consists of the sequence 5'-GAG-GCAAAGUUCUGAGACACUCCGACUCUGA-GUAUGAUAGAAGUCAGUGCA CUACAGAACUUU-GUCUC-3' (SEQ ID NO: 7).

In one embodiment, the invention provides an isolated oligonucleotide, which oligonucleotide comprises the sequence complimentary to nucleotides 2-8 at the 5' end of the mature miRNA sequence of miR-148a. In one specific embodiment, such mature miRNA sequence of miR-148a is 5'-UCAGUGCACUACAGAACUUUGU-3' (SEQ ID NOS: 6, 60-61). In one specific embodiment, said oligonucleotide comprises the sequence 5'-(T/U)GCAC(T/U)G-3' (SEQ ID NO: 117). In another specific embodiment, said oligonucleotide comprises the sequence 5'-TGCACTG-3' (SEQ ID NO: 118). In yet another specific embodiment, said oligonucleotide comprises the sequence 5'-UGCACUG-3' (SEQ ID NO: 119). In one specific embodiment, said oligonucleotide ranges from 7 to 40 nucleotides in length. In another specific embodiment, said oligonucleotide ranges from 8 to 22 nucleotides in length. In one specific embodiment, said oligonucleotide is capable of decreasing the level and/or activity of miR-148a.

In one embodiment, the oligonucleotide of the invention is a modified oligonucleotide. In one specific embodiment of the invention, the oligonucleotide modification is selected from the group consisting of locked nucleic acids (LNA), 2'-fluoro (2'-F) modified nucleotides, 2'-O-methoxyethyl (2'-MOE) modified nucleotides, 2'-O-methyl (2'O-Me) modified nucleotides, and phosphorothiate (PS) nucleotides.

The invention also provides pharmaceutical compositions comprising one or more oligonucleotides of the invention and a pharmaceutically acceptable carrier or excipient. In one specific embodiment, the composition comprises one or more oligonucleotides targeting miR-27b. In another specific embodiment, the composition comprises one or more oligonucleotides targeting miR-148a. In yet another specific embodiment, the composition comprises (i) one or more oligonucleotides targeting miR-27b and (ii) one or more oligonucleotides targeting miR-148a.

In conjunction with the oligonucleotide molecules of the present invention, the invention also provides a method for decreasing the level and/or activity of miR-27b and/or miR-148a in a cell, which method comprises administering to the cell one or more oligonucleotides of the invention or a composition comprising such one or more oligonucleotide(s). In one specific embodiment, the cell to which the oligonucleotide(s) or composition is administered is a hepatic cell.

In another embodiment, invention provides a method for increasing plasma high-density lipoprotein cholesterol (HDL-C) level and/or reducing plasma low-density lipoprotein cholesterol (LDL-C) level in a subject in need thereof, which method comprises administering to the subject a therapeutically effective amount of one or more oligonucleotides of the invention or a composition comprising such one or more oligonucleotide(s). In a preferred embodiment, the subject is human.

In a further embodiment, the invention provides a method for treating a disease in a subject in need thereof, which method comprises administering to the subject a therapeutically effective amount of one or more oligonucleotides of the invention or a composition comprising such one or more oligonucleotide(s). Non-limiting examples of the diseases treatable by the method of the invention include dyslipidemias (such as, e.g., hyperlipidemia [elevated lipid levels], hypercholesterolemia [elevated cholesterol levels], low HDL/LDL ratio) and cardiovascular diseases (such as, e.g., atherosclerosis, coronary artery disease, coronary heart disease, conditions associated with coronary artery disease or coronary heart disease [e.g., angina, myocardial infarction], transient ischemic attack, stroke). In a preferred embodiment, the subject is human.

In one embodiment of any of the above methods of the invention, the oligonucleotide is a modified or unmodified oligonucleotide selected from the group consisting of 5'-TTCTGTAGTGCACTG-3' (SEQ ID NO: 52; anti-miR-148a), 5'-ACAAAGTTCTGTAGTGCAC-3' (SEQ ID NO:

33; anti-miR-148a), 5'-AACTTAGCCACTGTGA-3' (SEQ ID NO: 54; anti-miR-27b), and 5'-AGAACTTAGCCACT-GTGA-3' (SEQ ID NO: 34; anti-miR-27b). In one specific embodiment, the oligonucleotide is selected from the group consisting of LNA oligonucleotide 5'-TTCTGTAGTG-CACTG-3' (SEQ ID NO: 52; anti-miR-148a), LNA oligonucleotide 5'-AACTTAGCCACTGTGA-3' (SEQ ID NO: 54; anti-miR-27b), miRCURY LNA™ microRNA inhibitor 5'-ACAAAGTTCTGTAGTGCAC-3' (SEQ ID NO: 33; anti-miR-148a), miRCURY LNA™ microRNA inhibitor 5'-AGAACTTAGCCACTGTGA-3' (SEQ ID NO: 34; anti-miR-27b), miRCURY LNA™ microRNA Power inhibitor 5'-ACAAAGTTCTGTAGTGCAC-3' (SEQ ID NO: 33; anti-miR-148a), and miRCURY LNA™ microRNA Power inhibitor 5'-AGAACTTAGCCACTGTGA-3' (SEQ ID NO: 34; anti-miR-27b).

BRIEF DESCRIPTION OF THE DRAWINGS

FIG. 2(A) discloses "miR-23b" as SEQ ID NOS 27 and 62-63 and the corresponding "human," "rhesus" and "mouse" sequences as SEQ ID NOS 28 and 66-67, respectively, "miR-27b" as SEQ ID NOS 1 and 58-59 and the corresponding "human," "rhesus" and "mouse" sequences as SEQ ID NOS 29 and 68-69, respectively, and "miR-24-1" as SEQ ID NOS 31 and 64-65 and the corresponding "human," "rhesus" and "mouse" sequences as SEQ ID NOS 32 and 70-71, respectively. (B) Schematic diagram of human chromosome 7, showing the localization of miR-148a and its conservation among species.

µg/ml DiI-LDL for 8 h at 37° C. Following incubation, cells were washed, fixed, stained and imaged using the Cellomics ArrayScan. Z' factor was calculated based on DiILDL mean average intensity (MAI) in cells transfected with NS siRNA or siLDLR. Representative images are shown in panel (J). DiI-LDL staining is represented by darker grey, and stained nuclei are in darkest grey. In panels (A), (G), and (I) data are the mean±SEM and representative of ≥2 experiments in triplicate. *, P≤0.05 compared to cells transfected with NS siRNA (I). In panels (B) through (D), (E) through (F), and (J) images are representative of ≥3 experiments that gave similar results.

Figure 2:
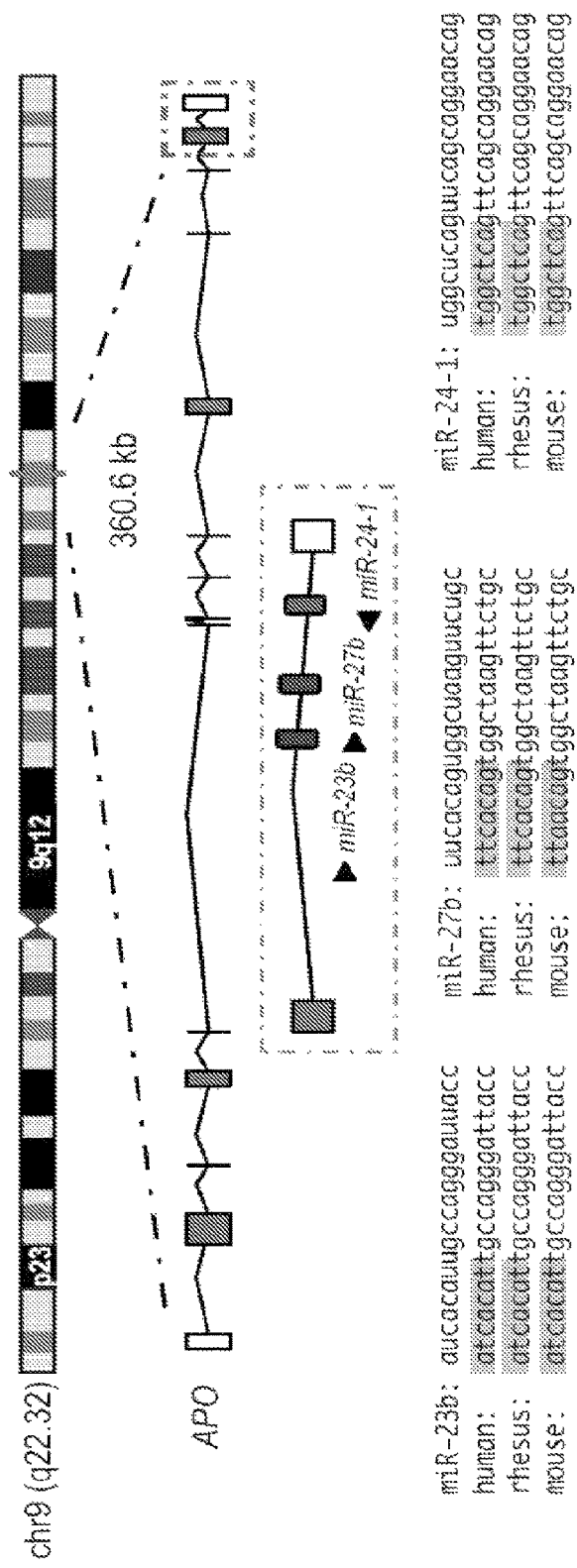
FIGS. 2A-Q. miR-27b and miR-148a are regulated by hepatic lipid content. (A) Schematic diagram of the human APO gene locus, showing the localization of the miR-23b~miR-27b~miR-24-1 cluster and its conservation among species.
FIG. 2(B) discloses "miR-148a" as SEQ ID NOS 6 and 60-61 and the corresponding "human," "rhesus" and "mouse" sequences as SEQ ID NOS 30 and 72-73, respectively. (C-E) qRT-PCR analysis of pri-miR-27b (C), pre-miR-27b (D) and miR-27b (E) in human hepatic cells (Huh7) left untreated (FBS) or loaded with 120 µg/ml native LDL (nLDL) in 10% LPDS. (F-H) qRT-PCR analysis of pri-miR-148a (F), pre-miR-148a (G) and miR-148a (H) in human hepatic cells (Huh7) left untreated (FBS) or loaded with 120 µg/ml nLDL in 10% LPDS. (I-K) qRT-PCR analysis of pri-miR-27b (I), pre-miR-27b (J) and miR-27b (K) in the livers of C57BL/6 mice (n=3 per group) fed a chow or high-fat diet (HFD). (L-N) qRT-PCR analysis of pri-miR-148a (L), pre-miR-148a (M) and miR-148a (N) in the livers of C57BL/6 mice (n=3 per group) fed a chow or high-fat diet (HFD). (O) qRT-PCR analysis of miR-27b in the livers of rhesus monkeys (n=5 per group) fed a chow or high-fat diet (HFD). (P) qRT-PCR analysis of miR-148a in the livers of rhesus monkeys (n=5 per group) fed a chow or high-fat diet (HFD). (Q) qRT-PCR analysis of miR-148a in the livers of wild-type or ob/ob mice (n=3 per group). In panels (C) through (Q), the data are the mean±SEM and representative of ≥3 experiments in duplicate. *, P≤0.05 compared to cells cultured in FBS (C-H). *, P≤0.05 compared to chow diet-fed animals (I-P) or wild-type animals (Q).
Figure 2:
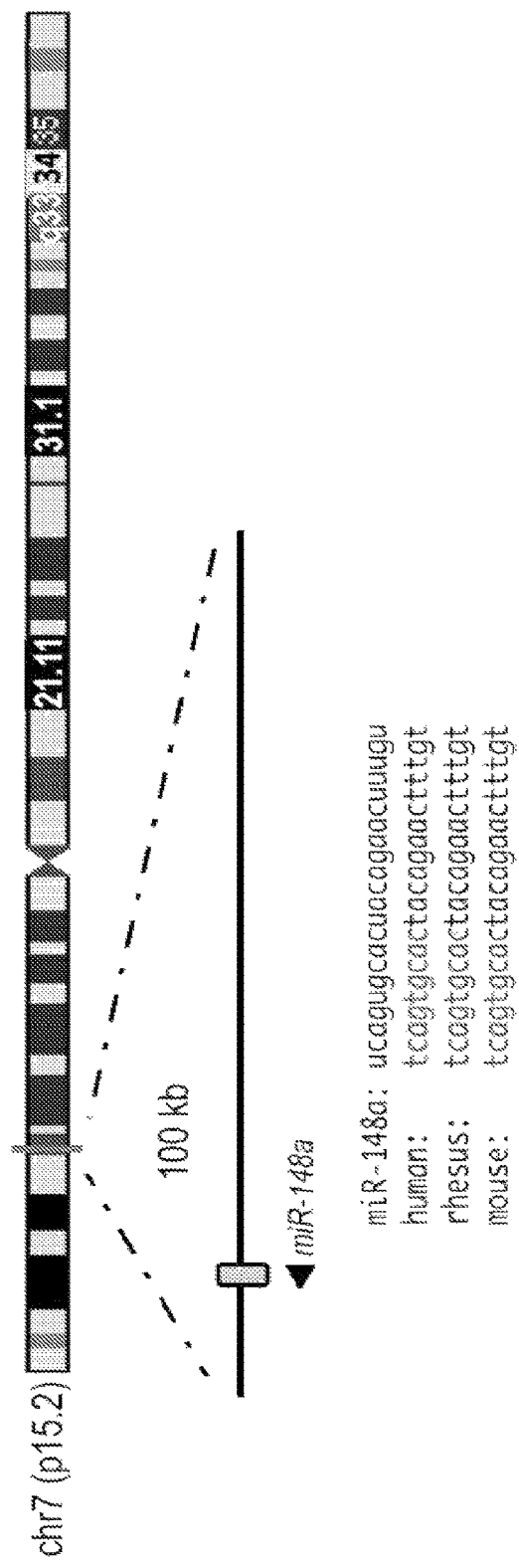
Figure 2:
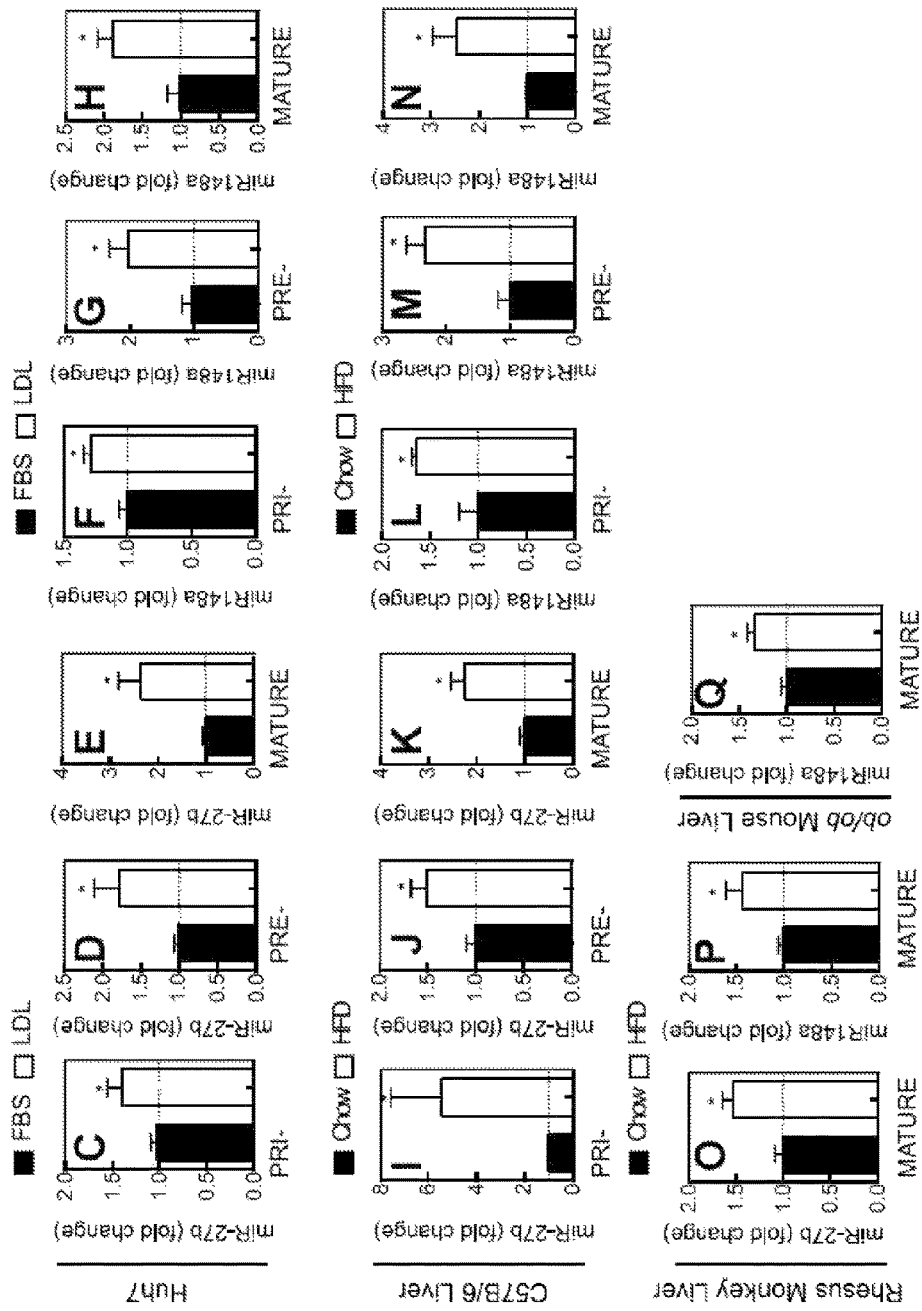
Figure 3:
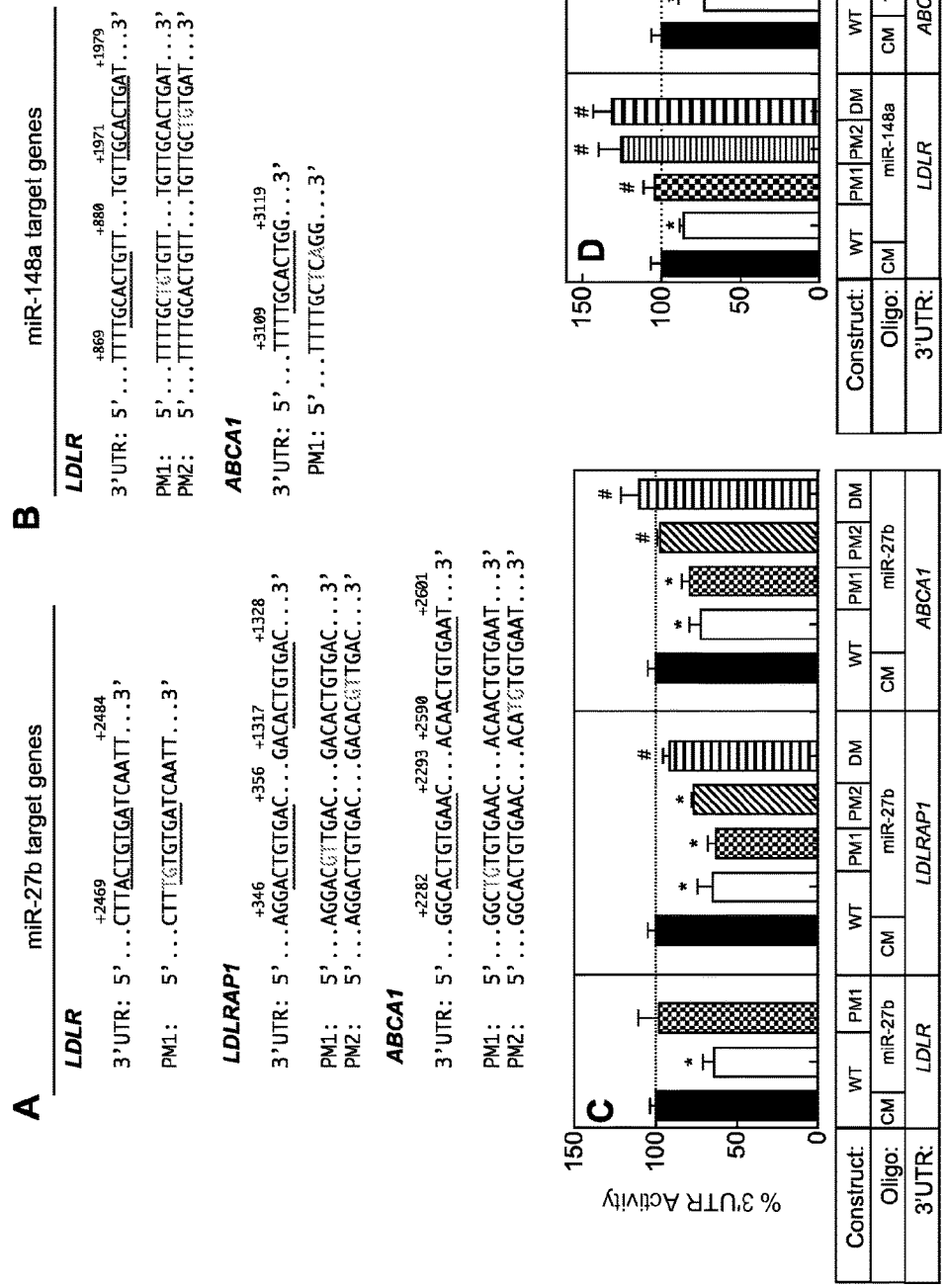
FIG. 3A-D. miR-27b specifically targets the 3'UTR of human LDLR (SEQ ID NOS 35-36, respectively, in order of appearance), LDLRAP1 (SEQ ID NOS 37, 39, 38-39, 37 and 40, respectively, in order of appearance), and ABCA1 (SEQ ID NOS 41, 43, 42-43, 41 and 44, respectively, in order of appearance), while miR-148a specifically targets the 3'UTR of human LDLR (SEQ ID NOS 45, 47, 46-47, 45 and 48, respectively, in order of appearance) and ABCA1 (SEQ ID NOS 49-50, respectively, in order of appearance). (A and B) Human LDLR, LDLRAP1, and ABCA1 3'UTR sequences. Underlined sequences indicate predicted miR-27b binding sites (A) and predicted miR-148a binding sites (B). Nucleotides highlighted in grey indicate respective point mutations (PM) in the miR-27b and miR-148a binding sites. (C) Luciferase reporter activity in COS7 cells transfected with control mimic (CM) or miR-27b mimic (miR-27b) and the human 3'UTR of LDLR, LDLRAP1, and ABCA1 containing the indicated point mutations (PM) in the miR-27b target sites. Double mutation (DM) indicates that two miR-27b binding sites were mutated in the same 3'UTR construct. (D) Luciferase reporter activity in COS7 cells transfected with control mimic (CM) or miR-148a mimic (miR-148a) and the human 3'UTR of LDLR and ABCA1 containing the indicated point mutations (PM) in the miR-148a target sites. Double mutation (DM) indicates that two miR-148a binding sites were mutated in the same 3'UTR construct. In panels (C) and (D), the data are the mean±SEM and representative of ≥2 experiments in triplicate. *, P≤0.05 compared to cells transfected with CM. #, P≤0.05 compared to cells transfected with miR-27b or miR-148a and the control 3'UTR (WT).

FIGS. 9A-B. Bioinformatic analysis of predicted target genes for miR-27b and miR-148a, related to FIGS. 2 and 3. Predicted targets for miR-27b (A) or miR-148a (B) in functional clusters that interact and are enriched in lipid metabolism are shown. Targets for miR-27b or miR-148a that are predicted in Targetscan, miRWalk, and miRanda were uploaded into DAVID for functional annotation cluster analysis. Functional clusters with an enrichment score of ≥1.0 are depicted in diamonds, n represents the number of genes within each cluster, while bracketed numbers represent each cluster number. Grey lines between genes of different clusters indicate STRING interaction score. Genes not found within a functional annotation cluster are indicated by white inverted arrowheads. Predicted gene targets in bold are validated herein.

FIGS. 10A-B. Predicted binding sites for miR-27b and miR-148a in the 3'UTR of LDLR, ABCA1, and LDLRAP1, related to FIG. 3. (A) Location of predicted binding sites for miR-27b in the 3'UTR of LDLR (SEQ ID NOS 1 and 74-79, respectively, in order of appearance), ABCA1 (SEQ ID NOS 1, 80-85, 1 and 86-91, respectively, in order of appearance), and LDLRAP1 (SEQ ID NOS 1, 92-97, 1 and 98-103, respectively, in order of appearance). Site conservation between species is shown below each 3'UTR. (B) Location of predicted binding sites for miR-148a in the 3'UTR of LDLR (SEQ ID NOS 6, 104-108, 6 and 109-113, respectively, in order of appearance) and ABCA1 (SEQ ID NOS 6, 3-5 and 8-10, respectively, in order of appearance). Site conservation between species is shown below each 3'UTR. In panels (A) and (B), site prediction was based on the target prediction algorithm, Targetscan. Seed sequences are in grey font for miR-27b and miR-148a on the 3' to 5' strand of each 3'UTR. Binding sites on the 5' to 3' strand are outlined in grey. Hsa, human; ptr, chimpanzee; mmu, mouse; rno, rat; ocu, rabbit.

Figure 4:
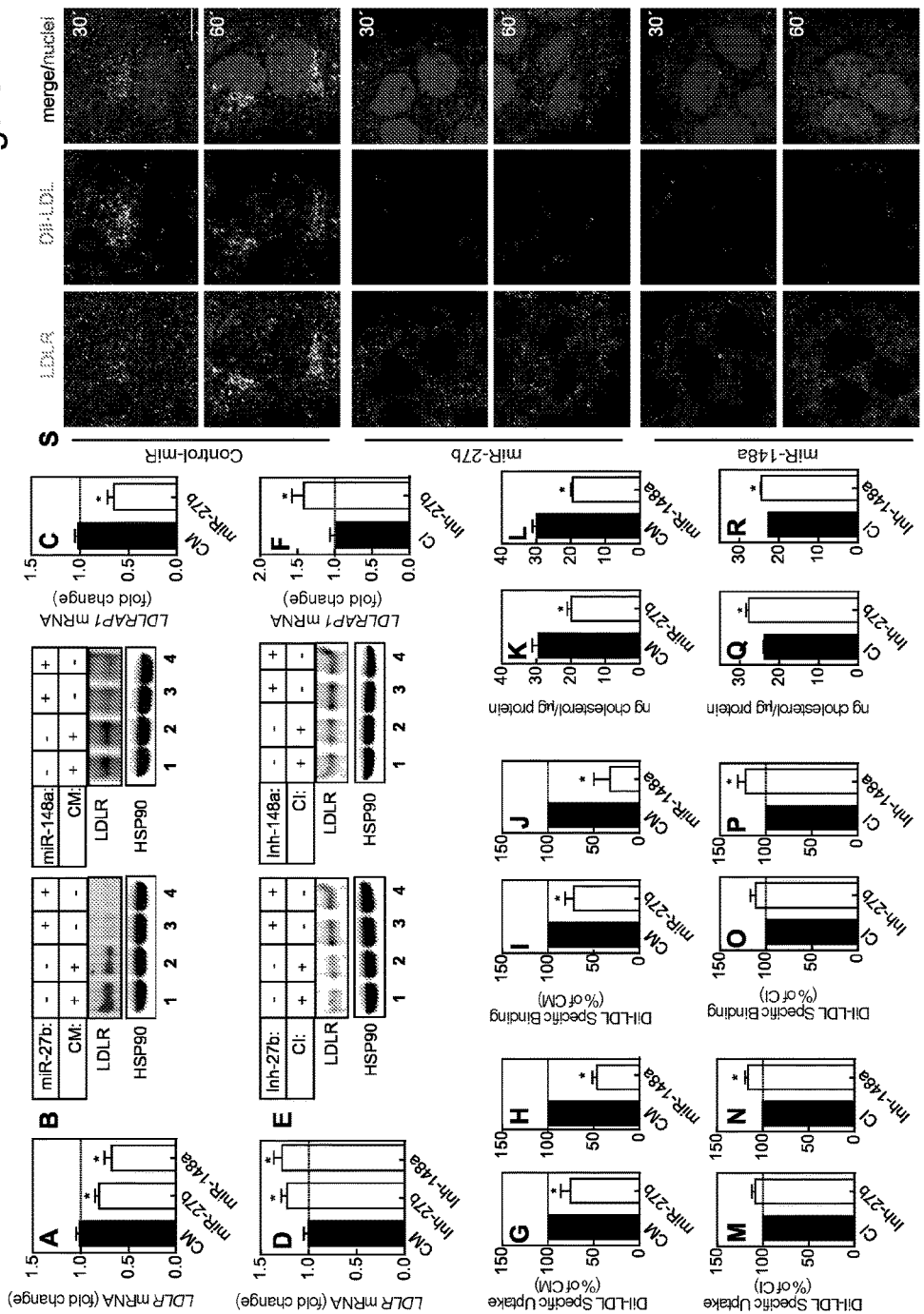
FIGS. 4A-S. Post-transcriptional regulation of LDLR expression and activity by miR-27b and miR-148a in human hepatic cells. (A) qRT-PCR analysis of LDLR in Huh7 cells transfected with a control mimic (CM), miR-27b mimic, or miR-148a mimic. (B) Western blot analysis of LDLR in Huh7 cells transfected with a control mimic (CM), miR-27b mimic (left panel) or miR-148a mimic (right panel). HSP90 was used as a loading control. (C) qRT-PCR analysis of LDLRAP1 in Huh7 cells transfected with a control mimic (CM) or miR-27b mimic. (D) qRT-PCR analysis of LDLR in Huh7 cells transfected with a control inhibitor (CI), miR-27b inhibitor (Inh-27b), or miR-148a inhibitor (Inh-148a). (E) Western blot analysis of LDLR in Huh7 cells transfected with a control inhibitor (CI), miR-27b inhibitor (Inh-27b, left panel) or miR-148a inhibitor (Inh-148a, right panel). HSP90 was used as a loading control. (F) qRT-PCR analysis of LDLRAP1 in Huh7 cells transfected with a control inhibitor (CI) or miR-27b inhibitor (Inh-27b) (G and H) Flow cytometry analysis of DiI-LDL uptake in Huh7 cells transfected with a control mimic (CM), miR-27b mimic (G) or miR-148a mimic (H) and incubated with 3 µg/ml DiI-LDL for 2 h at 37° C. (I and J) Flow cytometry analysis of DiI-LDL binding in Huh7 cells transfected with a control mimic (CM), miR-27b mimic (I) or miR-148a mimic (J) and incubated with 30 µg/ml DiI-LDL for 30 min at 4° C. (K and L) Intracellular cholesterol content in Huh7 cells transfected with a control mimic (CM), miR-27b mime (K), or miR-148a mimic (L) and incubated with 30 μg/ml native LDL (nLDL) for 2 h at 37° C. (M and N) Flow cytometry analysis of DiI-LDL uptake in Huh7 cells transfected with a control inhibitor (CI), inhibitor of miR-27b (Inh-27b, M) or inhibitor of miR-148a (Inh-148a, N) and incubated with 30 μg/ml DiI-LDL for 2 h at 37° C. (O and P) Flow cytometry analysis of DiI-LDL binding in Huh7 cells transfected with a control inhibitor (CI), inhibitor of miR-27b (Inh-27b, O) or inhibitor of miR-148a (Inh-148a, P) and incubated with 30 μg/ml DiI-LDL for 30 min at 4° C. (Q-R) Intracellular cholesterol content in Huh7 cells transfected with a control inhibitor (CI), miR-27b inhibitor (Inh-27b, Q), or miR-148a inhibitor (Inh-148a, R) and incubated with 30 μg/ml native LDL (nLDL) for 2 h at 37° C. (S) LDLR antibody internalization in Huh7 cells transfected with a control mimic (CM, upper panel), miR-27b mimic (middle panel), or miR-148a mimic (lower panel) and incubated with anti-LDLR and 30 μg/ml DiI-LDL for 40 min at 4° C. Following internalization for 30 or 60 min at 37° C., cells were washed, fixed and stained with Alexa Fluor® 488 and TOPRO. Representative confocal images are shown; LDLR staining is represented by light grey, DiI-LDL staining is represented by darker grey, and stained nuclei are in darkest grey. Scale bar, 5 μm. In panels (A) through (R), the data are the mean±SEM and representative of ≥3.

FIGS. 11A-G. miR-27b and miR-148a regulate LDLR expression and activity in mouse hepatic cells, related to FIG. 4. (A and B) qRT-PCR analysis of LDLR in Hepa cells transfected with a control inhibitor (CI), inhibitor of miR-27b (Inh-27b, A) or inhibitor of miR-148a (Inh-148a, B). (C) Western blot analysis of LDLR in Hepa cells transfected with a control inhibitor (CI), inhibitor of miR-27b (Inh-27b, left panel) or inhibitor of miR-148a (Inh-148a, right panel). HSP90 was used as a loading control. (D and E) Flow cytometry analysis of DiI-LDL uptake in Hepa cells transfected with a control inhibitor (CI), inhibitor of miR-27b (Inh-27b, D), or inhibitor of miR-148a (Inh-148a, E) and incubated with 30 µg/ml DiI-LDL for 2 h at 37° C. (F and G) Flow cytometry analysis of DiI-LDL binding in Hepa cells transfected with a (CI), inhibitor of miR-27b (Inh-27b, F), or inhibitor of miR-148a (Inh-148a, G) and incubated with 30 µg/ml DiILDL for 30 min at 4° C. In panels (A) through (G), data are the mean±SEM and representative of ≥2 experiments in triplicate. *, P≤0.05 compared to CI transfected cells (A-B, D-G).

Figure 12:
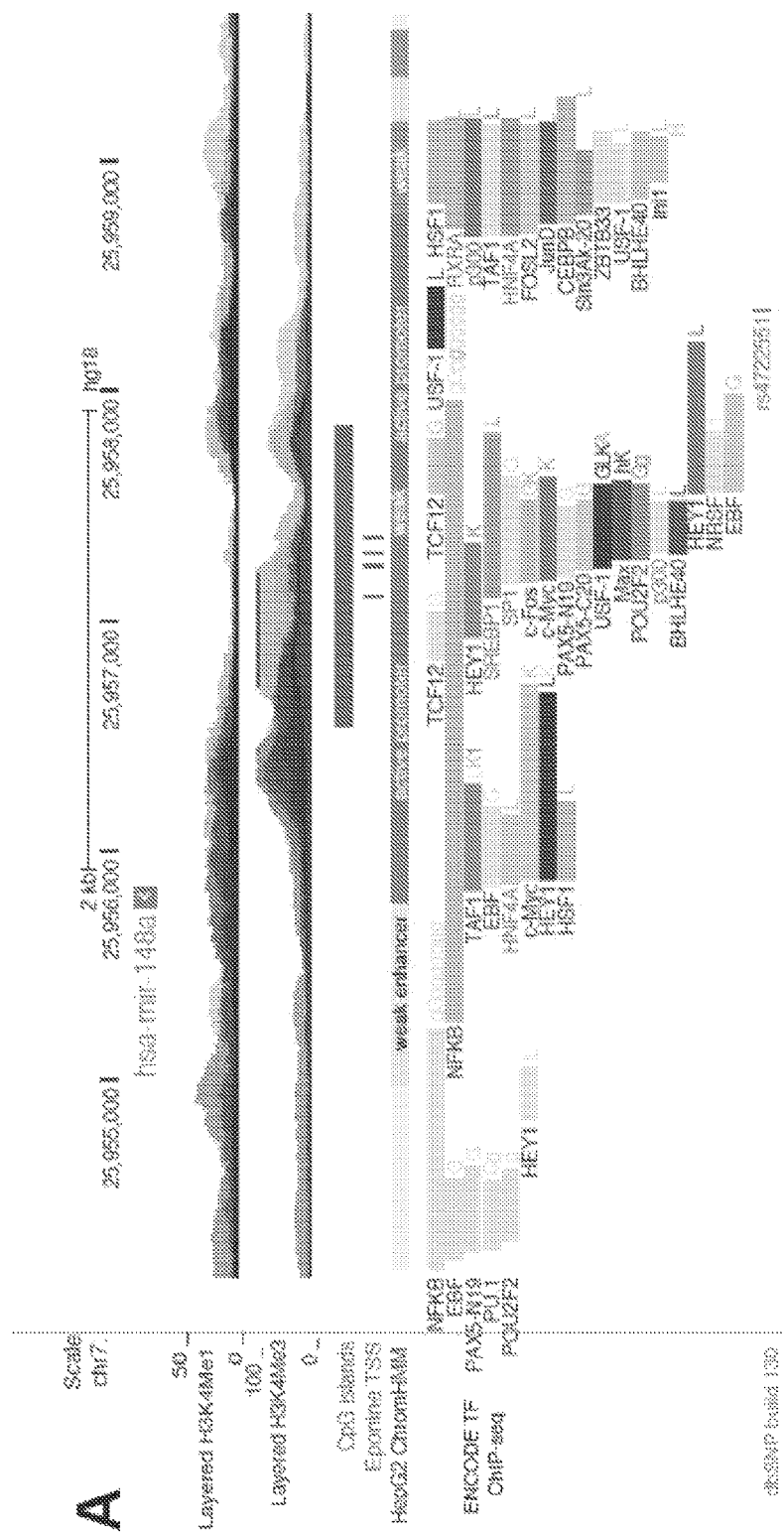
Figure 12:
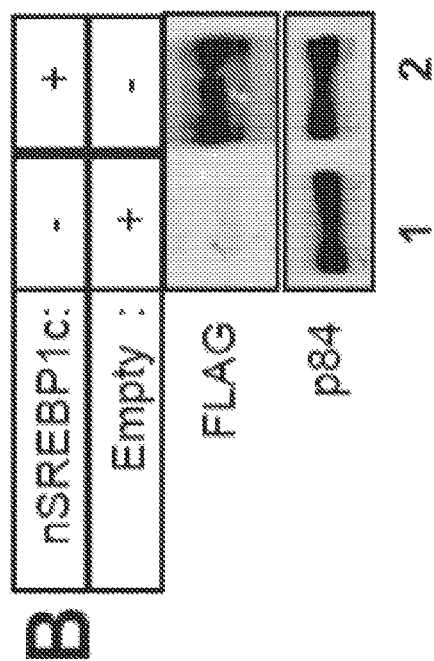
Figure 12:
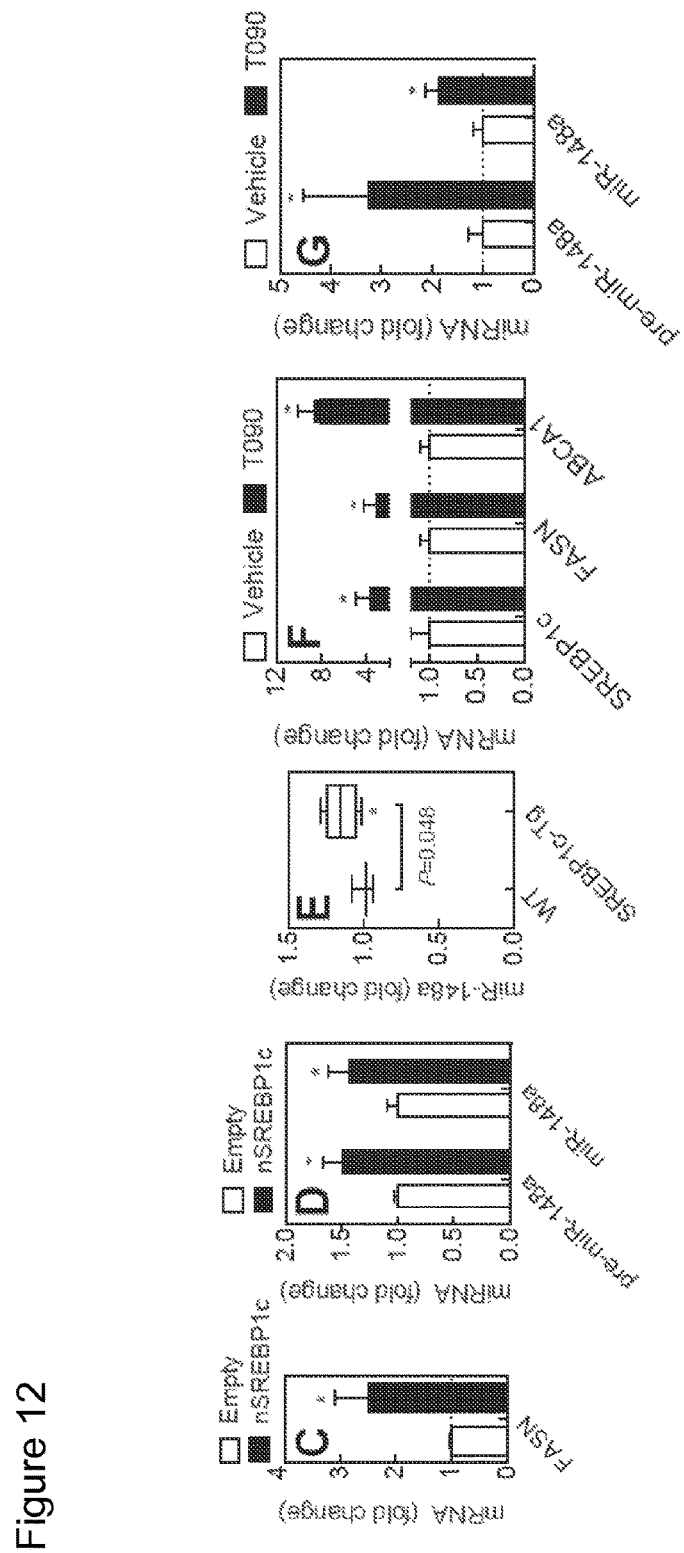
Figure 12:
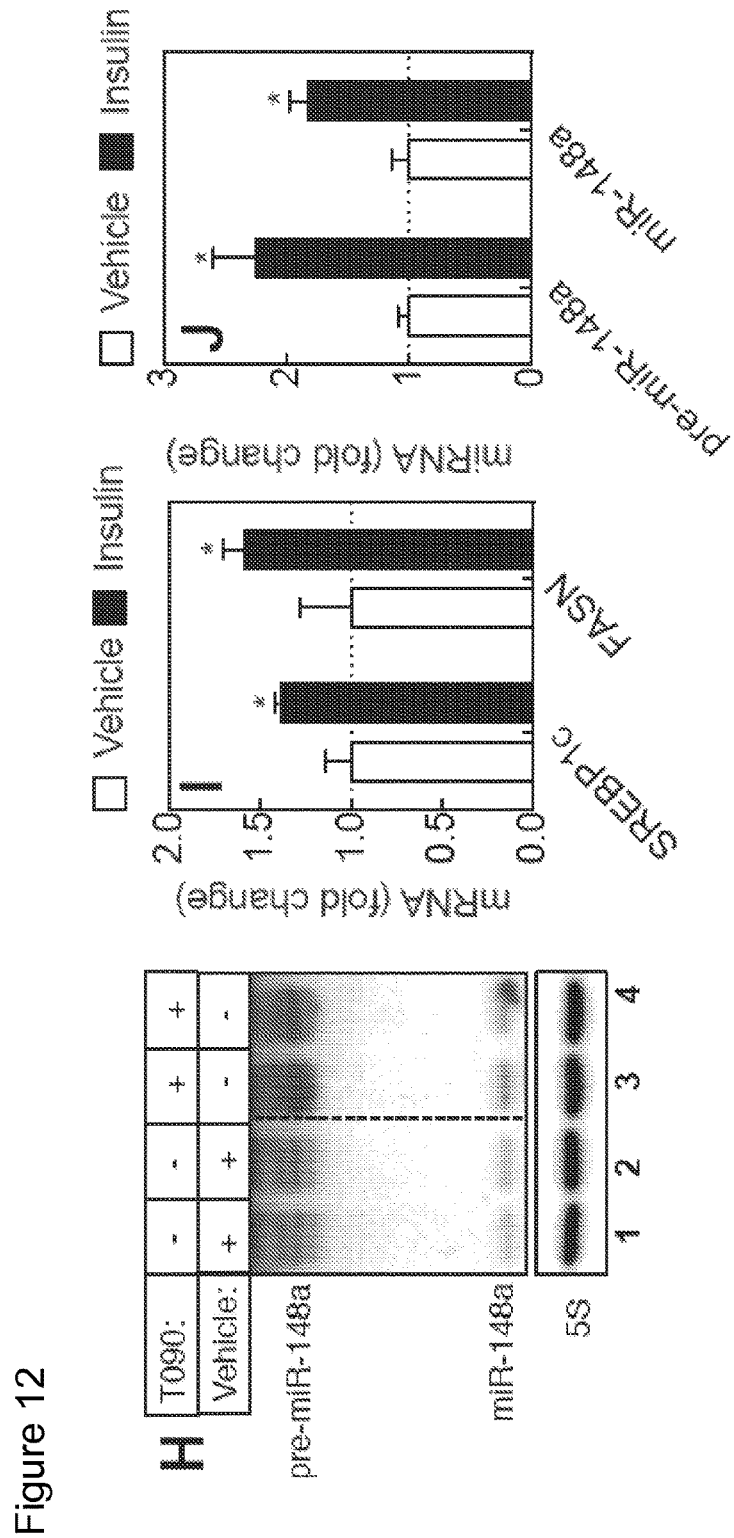
Figure 12:
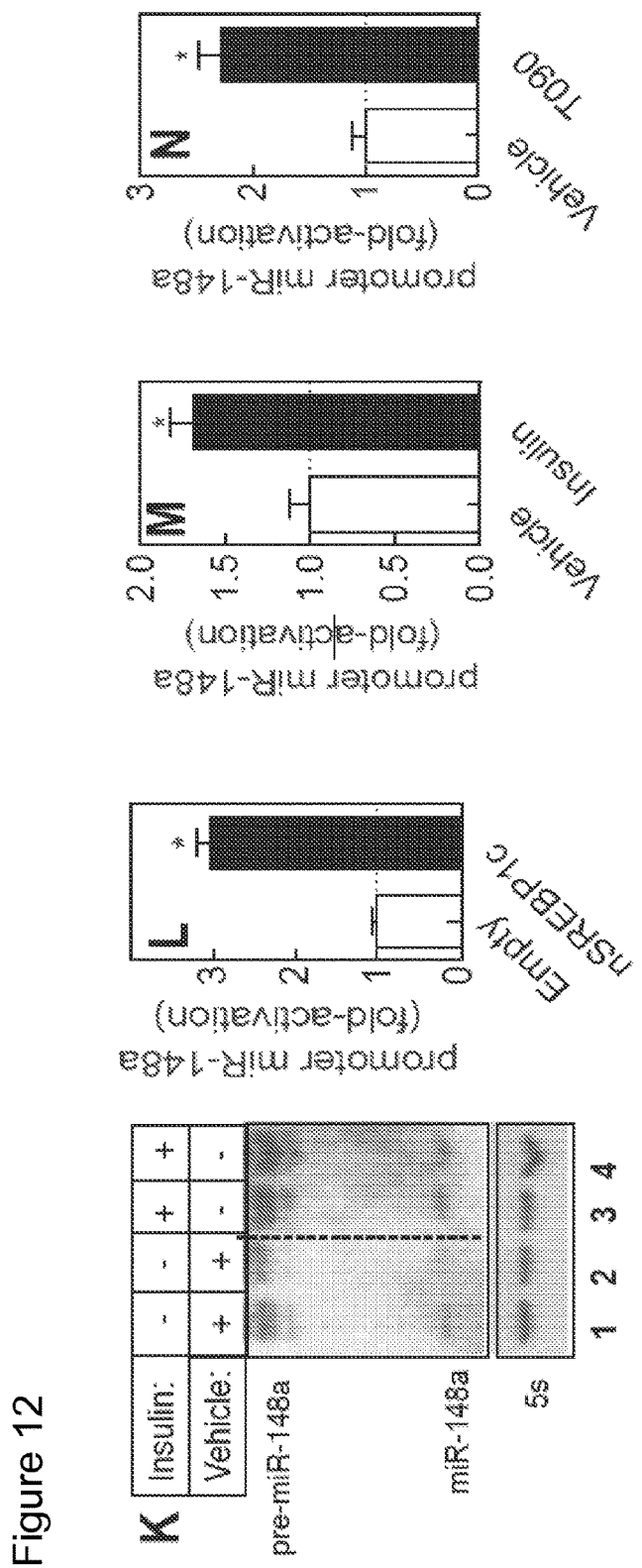

FIGS. 12A-N. Transcriptional regulation of miR-148a by SREBP1c. (A) Schematic diagram of human chromosome 7, showing the localization of miR-148a. The active promoter region of miR-148a is shown (HepG2 ChromHMM) and correlates with CpG islands and enriched H3K4Me3 histone marks. Transcription factor binding sites (as assayed by ChIP-seq) are shown below. Data was compiled using the UCSC Genome Browser (NCBI36/hg18). (B) Western blot analysis of nuclear SREBP1c in Huh7 cells transfected with an empty vector control (Empty) or nuclear SREBP1c-FLAG vector (nSREBP1c). p84 was used as a loading control. (C and D) qRT-PCR analysis of FASN (C), pre-miR-148a (D) and miR-148a (D) in Huh7 cells transfected with an empty vector control (Empty) or nuclear SREBP1c-FLAG vector (nSREBP1c). (E) qRT-PCR analysis of miR-148a in the livers of wild-type (WT) or SREBP1c-Tg mice. n=4 per group. (F through G) qRT-PCR analysis of SREBP1c responsive genes (F) and pre-miR-148a/miR-148a (G) in mouse primary hepatocytes treated with vehicle or T090137 (T090). ABCA1 expression was measured as a positive control for T090 treatment (G). (H) Northern blot analysis of pre-miR-148a (precursor form) and miR-148a (mature form) in mouse primary hepatocytes treated with 3 µM vehicle or T090 for 12 h. 5 s was used as a loading control. (I through J) qRT-PCR analysis of SREBP1c responsive genes (I) and pre-miR-148a/miR-148a (J) in mouse primary hepatocytes treated with vehicle or 30 nM insulin for 6 h. (K) Northern blot analysis of pre-miR-148a (precursor form) and miR-148a (mature form) in mouse primary hepatocytes treated with vehicle or insulin for 6 h. 5 s was used as a loading control. (L) Promoter activity of miR-148a in Hela cells transfected with nuclear SREBP1c (nSREBP1c) or empty vector control. (M-N) Promoter activity of miR-148a in Huh7 cells stimulated with 100 nM insulin (M) or 3 µM T090 (N) for 8 h and 12 h, respectively. In panels (B) through (N), the data are the mean±SEM and representative of ≥2 experiments in triplicate. *, P≤0.05 compared to cells treated with vehicle (F-G, I-J, M-N). *, P≤0.05 compared to cells treated with empty vector (C, D, L), P≤0.05 compared to WT mice (E).

FIGS. 13A-E. Inhibition of miR-148a increases LDLR expression in vivo. (A) Experimental outline of LNA control or LNA anti-miR-148a treated ApoBTg;LDLR$^{-/+}$ mice (n=7 per group). Sequences (SEQ ID NOS 51-53, respectively, in order of appearance) highlighted are complementary to the seed region of mmu-miR-148a (underlined). (B) Northern blot analysis of pre-miR-148a (precursor form) and miR-148a (mature form) in the livers of ApoBTg;LDLR$^{-/+}$ mice after two weeks of treatment with LNA control (LNA CON) or LNA anti-miR-148a (LNA 148a). 5 s was used as a loading control. (C) qRT-PCR analysis of miR-148a levels in the livers of mice following 2 weeks of treatment. *, P≤0.05 compared to LNA control (LNA CON) treated mice. (D) Western blot analysis of LDLR expression in the livers of mice following 2 weeks of treatment. HSP90 was used as a loading control. Quantification of LDLR relative to HSP90 is shown in (E). Numbers are represented as fold-change compared to LNA control (LNA CON) treated mice, *, P≤0.05. (F) Schematic representation of miR-148a-mediated regulation of LDLR. In panels (B) through (E) data are the mean±SEM and representative of each treatment group.

FIGS. 14A-D. Inhibition of miR-27b increases LDLR expression in vivo. (A) Experimental outline of LNA control or LNA anti-miR-27b treated ApoBTg;LDLR$^{-/+}$ mice (n=7 per group). Sequences (SEQ ID NOS 51 and 54-55, respectively, in order of appearance) highlighted are complementary to the seed region of mmu-miR-27b (underlined). (B)

qRT-PCR analysis of miR-27b levels in the livers of mice following 2 weeks of treatment. *, P≤0.05 compared to LNA control (LNA CON) treated mice. (C) Western blot analysis of LDLR expression in the livers of mice following 2 weeks of treatment. HSP90 was used as a loading control. Quantification of LDLR relative to HSP90 is shown in (D). Numbers are represented as fold-change compared to LNA control (LNA CON) treated mice, *, P≤0.05. In panels (B) through (D) data are the mean±SEM and representative of each treatment group.

DETAILED DESCRIPTION OF THE INVENTION

The present invention is based on the identification of miRNAs involved in regulating LDLR activity in a high-throughput microscope-based screening assay that monitored the effect of over 1700 miRNAs on the cellular internalization of fluorescently labeled LDL (DiI-LDL) in human hepatic cells. From this initial screen, the present inventors identified 423 miRNAs that decreased LDLR activity; of these miRNAs, 14 were predicted to target the LDLR and highly expressed in the liver or previously described to be regulated by dietary lipids. Among them, gain and loss-of function experiments established the importance of miR-27b and miR-148a in regulating LDLR activity through direct targeting of the LDLR. In addition, a SREBP1 binding site in the miR-148a promoter region was identified by the inventors; overexpression of nSREBP1c and activation of endogenous SREBP1c by T090 and insulin was shown to increase the promoter activity and expression of miR-148a, thus defining a novel feedback loop for maintaining cholesterol uptake. Furthermore, inhibition of miR-148a with locked nucleic acid (LNA) antisense oligonucleotides significantly increased the expression of LDLR in the livers of mice.

As described in detail in the Examples section below, miR-27b was selected for further characterization and shown to directly target ABCA1 and reduce cellular cholesterol efflux to ApoA1 in human hepatic cells. Importantly, hepatic-specific over expression of miR-27b in mice repressed ABCA1 and LDLR expression in the liver, reducing circulating HDL levels and increasing plasma LDL-C. In addition, inhibition of miR-27b with LNA antisense oligonucleotides significantly upregulated hepatic LDLR expression in mice. Taken together, the data provided herein highlights the role of miRNAs in regulating LDLR activity and demonstrates the therapeutic potential of inhibiting miRNAs to simultaneously contest two of the main risk factors of cardiovascular diseases, namely high levels of LDL-C and low levels of HDL-C.

The present invention provides novel compounds which are specific inhibitors of miR-27b or miR-148a.

Definitions

As used herein, the term "oligonucleotide" refers to a nucleic acid consisting of from 2 to 200 nucleotides, which may be DNA, RNA, a DNA-RNA chimera, or a derivative thereof (see the Oligonucleotide Modifications section, below).

The antisense oligonucleotides of the invention can target both mature miRNAs and miRNA precursors. As used herein, the term "miRNA precursor" is used to encompass, without limitation, primary miRNA transcripts (also known as pri-pre-miRNAs), pri-miRNAs, and pre-miRNAs.

As used herein, the term "complementary sequence," refers to a nucleic acid base sequence that can form a double-stranded structure with another DNA/RNA fragment to which it is complementary, by following base-pairing rules (e.g., A pairs with T/U, and C with G).

Within the meaning of the present invention, the terms "an activity" or "a function" when used in connection with miR-27b or miR-148a are interchangeable and encompasses all possible structural and functional interactions of miR-27b and miR-148a, respectively, including changes in their secondary and/or tertiary structure as well as interactions with various molecules (e.g., nucleic acids, proteins, etc.).

In the context of the present invention insofar as it relates to any of the disease conditions recited herein, the terms "treat", "treatment", and the like mean:
  (1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or
  (2) inhibiting the state, disorder or condition, i.e., arresting, reducing or delaying the development of the disease or a relapse thereof (in case of maintenance treatment) or at least one clinical or sub-clinical symptom thereof; or
  (3) relieving the disease, i.e., causing regression of the state, disorder or condition or at least one of its clinical or sub-clinical symptoms.

As used herein the term "therapeutically effective" applied to dose or amount refers to that quantity of a compound (e.g., oligonucleotide) or pharmaceutical composition that is sufficient to result in a desired activity upon administration to an animal in need thereof. Within the context of the present invention, the term "therapeutically effective" refers to that quantity of a compound or pharmaceutical composition that is sufficient to reduce or eliminate at least one symptom of a disease specified above. Note that when a combination of active ingredients is administered (e.g., anti-miR-27b and anti-miR-148a), the effective amount of the combination may or may not include amounts of each ingredient that would have been effective if administered individually. Therapeutically effective dosages according to the present invention can be determined stepwise by combinations of approaches such as, e.g., (i) characterization in cell cultures using miR-27b and/or miR-148a levels as a readout followed by (ii) characterization in animal studies using plasma high-density lipoprotein cholesterol (HDL-C) and/or low-density lipoprotein cholesterol (LDL-C) levels as a readout, followed by (iii) characterization in human trials using plasma HDL-cholesterol (HDL-C) and/or LDL-cholesterol (LDL-C) levels and/or disease symptoms relief as a readout.

The phrase "pharmaceutically acceptable", as used in connection with the compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to +5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

The term "subject" means any animal, including mammals and, in particular, humans.

As used in this specification and the appended claims, the singular forms "a," "an," and "the" include plural references unless the context clearly dictates otherwise.

In accordance with the present invention, there may be employed conventional molecular biology, microbiology, and recombinant DNA techniques within the skill of the art. See, e.g., Sambrook, Fritsch and Maniatis, Molecular Cloning: A Laboratory Manual, 2nd ed., Cold Spring Harbor Laboratory Press, Cold Spring Harbor, N.Y., 1989 (herein "Sambrook et al., 1989"); DNA Cloning: A Practical Approach, Volumes I and II (Glover ed. 1985); Oligonucleotide Synthesis (Gait ed. 1984); Nucleic Acid Hybridization (Hames and Higgins eds. 1985); Transcription And Translation (Hames and Higgins eds. 1984); Animal Cell Culture (Freshney ed. 1986); Immobilized Cells And Enzymes (IRL Press, 1986); B. Perbal, A Practical Guide To Molecular Cloning (1984); Ausubel et al. eds., Current Protocols in Molecular Biology, John Wiley and Sons, Inc. 1994; among others.

Antisense Oligonucleotides of the Invention

The antisense oligonucleotides of the invention encompass all antisense oligonucleotides which are capable of inhibiting expression and/or function of miR-27b or miR-148a. To successfully inhibit expression and/or function of miR-27b or miR-148a, such antisense oligonucleotides need to be complementary to at least the 'seed region' of the target mature miRNA sequence (nt 2-8 at the 5' end of the mature miRNA sequence). Perfect complementarity is not required for other parts of the antisense oligonucleotide and can be, for example, at least about 75%, 80%, 85%, 90%, 95%, 96%, 97%, 98%, or 99% complementary to a target miRNA sequence.

```
Sequences for hsa-miR-27b-3p
Mature: MIMAT0000419
                                         (SEQ ID NO: 1)
5'-UUCACAGUGGCUAAGUUCUGC-3'

Precursor: MI0000440
                                         (SEQ ID NO: 2)
5'-ACCUCUCUAACAAGGUGCAGAGCUUAGCUGAUUGGUGAACAGU
GAUUGGUUUCCGCUUUGUUCACAGUGGCUAAGUUCUGCACCUGAAG
AGAAGGUG-3'

Sequences for hsa-miR-148a-3p
Mature: MIMAT0000243
                                         (SEQ ID NO: 6)
5'-UCAGUGCACUACAGAACUUUGU-3'

Precursor: MI0000253
                                         (SEQ ID NO: 7)
5'-GAGGCAAAGUUCUGAGACACUCCGACUCUGAGUAUGAUAGAAGU
CAGUGCACUACAGAACUUUGUCUC-3'
```

The antisense oligonucleotides of the present invention include ribonucleotides or deoxyribonucleotides or combinations thereof. The antisense oligonucleotides of the present invention include various oligonucleotide analogs and derivatives, which analogs and derivatives are also capable of inhibiting expression and/or function of miR-27b or miR-148a. Such analogs and derivatives may have increased in vivo stability, particularly nuclease resistance, and/or reduced non-specific binding, and/or increased bioavailability as compared to unmodified oligonucleotides. The oligonucleotides may be modified at the backbone, the sugar moiety, or the bases themselves.

For instance, suitable antisense oligonucleotides may be comprised of one or more "conformationally constrained" or bicyclic sugar nucleoside modifications (BSN) that confer enhanced thermal stability to complexes formed between the oligonucleotide containing BSN and their complementary miRNA target strand. For example, in one embodiment, the antisense oligonucleotides contain at least one "locked nucleic acid." Locked nucleic acids (LNAs) contain the 2'-O, 4'-C-methylene ribonucleoside wherein the ribose sugar moiety is in a "locked" conformation. In another embodiment, the antisense oligonucleotides contain at least one 2',4'-C-bridged 2' deoxyribonucleoside (CDNA). See, e.g., U.S. Pat. No. 6,403,566 and Wang et al. (1999) Bioorganic and Medicinal Chemistry Letters, Vol. 9: 1147-1150. The antisense oligonucleotides of the invention can also contain combinations of BSN (LNA, CDNA and the like) or other modified nucleotides, and ribonucleotides or deoxyribonucleotides. The antisense oligonucleotides of the invention can comprise peptide nucleic acids (PNAs), which contain a peptide-based backbone rather than a sugar-phosphate backbone. Other modified sugar or phosphodiester modifications to the antisense oligonucleotide are also contemplated. Non-limiting examples of other chemical modifications that the antisense oligonucleotides of the invention can contain include sugar modifications, such as 2'-O-alkyl (e.g., 2'-O-methyl, 2'-O-methoxyethyl), 2'-fluoro, and 4'-thio modifications, and backbone modifications, such as one or more phosphorothioate, morpholino, or phosphonocarboxylate linkages (see, for example, U.S. Pat. Nos. 6,693,187 and 7,067,641). In some embodiments, suitable antisense oligonucleotides are 2'-O-methoxyethyl "gapmers" which contain 2'-O-methoxyethyl-modified ribonucleotides on both 5' and 3' ends with at least ten deoxyribonucleotides in the center. These "gapmers" are capable of triggering RNase H-dependent degradation mechanisms of RNA targets.

Examples of oligonucleotide backbone modifications include, without limitation, oligonucleotides that contain phosphorus group in the backbone, phosphorothioates, chiral phosphorothioates, phosphorodithioates, phosphotriesters, aminoalkylphosphotriesters, methyl and other alkyl phosphonates comprising 3'alkylene phosphonates and chiral phosphonates as well as short chain alkyl, or cycloalkyl intersugar linkages or short chain heteroatomic or heterocyclic intersugar linkages, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. Specific examples include, among others, oligonucleotides with CH$_2$—NH—O—CH$_2$, CH$_2$—N(CH$_3$)—O—CH$_2$, CH$_2$—O—N(CH$_3$)—CH$_2$, CH$_2$—N(CH$_3$)—N(CH$_3$)—CH$_2$ and O—N(CH$_3$)—CH$_2$—CH$_2$ backbones (where phosphodiester is O—PO$_2$—O—CH$_2$).

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. U.S. Pat. No. 5,034,506 describes oligonucleotides having morpholino backbone structures. U.S. Pat. No. 5,677,437 describes heteroaromatic oligonucleoside linkages. U.S. Pat. Nos. 5,792,844 and 5,783,682 describe nitrogen linkers or groups containing nitrogen. U.S. Pat. No. 5,637,684 describes phosphoramidate and phosphorothioamidate oligomeric compounds. Further examples include oligonucleotides with phosphorothioate backbones and oligonucleosides with heteroatom backbones, and in particular-CH$_2$—NH—O—CH$_2$—, —CH$_2$—N(CH$_3$)—O—CH$_2$-known as a methylene (methylimino) or MMI backbone, —CH—O—N(CH$_3$)—CH$_2$—, —CH$_2$N(CH$_3$)—N(CH$_3$) CH$_2$— and —O—N(CH$_3$)—CH$_2$—CH$_2$— wherein the native phosphodiester backbone is represented as —O—P—O—CH$_2$—. See, e.g., U.S. Pat. Nos. 5,489,677 and 5,602,240.

In other oligonucleotide modifications encompassed by the present invention, both the sugar and the internucleoside linkage, i.e., the backbone, of the nucleotide units are replaced with novel groups. Example of such modification is a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. See, e.g., Nielsen et al., Science 1991; 254:1497.

Modified oligonucleotides encompassed by the present invention may also contain one or more substituted sugar moieties. Examples include oligonucleotides containing substituted sugar moieties comprising one of the following at the 2' position: OH, SH, SCH$_3$, F, OCN, O(CH$_2$)$_n$O$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_{2n}$ON(CH$_2$)$_n$CH$_3$)$_2$ where n and m can be from 1 to about 10; C$_1$ to C$_{10}$ lower alkyl, substituted lower alkyl, alkaryl or aralkyl; O-alkaryl or O-aralkyl; Cl; Br; CN; CF$_3$; OCF$_3$; O-; S- or N-alkyl; O-, S-, or N-alkenyl; O-, S- or N-alkynyl; or O alkyl-O-alkyl, wherein the alkyl, alkenyl and alkynyl may be substituted or unsubstituted C to C$_0$ alkyl or C$_2$ to C$_0$ alkenyl and alkynyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted sialyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. See, e.g., Martin et al., Helv. Chim. Acta, 1995, 78, 486-504 which describes a modification comprising 2'-methoxyethoxy (2'-O—CH$_2$CH$_2$OCH$_3$, also known as 2'-O-(2-methoxyethyl) or 2'-MOE), i.e., an alkoxyalkoxy group. Another specific modification comprises 2'-dimethylaminooxyethoxy, i.e., a O(CH$_2$)$_2$ON(CH$_3$)$_2$ group, also known as 2'-DMAOE, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$. Other preferred modifications comprise 2'-methoxy (2'-O CH$_3$), 2'-aminopropoxy (2'-O CH$_2$CH$_2$CH$_2$NH$_2$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls or other carbocyclics in place of the pentofuranosyl group.

Oligonucleotides of the invention may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases other synthetic and natural nucleobases such as xanthine, hypoxanthine, 6-methyl and other alkyl derivatives of adenine and guanine, 2-propyl and other alkyl derivatives of adenine and guanine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 2-thiocytosine, 5-halouracil and cytosine (e.g., 5-bromouracil), 5-hydroxymethyluracil, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine, N$_6$ (6-aminohexyl)adenine and 2,6-diaminopurine. A "universal" base known in the art, e.g., inosine, may be also included. See, e.g., Kornberg, A., DNA Replication, W. H. Freeman & Co., San Francisco, 1980, pp 75-77; Gebeyehu, G., et al. Nucl. Acids Res. 1987, 15:4513). Further modified nucleobases comprise those disclosed in U.S. Pat. No. 3,687,808, those disclosed in "The Concise Encyclopaedia of Polymer Science And Engineering", pages 858-859, Kroschwitz, J. I., ed. John Wiley & Sons, 1990, those disclosed by Englisch et al., "Angewandle Chemie, International Edition", 1991, 30, page 613, and those disclosed by Sanghvi, Y. S., Crooke, S. T. and Lebleu, B., eds, "Antisense Research and Applications", CRC Press, Boca Raton, 1993, pp. 276-302 and Crooke, S. T. and Lebleu, B. ea., CRC Press, 1993.

A further class of oligonucleotide modifications used in the present invention is referred to as cyclohexenyl nucleic acids (CeNA). The furanose ring normally present in a DNA or RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.,* 2000, 122, 8595-8602).

In other embodiments, locked nucleic acids (LNA) can be used (reviewed in, e.g., Jepsen and Wengel, Curr. Opin. Drug Discov. Devel. 2004; 7:188-194; Crinelli et al., Curr. Drug Targets 2004; 5:745-752). LNA are nucleic acid analog(s) in which the 2'-hydroxyl group of the ribosyl sugar ring is linked to the 4' carbon atom of the sugar ring thereby forming a 2'-O,4'-C-oxymethylene linkage to form the bicyclic sugar moiety (reviewed in Elayadi et al., *Curr. Opinion Invens. Drugs,* 2001, 2, 558-561; Braasch et al., *Chem. Biol.,* 2001, 8 1-7; and Orum et al., *Curr. Opinion Mol. Ther.,* 2001, 3, 239-243; see also U.S. Pat. Nos. 6,268,490 and 6,670,461). This bridge restricts the flexibility of the ribofuranose ring and locks the structure into a rigid C3-endo conformation, conferring enhanced hybridization performance and exceptional biostability (see, e.g., Uhlman, Current Opinions in Drug Discovery & Development 2000, Vol. 3 No. 2; Frieden et al., Nucleic Acids Research, 2003, 21, 6365-6372; Wahlestedt et al., Proc. Natl. Acad. Sci. U.S.A., 2000, 97, 5633-5638). The linkage can be a methylene (—CH$_2$—) group bridging the 2' oxygen atom and the 4' carbon atom, for which the term LNA is used for the bicyclic moiety; in the case of an ethylene group in this position, the term ENA is used (Singh et al., Chem. Commun., 1998, 4, 455-456; ENA™: Morita et al., Bioorganic Medicinal Chemistry, 2003, 11, 2211-2226). Another similar bicyclic sugar moiety that has been prepared and studied has the bridge going from the 3'-hydroxyl group via a single methylene group to the 4' carbon atom of the sugar ring thereby forming a 3'-C,4'-C-oxymethylene linkage (see U.S. Pat. No. 6,043,060). LNA and other bicyclic sugar analogs display very high duplex thermal stabilities with complementary DNA and RNA (Tm=+3 to +10° C.), stability towards 3'-exonucleolytic degradation and good solubility properties. LNAs are commercially available from, e.g., ProLigo (Paris, France and Boulder, Colo., USA).

Another oligonucleotide modification encompassed by the present invention is threose nucleic acid (TNA) which contains threose nucleosides instead of ribose nucleosides. See, e.g., Chaput et al., J. Am. Chem. Soc., 2003, 125, 856-857; Wu et al., Organic Letters, 2002, 4(8), 1279-1282.

Further oligonucleotide mimetics have been prepared to include bicyclic and tricyclic nucleoside analogs (see Steffens et al., *Helv. Chim. Acta,* 1997, 80, 2426-2439; Steffens et al., *J. Am. Chem. Soc.,* 1999, 121, 3249-3255; Renneberg et al., *J. Am. Chem. Soc.,* 2002, 124, 5993-6002; and Renneberg et al., *Nucleic Acids Res.,* 2002, 30, 2751-2757). These modified nucleoside analogs have been oligomerized using the phosphoramidite approach and the resulting oligomeric compounds containing tricyclic nucleoside analogs have shown increased thermal stabilities (Tms) when hybridized to DNA, RNA and itself.

Another modification of the oligonucleotides of the invention involves chemically linking to the oligonucleotide one or more heterologous moieties which enhance the activity or cellular uptake of the oligonucleotide. Such heterologous moieties include but are not limited to lipid moieties such as a cholesterol moiety, a cholesteryl moiety (Letsinger et al., Proc. Natl. Acad. Sci. USA 1989, 86, 6553), cholic acid (Manoharan et al. Bioorg. Med. Chem. Let. 1994, 4, 1053), a thioether, e.g., hexyl-S-tritylthiol (Manoharan et al. Ann. N.Y. Acad. Sci. 1992, 660, 306; Manoharan et al. Bioorg. Med. Chem. Let. 1993, 3, 2765), a thiocholesterol (Oberhauser et al., Nucl. Acids Res. 1992, 20, 533), an aliphatic chain, e.g., dodecandiol or undecyl residues (Saison-Behmoaras et al. EMBO J. 1991, 10, 111; Kabanov et al. FEBS Lett. 1990, 259, 327; Svinarchuk et al. Biochimie 1993, 75, 49), a phospholipid, e.g., di-hexadecyl-rac-glycerol or triethylammonium 1,2-di-O-hexadecyl-rac-glycero-3-H-phosphonate (Manoharan et al. Tetrahedron Lett. 1995, 36, 3651; Shea et al. Nucl. Acids Res. 1990, 18, 3777), a polyamine or a polyethylene glycol chain (Manoharan et al. Nucleosides & Nucleotides 1995, 14, 969), or adamantane acetic acid (Manoharan et al. Tetrahedron Lett. 1995, 36, 3651), a palmityl moiety (Mishra et al., Biochim. Biophys. Acta, 1995, 1264, 229-237), or an octadecylamine or hexylaminocarbonyl-t oxycholesterol moiety (Crooke et al., J. Pharmacol. Exp. Ther., 1996, 277, 923-937). Oligonucleotides comprising lipophilic moieties, and methods for preparing such oligonucleotides are known in the art, for example, from U.S. Pat. Nos. 5,138,045, 5,218,105 and 5,459,255. Other covalently linked moieties may include, for example, proteins, intercalators, chelators, or alkylators. The oligonucleotides herein may also be modified with a label capable of providing a detectable signal, either directly or indirectly. Exemplary labels include radioisotopes, fluorescent molecules, biotin, and the like.

Examples of modified phosphate groups which can be used in antisense oligonucleotides of the invention include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by replacement of a linking oxygen with nitrogen (bridged phosphoroamidates), sulfur (bridged phosphorothioates) and carbon (bridged methylenephosphonates). The replacement can occur at a terminal oxygen. The phosphate group can be replaced by non-phosphorus containing connectors. Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

The antisense oligonucleotides of the invention can include a 2'-deoxy, 2'-deoxy-2'-fluoro, 2'-β-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). The 3' and 5' ends of an antisense oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester).

The sugar group can also contain one or more carbons that possess the opposite stereochemical configuration than that of the corresponding carbon in ribose. Thus, a modified RNA can include nucleotides containing e.g., arabinose, as the sugar. Modified RNAs can also include "abasic" sugars, which lack a nucleobase at C-1'. These abasic sugars can also further contain modifications at one or more of the constituent sugar atoms. The modification can also entail the wholesale replacement of a ribose structure with another entity (an SRMS) at one or more sites in the oligonucleotide agent.

Terminal modifications can include the addition of a methylphosphonate at the 3'-most terminal linkage; a 3' C5-aminoalkyl-dT; 3' cationic group; or another 3' conjugate to inhibit 3'-5' exonucleolytic degradation. Non-limiting examples of 5'-phosphate modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—(HO)(O)P—O—P(HO)(O)—O-5'); 5'-adenosine cap (Appp), and any modified or unmodified nucleotide cap structure (N—O-5'-(HO)(O)P—O—(HO)(O)P—(HO))P—O—P(HO)(O)—O-5'); 5'-monothiophosphate (phosphorothioate; (HO)2(S)P—O-5'); 5'-monodithiophosphate (phosphorodithioate; (HO)2(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH$_2$)(O)P—O-5'), 5'-alkylphosphonates (R=alkyl-methyl, ethyl, isopropyl, propyl, etc., e.g. RP(OH)(O)—O-5'-, (OH)2(O)P-5'-CH2-), 5'-alkyletherphospsphonates (R=alkylether=methoxymethyl (MeOCH2-), ethoxymethyl, etc., e.g. RP(OH)(O)—O-5'-).

Nuclease resistant antisense oligonucleotides can be prepared with nucleobases such as, e.g., inosine, thymine, xanthine, hypoxanthine, nubularine, isoguanisine, or tubercidine. Non-limiting examples of other substitute bases that can be used include 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and 0-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, N.sup.4-acetyl cytosine, 2-thiocytosine, N6-methyladenine, N6-isopentyladenine, 2-methylthio-N-6-isopentenyladenine, N-methylguanines, or O-alkylated bases.

To facilitate in vivo delivery and stability, the antisense oligonucleotide may be linked to a steroid, such as cholesterol moiety, a vitamin, a fatty acid, a carbohydrate or glycoside, a peptide, or other small molecule ligand at its 3' end.

Other modifications of antisense oligonucleotides are known in the art and are suitable for use in the present invention.

It is not necessary for all positions in a given oligonucleotide to be uniformly modified. More than one of the aforementioned modifications may be incorporated in a single oligonucleotide or even within a single nucleoside within an oligonucleotide. The present invention also includes "chimeric" oligonucleotides, which contain two or more chemically distinct regions, each made up of at least one nucleotide. These chimeric oligonucleotides typically contain at least one region wherein the oligonucleotide is modified so as to confer increased resistance to nuclease degradation, increased cellular uptake, and/or increased binding affinity for the target nucleic acid or protein. An additional region of the oligonucleotide may serve as a substrate for enzymes or as a means for oligonucleotide detection.

Useful modifications of miRNA inhibitory oligonucleotides of the invention also include miRCURY LNA™ microRNA inhibitors and miRCURY LNA™ microRNA Power inhibitors (Exiqon). miRCURY LNA™ microRNA inhibitors are DNA/LNA™ mixmer antisense oligonucleotides (a combination of LNA monomers and DNA monomers) with normal phosphodiester nucleotide bonds. miRCURY LNA™ microRNA Power inhibitors have a fully phosphorothioate (PS) modified backbone which makes them highly resistant to enzymatic degradation.

In one specific embodiment of the invention, oligonucleotide modification is selected from the group consisting of locked nucleic acids (LNA), 2'-fluoro (2'-F) modified nucleotides, 2'-O-methoxyethyl (2'-MOE) modified nucleotides, 2'-O-methyl (2'O-Me) modified nucleotides, and phosphorothiate (PS) nucleotides.

In one specific embodiment, the miRNA inhibitory oligonucleotide is selected from the group consisting of LNA oligonucleotides 5'-TTCTGTAGTGCACTG-3' (SEQ ID NO: 52; anti-miR-148a) and 5'-AACTTAGCCACTGTGA-3' (SEQ ID NO: 54; anti-miR-27b), miRCURY LNA™ microRNA inhibitors 5'-ACAAAGTTCTGTAGTGCAC-3' (SEQ ID NO: 33; anti-miR-148a) and 5'-AGAACTTAGC-CACTGTGA-3' (SEQ ID NO: 34; anti-miR-27b), and miRCURY LNA™ microRNA Power inhibitors 5'-ACAAAGT-TCTGTAGTGCAC-3' (SEQ ID NO: 33; anti-miR-148a) and 5'-AGAACTTAGCCACTGTGA-3' (SEQ ID NO: 34; anti-miR-27b).

Oligonucleotide Preparation

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides. Preparation of LNA and derivatives has been described, for example, in PCT Publications Nos. WO 98/39352 and WO 99/14226; Koshkin et al., Tetrahedron, 1998, 54, 3607-3630; Kumar et al., Bioorg. Med. Chem. Lett., 1998, 8, 2219-2222; Singh et al., J. Org. Chem., 1998, 63, 10035-10039. Representative patents that teach the preparation of the phosphorus-containing linkages comprise, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Representative patents that teach the preparation of the oligonucleotides having backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages comprise, but are not limited to, U.S. Pat. Nos. 5,034,506; 5,166,315, 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439. Representative patents that teach the preparation of PNA compounds comprise, but are not limited to, U.S. Pat. Nos. 5,539,082; 5,714,331; and 5,719,262. See also Nielsen et al., Science, 1991, 254, 1497-1500. Representative patents that teach the preparation of modified sugar structures comprise, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920. Representative patents that teach the preparation of the modified nucleobases comprise, but are not limited to, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941. Representative patents that teach the preparation of oligonucleotide conjugates comprise, but are not limited to, U.S. Pat. Nos. 4,828,979; 4,948,882; 5,218,105; 5,525,465; 5,541,313; 5,545,730; 5,552, 538; 5,578,717, 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5, 245,022; 5,254,469; 5,258,506; 5,262,536; 5,272,250; 5,292.873; 5,317,098; 5,371,241, 5,391, 723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599, 928 and 5,688,941. Representative patents that teach the preparation of chimeric oligonucleotides comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922.

Pharmaceutical Compositions of the Invention

For administration to human and animal patients, the oligonucleotides of the present invention can be formulated in pharmaceutical compositions in combination with one or more pharmaceutically acceptable carriers and/or excipients such as, e.g., lubricants, diluents, flavorants, colorants, buffers, and disintegrants. Suitable pharmaceutically acceptable carriers include any and all conventional solvents (such as, e.g., water, physiological solution, dextrose, glycerol, ethanol, and the like, as well as combinations thereof), wetting agents, emulgators, buffers, conservants, dispersion media, fillers, solid carriers, aqueous solutions, coatings, antibacterial and antifungal agents, isotonic and absorption delaying agents, as well as other well-known agents which enhance the shelf life or effectiveness of one or more of the active components of the composition. Examples of such useful substances can be found in "Remington's Pharmaceutical Sciences" by E. W. Martin. Except insofar as any conventional media or agent is incompatible with the active ingredient, use thereof in compositions of the present invention is contemplated. The term "pharmaceutically acceptable" refers to a carrier or excipient that does not cause an allergic reaction or other untoward effect in patients to whom it is administered.

The pharmaceutical compositions of the invention can be produced in useful dosage units for administration by various routes including, among others, topical, oral, subcutaneous, intravenous, and intranasal administration.

The pharmaceutical compositions of the invention can also include other biologically active substances in combination with the oligonucleotides of the invention. Such additional biologically active substances can be also formulated as separate compositions and can be administered simultaneously or sequentially with the oligonucleotides of the invention. Non-limiting examples of useful biologically active substances include statins, niacin, bile-acid resins, fibric acid derivatives, cholesterol absorption inhibitors, and other lipid-lowering drugs.

Oligonucleotide Administration

With the aid of present disclosure, those of skill in the art should be able to derive suitable dosages and schedules of administration for any of a number of suitable compositions that contain the oligonucleotides of the invention. Thus, pharmaceutical compositions within the scope of the present invention include compositions where the active ingredient(s) is contained in an effective amount to increase plasma high-density lipoprotein cholesterol (HDL-C) level and/or reduce plasma low-density lipoprotein cholesterol (LDL-C) level.

The formulation and dose for therapeutic administration of the oligonucleotides of the invention will depend on the severity of the disease condition being treated, whether other drugs are being administered, whether other actions are taken, the weight, age, and sex of the subject, and other criteria. The skilled medical practitioner will be able to select the appropriate formulation and dose in view of these criteria and based on the results of published clinical trials. The dosage and administration regimen can be further adjusted for an individual patient by monitoring the level of HDL-C and/or LDL-C.

The optimal therapeutically effective amount of an oligonucleotide or composition of this invention may be determined experimentally, taking into consideration the exact mode of administration, the form in which the drug is administered, the indication toward which the administration is directed, the subject involved (e.g., body weight, health, age, sex, etc.), and the preference and experience of the physician or veterinarian in charge.

As disclosed herein, the concentrations of the oligonucleotides administered in the present invention are both therapeutically effective and pharmaceutically acceptable. The oligonucleotides of the present invention are preferably used in vivo at 0.1-5 mg/kg of body weight, most preferably at 0.5-2 mg/kg of body weight.

Following methodologies which are well-established in the art, effective doses and toxicity of the oligonucleotides and compositions of the present invention, which performed well in in vitro tests, can be determined in studies using small animal models (e.g., mice, rats) in which they have been found to be therapeutically effective and in which these drugs can be administered by the same route proposed for the human trials.

For any pharmaceutical composition used in the methods of the invention, dose-response curves derived from animal systems can be used to determine testing doses for administration to humans. In safety determinations for each composition, the dose and frequency of administration should meet or exceed those anticipated for use in any clinical trial.

As disclosed herein, the dose of the oligonucleotide in the compositions of the present invention is determined to ensure that the dose administered continuously or intermittently will not exceed an amount determined after consideration of the results in test animals and the individual conditions of a patient. A specific dose naturally varies (and is ultimately decided according to the judgment of the practitioner and each patient's circumstances) depending on the dosage procedure, the conditions of a patient or a subject animal such as age, body weight, sex, sensitivity, feed, dosage period, drugs used in combination, seriousness of the disease, etc.

Toxicity and therapeutic efficacy of the compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it can be expressed as the ratio $ED_{50}/LD_{50}$.

The oligonucleotides of the invention can be formulated for parenteral, oral, topical, transdermal, transmucosal, intranasal, buccal administration, or by any other standard route of administration. Parenteral administration includes, among others, intravenous (i.v.), subcutaneous (s.c.), intraperitoneal (i.p.), intramuscular (i.m.), subdermal (s.d.), intradermal (i.d.), intra-articular, intra-synovial, intra-arteriole, intraventricular, intrathecal, intrasternal, intrahepatic, intralesional, or intracranial administration, by direct injection, via, for example, bolus injection, continuous infusion, or gene gun. A preferred route of administration according to the present invention will depend primarily on the indication being treated and includes, among others, topical, oral, subcutaneous, intravenous, and intranasal administration.

Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water, before use. Suitable formulations for parenteral administration may contain substances which increase viscosity, for example, sodium carboxymethyl cellulose, sorbitol, and/or dextran. Optionally, the formulation may also contain stabilizers. Additionally, the oligonucleotides of the present invention may also be administered encapsulated in liposomes. The oligonucleotide, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such a diacetylphosphate, stearylamine, or phosphatidic acid, and/or other materials of a hydrophobic nature.

For oral administration, the formulations of the invention can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. The compositions of the invention can be also introduced in microspheres or microcapsules, e.g., fabricated from poly glycolic acid/lactic acid (PGLA) (see, U.S. Pat. Nos. 5,814,344; 5,100,669 and 4,849,222; PCT Publication Nos. WO 95/11010 and WO 93/07861). Liquid preparations for oral administration can take the form of, for example, solutions, syrups, emulsions or suspensions, or they can be presented as a dry product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound.

For administration by inhalation, the therapeutics according to the present invention can be conveniently delivered in the form of an aerosol spray presentation from pressurized packs or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

In addition to the formulations described previously, the compositions can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Oligonucleotide Delivery

Compositions of the present invention can be delivered systemically or locally. If targeted delivery to a particular cell or tissue is desirable (e.g, liver), oligonucleotide conjugates or oligonucleotide delivery vectors containing antibodies to cell- or tissue-specific antigens can be used.

As specified above, some of the oligonucleotides of the present invention (e.g., 15-mers and smaller) are small enough to enter cells without transfection or other methods of facilitating cell entry. Other oligonucleotides can be chemically modified (e.g., by chemically linking them to a lipophilic moiety or other heterologous moiety) to enhance their cellular uptake. However, even these oligonucleotides may require specific delivery methods and delivery systems to ensure their efficient and targeted delivery to the tissue to be treated. Oligonucleotide delivery methods of the present invention include both local and systemic administration of stabilized nucleic acids, oligonucleotides incorporated into delivery vectors, and/or oligonucleotides conjugated to peptides or small molecules that are subsequently transported into cells. Mechanical and electrical strategies for targeted oligonucleotide delivery include microinjection, particle bombardment, the use of pressure, and electroporation.

Nanoparticles, miRNA sponges and vector-mediated delivery approaches can be used. Vector-assisted oligonucleotide delivery systems include biological viral delivery systems and chemical non-viral delivery systems. Viral delivery systems include without limitation retroviruses, parvoviruses, adenoviruses, lentiviruses, adeno-associated viruses, herpes simplex virus, pseudovirions, etc. Non-viral delivery systems (which are clinically preferable due to lack of immune response and ease of formulation and assembly) include (i) polymeric delivery systems (oligonucleotide-polymer complexes) and (ii) liposomal delivery systems (oligonucleotides entrapped in and/or complexed to liposomes). Commonly used polymers in polymeric delivery systems include, for example, polyethylenimine (PEI), poly (L-lysine) (PLL), chitosans, and polyamidoamine (PANAM) dendrimers (e.g., commercially available Superfect and Polyfect [Qiagen, Valencia, Calif.]). Agents such as folates, transferrin, antibodies, or sugars such as galactose and mannose can be also incorporated for tissue targeting.

Liposomal delivery systems include systems that deliver oligonucleotides either by entrapping them inside an aqueous core or complexing them to the phospholipid lamellae. Similarly to viral vectors, liposomes offer substantial protection to the oligonucleotide therapeutics from nucleases and improve their biological stability. Liposomes may also offer significant advantages over viral delivery options for the delivery of oligonucleotide therapeutics due to much lower immunogenicity (because they lack proteinaceous components) and their versatility. Since the phospholipid composition in the liposome bilayers can be varied, liposomal delivery systems can be easily engineered to yield a desired size, surface charge, composition, and morphology. Liposomes for oligonucleotide delivery according to the present invention can include a variety of cationic, anionic, synthetically modified lipids, and combinations thereof.

Examples of cationic lipids include without limitation 33[N—(N',N'-dimethylaminoethane)-carbamoyl] cholesterol (DC-chol)/DOPE, 1,2-dioleoyl-3-trimethylammonium propane (DOTAP), N-[1-(2,3-dioleyloxy)propyl]-N,N,N-trimethylammonium chloride (DOTMA), 2,3-dioleoyloxy-N-[2-(sperminecarboxamido)ethyl]-N,N-dimethyl-1-propanaminium (DOSPA), dioctadecyl amido glycil spermine (DOGS), 3,[N—(N1,N-dimethylethylenediamine)-carbamoyl]cholesterol (DC-chol), polyethyleneimine (PEI), polyamidoamine (PAMAM) dendrimers, and poly-L-lysine (PLL). Commonly used zwitterionic lipids, also known as helper lipids, are DOPE, 1,2-dipalmitoyl-sn-glycero-3-phosphocholine (DPPC), and cholesterol. The cationic lipids in the liposomal formulation serve as an oligonucleotide complexation and condensation agents during the formation of the lipoplex. The positive charge also helps in cellular association. The zwitterionic lipids help in membrane perturbation and fusion. Proprietary formulations of cationic lipids such as Lipofectamine (Invitrogen. Carlsbad, Calif.), Effectene (Qiagen, Valencia, Calif.), and Tranfectam (Promega, Madison, Wis.) are commercially available.

Examples of anionic lipids include without limitation DPPC and 1,2-dimyristoyl-sn-glycero-3-[phospho-rac-(1-glycerol)](DMPG). LPDII vectors can be also used for delivery of the oligonucleotides of the present invention. These are non-viral delivery vehicles that consist of a complex between anionic pH-sensitive liposomes and poly-cation-condensed oligonucleotides (polyplexes). Another useful delivery vehicle can be composed of a mixture of anionic lipid 1,2-dioleoyl-sn-glycero-3-[phospho-rac-(1-glycerol)](sodium salt) (DOPG) and zwitterionic lipid DOPE.

Other useful specialized liposomal delivery platforms include pH-sensitive liposomes, immunoliposomes, and stealth liposomes. pH-sensitive liposomes can be generated by the inclusion of DOPE or citraconyl-DOPE or phosphatidylcholine/glycyrrhizin combination into liposomes composed of acidic lipids such as cholesterylhemisuccinate or oleic acid. At the neutral cellular pH 7, these lipids have the typical bilayer structure; however, upon endosomal compartmentalization they undergo protonation and collapse into a non-bilayer structure, thereby leading to the disruption and destabilization of the endosomal bilayer, which in turn helps in the rapid release of the oligonucleotide into the cytoplasm. Immunoliposomes incorporate functionalized antibodies attached to lipid bilayers and thus target specific receptors and facilitate receptor-mediated endocytosis for the uptake of the lipoplex. Stealth liposomes are sterically stabilized liposomal formulations that include polyethylene glycol (PEG)-conjugated lipids. Pegylation prevents the opsonization and recognition of the liposomal vesicles by the reticuloendothelial system. Consequently, stealth liposomes have long circulating times in the systemic circulation.

Liposomes useful for oligonucleotide delivery according to the present invention can take a shape of multilamellar vesicles (MLV) formed by reconstituting thin lipid films in buffer. Small unilamellar vesicles (SUV) of specific size (100-500 nm) can be produced by extruding MLV through polycarbonate membranes. SUV (50-90 nm) can also be produced by sonication of MLV or larger SUV.

Transmembrane permeation of the oligonucleotides of the invention can be also enhanced by inclusion of cell penetrating peptides (CPPs; also termed "peptide transduction domain" (PTD)) in the delivery vehicles or covalent oligonucleotide conjugation to such peptides. Conjugated CPPs are also contemplated for use as a heterologous moiety of the present invention. CPPs/PTDs are a class of small cationic peptides of approximately 10-30 amino acids in length that have been shown to engage the anionic cell surface through electrostatic interactions and rapidly induce their own cellular internalization through various forms of endocytosis. Examples of useful CPPs/PTDs include TAT peptide, penetratin, an Antennepedia domain, transportan, poly-arginine, and MPG.

Other compounds useful in delivery of the oligonucleotides of the present invention include cyclodextrins (CyDs), porphyrin derivatives, branched chain dendrimers, polyethylenimine polymers, nanoparticles, microspheres, and polylysine conjugates with vector proteins such as asialofetuin or transferrin.

Preferred methods of oligonucleotide delivery according to the present invention include Lipofectamine 2000 or Lipofectamine RNAiMAX (Invitrogen) (used to transfect oligonucleotides into cells), antibodies, peptides, liposomes, and nanoparticles. Other methods include addition of naked oligonucleotides.

More information on useful delivery vehicles and methods can be obtained from recent reviews such as, e.g., Meade and Dowdy, Adv Drug Deliv Rev., 2008, 60(4-5): 530-6; Juliano et al., Nucleic Acids Res., 2008, 36(12): 4158-71; Lysik and Wu-Pong, J. Pharmaceutical Sciences, 2003, 92: 1559; Dass, J., Pharmacy Pharmacol., 2002, 54 (1): 3-27, and references cited therein. See also Lorenz et al., Bioorg Med Chem Lett., 2004, 14(19): 4975-7; Dalby et al., Methods, 2004 33(2): 95-103; Hassani et al., J. Gene Med., 2005, 7(2): 198-207; Pirollo et al., Hum Gene Ther., 2006, 17(1): 117-24; Jaaskelainen et al., Eur J Pharm Sci., 2000, 10(3): 187-93; Urban-Klein et al., Gene Ther., 2005, 12(5): 461-6; Zhou et al., Chem. Commun. (Camb), 2006, 22: 2362-4; Leng et al., J. Gene Med., 2005, 7(7): 977-86.

In vivo nuclease degradation of oligonucleotides of the invention can be circumvented by chemical derivatization of the backbone and/or by the protection and stability offered by the above-described vector delivery systems. As discussed above, various chemical modifications to the backbone can be used to improve oligonucleotide stability. The most common modifications include the introduction of phosphorothioate and/or methyl phosphonate linkages in the backbone. Phosphorothioate analogs are chosen for their stability against nucleases and the methylphosphonate backbone for its relative hydrophobicity and ease of diffusion across membranes. Mixed-backbone oligonucleotides can also be used. To ensure protection of the oligonucleotides of the invention from the endosomal degradation upon intracellular delivery, viral delivery vectors or pH-sensitive and cationic liposome delivery systems (e.g., including fusogenic lipids such as 1,2-dioleoyl-sn-glycero-3-phosphoethanolamine (DOPE)). Lysosomatropic agents such as monensin and chloroquine, which raise the endosomal pH, block acidification, and thus inhibit lysozyme activity, can also be used to facilitate endosomal release of the oligonucleotides of the invention. In addition, endosomal degradation of oligonucleotides can be circumvented by the incorporation of viral peptides such as hemagglutinin HA2 and those derived from adenoviruses in their delivery systems or by using fusogenic peptides such as poly(L-lysine) (PLL) and cationic polymers such as polyethylenimine (PEI) and dendrimers. See the review by Patil et al., AAPS J., 2005, 7(1): E61-E77 and references cited therein.

Therapeutic Methods of the Invention

In conjunction with the novel oligonucleotides of the present invention, provided herein are methods of treatment using such oligonucleotides. Specifically, the invention provides a method for treating a disease in a subject in need thereof, which method comprises administering to the subject a therapeutically effective amount of one or more oligonucleotides of the invention or a composition comprising such one or more oligonucleotide(s). Non-limiting examples of the diseases treatable by the method of the invention include dyslipidemias (such as, e.g., hyperlipidemia [elevated lipid levels], hypercholesterolemia [elevated cholesterol levels], low HDL/LDL ratio) and cardiovascular diseases (such as, e.g., atherosclerosis, coronary artery disease, coronary heart disease, conditions associated with coronary artery disease or coronary heart disease [e.g., angina, myocardial infarction], transient ischemic attack, stroke). In a preferred embodiment, the subject is human.

EXAMPLES

The present invention is further described by way of the following particular examples. However, the use of such examples is illustrative only and is not intended to limit the scope or meaning of this invention or of any exemplified term. Nor is the invention limited to any particular preferred embodiment(s) described herein. Indeed, many modifications and variations of the invention will be apparent to those skilled in the art upon reading this specification, and such "equivalents" can be made without departing from the invention in spirit or scope. The invention is therefore limited only by the terms of the appended claims, along with the full scope of equivalents to which the claims are entitled.

Example 1

Materials and Methods

The LDLR-GFP plasmid was provided by Dr. Peter Tontonoz (UCLA, Los Angeles, Calif.). Chemicals were obtained from Sigma-Aldrich unless otherwise noted. The synthetic LXR ligand T0901217 (T090) was purchased from Cayman Chemical. Human ApoA1 was obtained from Meridian Life Sciences. Lipoprotein-deficient serum (LPDS) was prepared from FBS delipidated with 4% fumed silica. 1,1'-Dioctadecyl-3,3,3,3'-tetramethylindocarbocyanineperclorate (DiI) was purchased from Molecular Probes (Invitrogen). A mouse monoclonal antibody against ABCA1 was purchased from Abcam. A rabbit polyclonal antibody against LDLR was obtained from Cayman Chemical and a mouse monoclonal antibody against HSP90 was purchased from BD Bioscience. A mouse monoclonal antibody against LDLR was obtained from Santa Cruz. Secondary fluorescently labeled antibodies were from Molecular Probes (Invitrogen). miRNA mimics and inhibitors were obtained from Life Technologies. siRNAs were purchased from Dharmacon and locked nucleic acid (LNA) miRNA detection probes were purchased from Exiqon (Woburn, Mass.). For in vivo experiments, in vivo locked nucleic acid (LNA)™ miRNA inhibitors against mmu-miR-148a-3p (5'-TTCTGTAGTG-CACTG-3'; SEQ ID NO: 52), mmu-miR-27b-3p (5'-AACT-TAGCCACTGTGA-3'); SEQ ID NO: 54) or scrambled control (5'-ACGTCTATACGCCCA-3'; SEQ ID NO: 51) were purchased from Exiqon.

Cell Culture

Human (Huh7) and mouse (Hepa) hepatic cells and monkey kidney fibroblast (COS7) and Hela cells were obtained from American Type Tissue Collection. Huh7, Hepa and COS7 cells were maintained in Dulbecco's Modified Eagle Medium (DMEM) containing 10% fetal bovine serum (FBS) and 2% penicillin-streptomycin in 10 cm$^2$ dishes at 37° C. and 5% $CO_2$. For DiI-LDL uptake and binding experiments, Huh7 cells were cultured in DMEM containing 10% LPDS and incubated with 30 μg/ml DiI-LDL cholesterol. For analysis of miR-27b and miR-148a expression, Huh7 cells were cultured in DMEM containing 10% LPDS and left untreated or treated with nLDL (120 μg/ml) for 24 h. For analysis of miR-148a expression, Huh7 cells were cultured in DMEM 10% FBS and transfected with 1 μg pcDNA3.1-2×FLAG-SREBP-1c (Addgene) or 1 μg pcDNA empty vector for 24 h using Lipofectamine LTX (Invitrogen).

Hepatocytes were isolated from 8-week old male mice by isopynic centrifugation as previously described (Gao, 2013 and Birmingham 2009). On day zero, isolated hepatocytes were plated on six-well collagen-1-coated dishes (400,000 cells/well) in 2 ml Adherence culture medium (William's E medium supplemented with 5% fetal bovine serum, 10 mM HEPES buffer, 2 mM L-glutamine, 8 μg/ml Gentamicin, 1 μM Dexamethasone and 1 nM insulin). After incubation at 37° C. and 5% $CO_2$ for 4-6 h, the attached cells were washed once in 1×PBS and then incubated at 37° C. and 5% for 14-16 h in 2 ml Basal maintenance media (William's E medium supplemented with 5% LPDS, 2 mM L-glutamine, 8 μg/ml Gentamicin, 1 μM Dexamethasone and 1 nM insulin). On day one, cells in each well were washed once with 1×PBS, and supplemented with 2 ml fresh maintenance media without insulin with or without 3 μM T090 or 30 nM insulin. After incubation for 6 h (insulin experiments) or 12 h (T090 experiments) at 37° C., cells were harvested for RNA extraction, immunoblotting and northern blotting.

miRNA Screen

All steps of the genome-wide miRNA screen, including reverse transfection and image acquisition and analysis, were performed at the NYU RNAi Core Facility (NYU School of Medicine).

Reverse Transfection, Fixation and Staining.

Huh7 cells were reverse transfected in triplicate with a library of 1719 miRNA mimics (Life Technologies mirVana Mimic Library, miRBase release 17.0) in Corning 384-well flat clear-bottom black plates (Fisher Scientific) using a standard reverse transfection protocol. Briefly, Huh7 cells (5,000 cells/well in 30 µl of DMEM media containing 10% LPDS) were seeded into a well containing 30 µl of transfection mix (25 µl of Optimem, 0.07 µl RNAi Max (Invitrogen), and 5 µl of 0.3 µM miRNA or control siRNA). 20 µl of fresh LPDS media was added to all wells 12 h post transfection, giving a final mimic concentration of 18 nM. 48 h later, cells were incubated with 10 µl of fresh LPDS containing 30 µg/ml of DiI-LDL for 8 h at 37° C. Following incubation, cells were washed twice with 1×PBS and fixed with 4% PFA for 15 min. After three subsequent washes with 1×PBS, cells were incubated with PBS containing 1 µg/ml Hoechst (Molecular Probes) for 25 min. Before scanning, a final wash with 1×PBS was performed and plates were spun down to minimize contaminants when imaging with the automated microscope. All liquid handling steps, including seeding, DiI-LDL incubation, fixation, washing, and Hoechst incubation were performed using a Wellmate Microplate Dispenser (Matrix Technologies) and BioTek Plate Washer (PerkinElmer). The triplicate screen consisted of fifteen 384-well plates and was completed over the course of four days.

Image Acquisition and Analysis.

Automated high content and throughput images were acquired using an Arayscan VTI HCS Reader (Thermo Scientific) with a Zeiss 10× objective. 384-well plates were loaded onto the microscope using a Catalyst Express robotic arm and imaged overnight. In each well, cell nuclei and DiI-LDL intensities were imaged in 5 predefined fields. Image data was analyzed using BioApplication's Target Activation V3 image analysis software (Thermo Scientific). Briefly, nuclei were first identified on the Hoechst stain (Channel 1). Following this, cell boundaries were estimated using the geometric segmentation method and used to calculate DiI intensity (Channel 2) within each cell. In total, valid object count, mean average intensity, and total average intensity of DiI were recorded for each field. For the primary screen, 57,600 images, consisting of on average 533,528 objects/plate, were analyzed.

Figure 1:
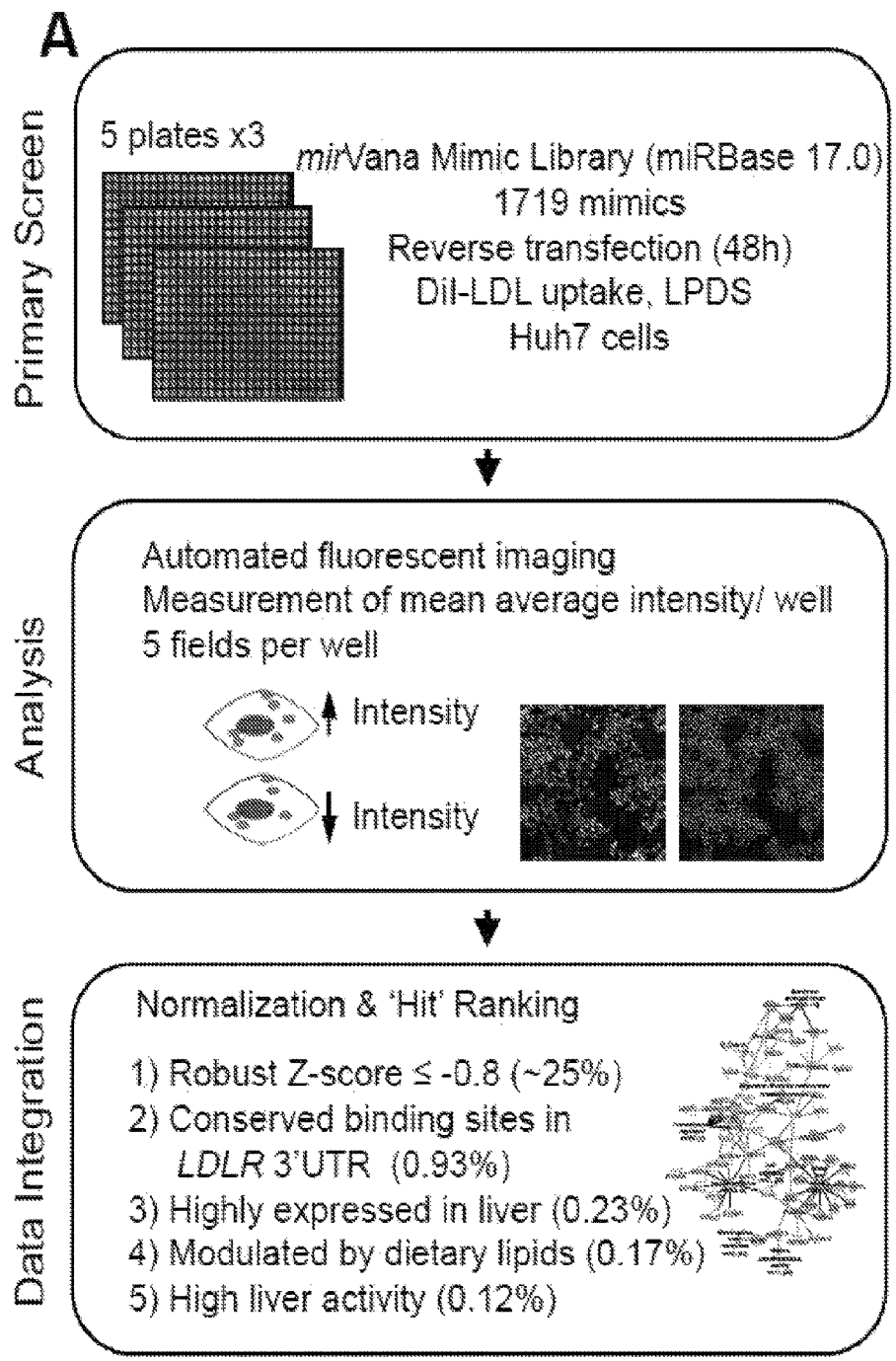
FIGS. 1A-F. Genome-wide miRNA screen identifies novel regulators of LDLR activity. (A) Schematic workflow of primary screen and bioinformatic procedures. (B-D) Linear regression analysis between DiI-LDL mean average intensity for plate set 1 and 2 (B), plate set 2 and 3 (C) and plate set 1 and 3 (D). The goodness of fit (r2) and regression line (indicative of overall reproducibility of the screen) is indicated on each graph. (E) DiI-LDL mean average intensity (MAI, open bars) and robust Z-score (dots) comparison for cells transfected with the negative control siRNA (non-silencing, NS) or positive control siRNA (siRNA LDLR, siLDLR). (F) Distribution of average robust Z-scores for individual miRNAs in the primary screen. Controls are represented by the grey (NS siRNA) and black (siLDLR) dots. miR-27b and miR-148a, highlighted in dark grey and light grey, respectively, were chosen for further validation based on predefined criteria (A, lower panel). All other miRNAs are shown in black.
Figure 1:
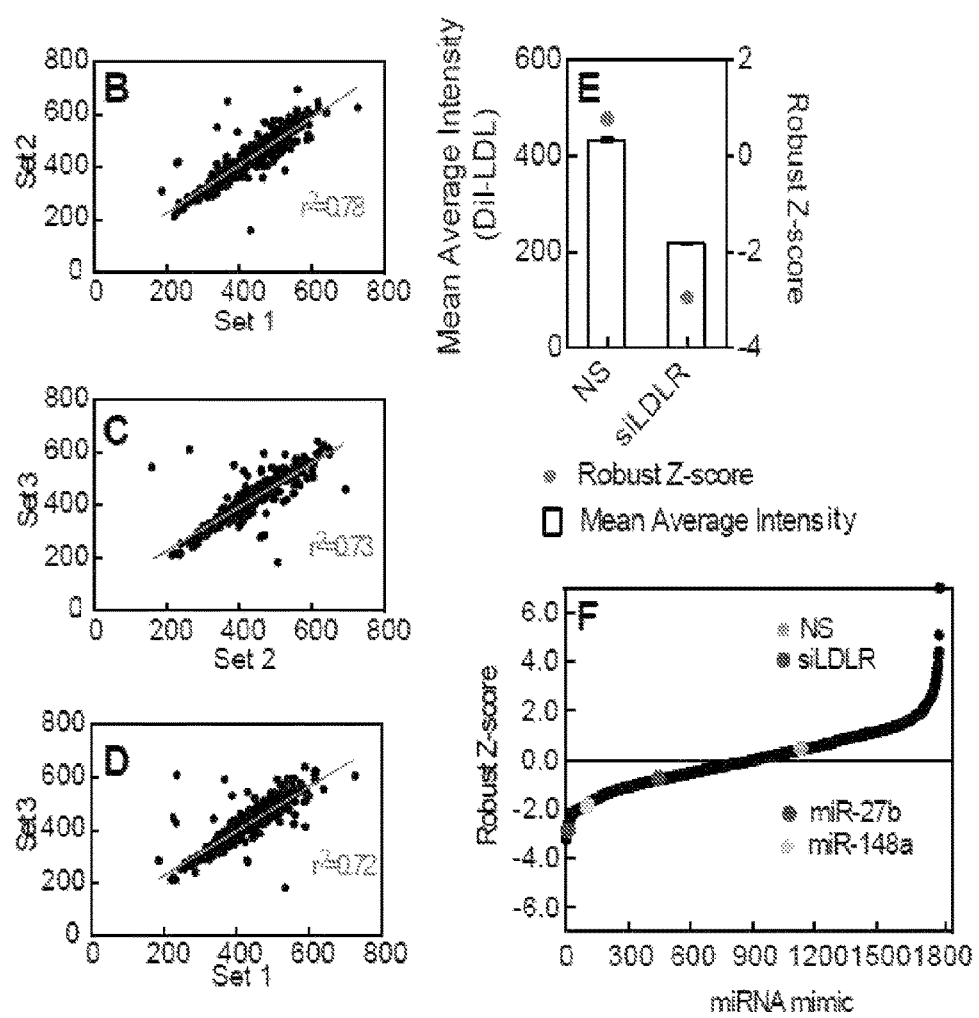

Hit Classification.

miRNAs were scored based on their ability to significantly increase or decrease DiI intensity compared to negative controls. Cytotoxic miRNA overexpression phenotypes were filtered for hit classification by excluding wells in which fewer then 500 cells were identified as valid objects. In addition, 32 validated internal controls, including non-silencing (NS) siRNA and siLDLR (FIG. 1), as well as the negative control miRNAs and siRNA KIF11 (Life Technolgogies) were used on each plate to monitor transfection efficiency. After confirming efficient transfection efficiency, mean average intensities of each well were normalized to plate medians and converted to robust Z-scores using Matlab, as previously described (Birmingham, Selfors et al. 2009). Robust Z-scores were compared between each plate replicate and the mean of each score was calculated and used to rank potential candidates. Those miRNAs that had a robust Z-score of ≤−0.8 (423, 25% of miRNAs screened) were chosen for further characterization. To narrow down candidate miRNA genes, hits were subjected to several screening passes (FIG. 1A, lower panel). Briefly, these candidates were filtered based on whether they were predicted to target the LDLR (40 miRNAs, 2% of miRNAs screen), the binding sites were conserved (16 miRNAs, 0.93% of miRNAs screened), they were highly expressed in mouse or human liver (4 miRNAs, 0.23% of miRNAs screened), they responded to dietary cholesterol (3 miRNAs, 0.16% of miRNAs screened), and had high liver activity (2 miRNAs, 0.12% of miRNAs screened).

Bioinformatic Analysis of miRNA Target Genes.

Figure 9:
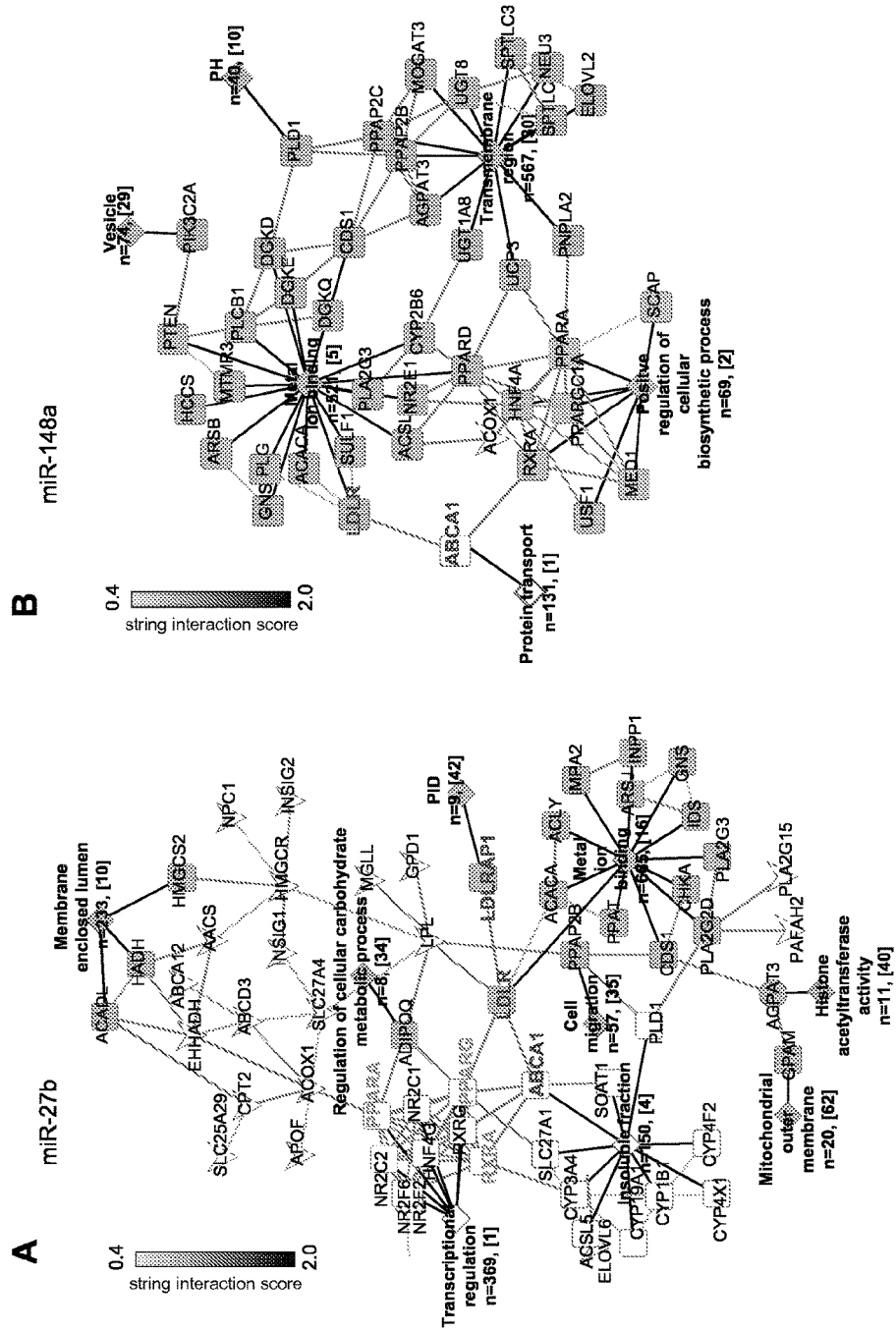

Target genes for hsa-miR-27b and hsa-miR-148a were identified and compared using the online target prediction algorithm, miRWalk (http://www.umm.uni-heidelberg.de/apps/zmf/mirwalk/), which provides target interaction information from eight different prediction algorithms. Specifically, the programs miRanda, miRWalk and TargetScan were used. Putative targets produced by all three of these algorithms for miR-27b (2,929 targets) and miR-148a (2,217 targets) were uploaded into DAVID v6.7 for functional annotation clustering (Huang da, 2009a and Huang da, 2009b). "High" classification stringency settings yielded 447 functional annotation clusters for miR-27b and 398 functional annotation clusters for miR-148a, of which 78 clusters (miR-148a) and 77 clusters (miR-27b) were highly enriched (E≥1.0). In another set of analyses, the present inventors took the putative targets for miR-27b and miR-148a identified above and uploaded them into the gene classification system, PANTHER v8.0 (Thomas, 2003 and Mi 2010) to identify gene targets that were mapped to the lipid metabolic process (GO:0006629). The functional interactions of these predicted targets (150 for miR-27b and 110 for miR-148a) described in STRING v9.05 (Franceschini, 2013) were then combined with the functional annotation groups described in DAVID. Matlab and Cytoscape v2.8.3 were used to create the visualization networks, as previously described (Mercer, Snijder et al. 2012). STRING interactions with a confidence score of 0.4 or higher were added and highlighted in grey (FIG. 9). Smaller annotation clusters and unconnected genes were left out of the visualization due to space constraints.

siRNA and miRNA Mimic/Inhibitor Transfections

For siRNA transfections, Huh7 cells were transfected with 60 nM of SMARTpool ON-TARGETplus LDLR siRNA or 60 nM of ON-TARGETplus Non-Targeting pool (Dharmacon) for 48 h in LPDS medium. Verification of LDLR knockdown was assessed by Western blotting, as described below. For mimic and inhibitor transfections, Huh7 and Hepa cells were transfected with 40 nM mirVana™ miRNA mimics (miR-27b and miR-148a) or with 60 nM mirVana™ miRNA inhibitors (Inh-27b and Inh-148a) (Life Technologies) utilizing RNAimax (Invitrogen) or Lipofectamine 2000 (Invitrogen). All experimental control samples were treated with an equal concentration of a non-targeting control mimic sequence (CM) or inhibitor negative control sequence (CI) for use as controls for non-sequence-specific effects in miRNA experiments. Verification of miR-27b and miR-148a over-expression and inhibition was determined using qRT-PCR, as described below.

RNA isolation and Quantitative Real-Time PCR

Total RNA was isolated using TRIzol reagent (Invitrogen) according to the manufacturer's protocol. For mRNA quantification, cDNA was synthesized using iScript RT Supermix (Bio-Rad), following the manufacturer's protocol. Quantitative real-time PCR (qRT-PCR) analysis was performed in triplicate using iQ SYBR green Supermix (BioRad) on an iCycler Real-Time Detection System (Eppendorf). The mRNA level was normalized to GAPDH or 18S as a house keeping gene. The human primer sequences used were: GAPDH, 5'-TTGATTTTGGAGGGATCTCG-3' (SEQ ID NO: 11) and 5'-CAATGACCCCTTCATTGACC-3' (SEQ ID NO: 12); LDLR, 5'-TGATGGGTTCATCTGACCAGT-3' (SEQ ID NO: 13) and 5'-AGTTGGCTGCGTTAATGT-GAC-3' (SEQ ID NO: 14); LDLRAP1 5'-ATCGTGGCTA-CAGCTAAGGC-3' (SEQ ID NO: 15) and 5'-CAAACAC-CTTGTCGTGCATC-3' (SEQ ID NO: 16); and ABCA1, 5'-TGTCCTCATACCAGTTGAGAGAC-3' (SEQ ID NO: 17) and 5'-GGTGATGTTTCTGACCAATGTGA-3' (SEQ ID NO: 18). The mouse primers sequences used were: LDLR, 5'-GGTACTGGCAACCACCATTGGG-3' (SEQ ID NO: 19) and 5'-GCCAATCGACTCACGGGTTCAG-3' (SEQ ID NO: 20); 18S, 5'-TTCCGATAACGAACGA-GACTCT-3' (SEQ ID NO: 21) and 5'-TGGCTGAACGC-CACTTGTC-3' (SEQ ID NO: 22); ABCA1, 5'-GGTTTG-GAGATGGTTATACAATAGTTGT-3' (SEQ ID NO: 120) and 5'-CCCGGAAACGCAAGTCC-3' (SEQ ID NO: 121); SREBP1c, 5'-GGAGCCATGGATTGCACATT-3' (SEQ ID NO: 122) and 5'-ACAAAGTTGCTCT-GAAAACAAATCA-3' (SEQ ID NO: 123); and FASN, 5'-GGAGGTGGTGATAGCCGGTAT-3' (SEQ ID NO: 124) and 5'-TGGGTAATCCATAGAGCCCAG-3' (SEQ ID NO: 125). For miRNA quantification, total RNA was reverse transcribed using the miScript II RT Kit (Qiagen). Primers specific for human and mouse pre-miR-27b, pre-miR-148a, miR-27b and miR148a (Qiagen) were used and values normalized to SNORD68 (Qiagen) as a housekeeping gene. For pri-miRNA quantification, cDNA was synthesized using TaqMan® reverse transcription reagents (Applied Biosystems), following the manufacturer's protocol. For pri-miR-148a, quantitative real-time PCR was performed in triplicate using TaqMan Universal Master Mix (Applied Biosystems) on a Real-Time PCR System (Applied Biosystems). Primers for human and mouse miR-148a were obtained from Applied Biosystems. For pri-miR-27b quantification, quantitative real-time PCR was performed in triplicate using SYBR Green Master Mix (SA Biosciences) on an iCycler Real-Time Detection System (Eppendorf). Primer sequences used for human pri-miR-27b were: 5'-GTTCCTGGCAT-GCTGATTTG-3' (SEQ ID NO: 23) and 5'-CTAAGCTCT-GCACCTTGTTAGA-3' (SEQ ID NO: 24) and primer sequences for mouse pri-miR-27 b were: 5'-GTTCCTG-GCATGCTGATTTG-3' (SEQ ID NO: 25) and 5'-CTAAGCTCTGCACCTTGTTAGA-3' (SEQ ID NO: 26). The pri-miRNA levels were normalized to 18S (Applied Biosystems) as a housekeeping gene.

For mouse tissues, total liver RNA from C57BL/6 mice (fed a chow or Western diet), from LDLR-/+; ApoB Tg mice, from ob/ob mice, or from Tg-SREBP1c mice was isolated using the Bullet Blender Homogenizer (Next Advance) in TRIzol. 1 µg of total RNA was reverse transcribed and gene/miRNA expression assessed as above.

Western Blot Analysis

Cells were lysed in ice-cold buffer containing 50 mM Tris-HCl, pH 7.5, 125 mM NaCl, 1% NP-40, 5.3 mM NaF, 1.5 mM NaP, 1 mM orthovanadate and 1 mg/ml of protease inhibitor cocktail (Roche) and 0.25 mg/ml AEBSF (Roche). Cell lysates were rotated at 4° C. for 1 h before the insoluble material was removed by centrifugation at 12000×g for 10 min. After normalizing for equal protein concentration, cell lysates were resuspended in SDS sample buffer before separation by SDS-PAGE. Following overnight transfer of the proteins onto nitrocellulose membranes, the membranes were probed with the following antibodies: ABCA1 (1:1000), LDLR (1:500), and HSP90 (1:1000). Protein bands were visualized using the Odyssey Infrared Imaging System (LI-COR Biotechnology). Densitometry analysis of the gels was carried out using ImageJ software from the NIH (Schneider, 2012 #219).

Northern Blot Analysis miRNA Expression was Assessed by Northern Blot Analysis as Previously described (Chamorro-Jorganes, 2014 #218). Briefly, total RNA (5 µg) was separated on a 15% acrylamide TBE 8M urea gel and blotted onto a Hybond N+ nylon filter (Amersham Biosciences). DNA oligonucleotides complementary to mature miR-148a-3p (5'-ACAAAGT-TCTGTAGTGCACTGA-3' [SEQ ID NO: 56]) were end-labeled with [a-$^{32}$P] ATP and $T_4$ polynucleotide kinase (New England Biolabs) to generate high-specific activity probes. Hybridization was carried out according to the ExpressHyb (Clontech) protocol. Following overnight membrane hybridization with specific radiolabeled probes, membranes were washed once for 30 min at 42° C. in 4×SSC/0.5% SDS and subjected to autoradiography. Blots were reprobed for 5 s rRNA (5'-CAGGCCCGACCCTGCTTAGCTTCCGAGA-GATCAGACGAGAT-3' [SEQ ID NO: 57]) to control for equal loading.

LDL Receptor Activity Assays

Human LDL was isolated and labeled with the fluorescent probe DiI as previously reported (Calvo, Gomez-Coronado et al. 1998). Huh7 cells were transfected in 6- or 12-well plates with miRNA mimics and inhibitors in DMEM containing 10% LPDS for 48 h. Then, cells were washed once in 1×PBS and incubated in fresh media containing DiI-LDL (30 µg cholesterol/ml). Non-specific uptake was determined in extra wells containing a 50-fold excess of unlabeled native LDL (nLDL). Cells were incubated for 8 h at 37° C. to allow for DiI-LDL uptake in screening optimization experiments and for 2 h at 37° C. for subsequent validation experiments. In other instances, cells were incubated for 30 min at 4° C. to assess DiI-LDL binding. At the end of the incubation period, cells were washed, resuspended in 1 ml of PBS and analyzed by flow cytometry (FACScalibur, Becton Dickinson), as previously described (Suarez, Fernandez et al. 2004). The results are expressed in terms of specific median intensity of fluorescence (M.I.F.) after subtracting autofluorescence of cells incubated in the absence of DiI-LDL.

Fluorescence Microscopy

For LDLR-Ab internalization and DiI-LDL uptake assays, Huh7 cells were grown on coverslips and transfected with a miR-27b mimic, miR-148a mimic or negative control mimic (CM) in DMEM containing 10% LPDS. 48 h post transfection, cells were cooled to 4° C. for 20 min to stop membrane internalization. Cells were then incubated with LDLR mAb (C7) (Santa Cruz) and 30 µg/ml DiI-LDL for 40 min at 4° C. Following incubation, cells were gently washed twice with cold medium and shifted to 37° C. to allow for internalization of both LDLR-Ab complexes and DiI-LDL for the indicated times and fixed with 4% PFA. After 5 min of Triton X-100 0.2% permeabilization and 15 min of blocking (PBS BSA 3%), cells were stained with anti-mouse Alexa 488 (Molecular Probes) and TO-PRO 3 (Life Technologies) for 1 h at room temperature. After this, cells were washed twice with 1×PBS and mounted on glass slides with Prolong-Gold (Life Technologies).

For LDLR-GFP rescue experiments, Huh7 cells were grown on coverslips and co-transfected with 1 μg LDLR-GFP and 40 nM of a control mimic CM, miR-27b mimic or miR-148a mimic. 48 h post transfection cells were incubated with 30 μg/ml DiI-LDL for 2 h at 37° C. (uptake) or with 30 μg/ml DiI-LDL for 90 min at 4° C. (binding). Then, cells were washed twice with 1×PBS, fixed with 4% PFA, and blocked (3% BSA in 1×PBS) for 15 min. Following this, cells were washed twice and mounted on glass slides with Prolong-Gold (Life Technologies). All images were analyzed using confocal microscopy (Leica SP5 II) equipped with a 63× Plan Apo Lenses. All gains for the acquisition of comparable images were maintained constant. Analysis of different images was performed using ImageJ (NIH) and Adobe Photoshop CS5.

3'UTR Luciferase Reporter Assays cDNA fragments corresponding to the entire 3'UTR of human LDLR, ABCA1 and LDLRAP1 were amplified by RT-PCR from total RNA extracted from HepG2 cells with XhoI and NotI linkers. The PCR product was directionally cloned downstream of the Renilla luciferase open reading frame of the psiCHECK2™ vector (Promega) that also contains a constitutively expressed firefly luciferase gene, which is used to normalize transfections. Point mutations in the seed region of the predicted miR-27b and miR-148a binding sites within the 3'UTR of LDLR, ABCA1 and LDLRAP1 were generated using the Multisite-Quickchange Kit (Stratagene), according to the manufacturer's protocol. All constructs were confined by sequencing. COS7 cells were plated into 12-well plates and co-transfected with 1 μg of the indicated 3'UTR luciferase reporter vectors and miR-27b mimics, miR-148a mimics, or control mimics (CM) (Life Technologies) utilizing Lipofectamine 2000 (Invitrogen). Luciferase activity was measured using the Dual-Glo Luciferase Assay System (Promega). Renilla luciferase activity was normalized to the corresponding firefly luciferase activity and plotted as a percentage of the control (cells co-transfected with the corresponding concentration of control mimic). Experiments were performed in triplicate wells of a 12-well plate and repeated at least three times.

miR-148a Promoter Assays

The promoter region (2.3 kb) of miR-148a was amplified by PCR from BAC clone RPCI-11-184C17 and cloned into a PGL3 promoter vector (Promega) using KpnI and HindIII linkers. The primers were: 5'-TGATGGCAGA-CAATAACTCC-3' (SEQ ID NO: 126) and 5'-AAAGT-GCTTTCCCATCTTCC-3' (SEQ ID NO: 127). All constructs were confirmed by sequencing. For some experiments, Hela cells were plated into 12-well plates and co-transfected with 0.5 μg of miR-148a promoter and 0.01 μg of Renilla luciferase reporter plasmid and 0.5 μg of pcDNA3.1-2×FLAG-SREBP1c or pcDNA3.1 empty control using Lipofectamine 2000. Cells were collected 24 h later. In another set of experiments, Huh7 cells were transfected with 0.5 μg of miR-148a promoter and 0.01 μg of Renilla luciferase reporter plasmid using Lipofectamine LTX. Following 24 h transfection, cells were stimulated with 3 μM T090 (12 h) or 100 nM insulin (8 h). Luciferase activity was measured using the Dual-Glo Luciferase Assay System (Promega). Renilla luciferase activity was normalized to the corresponding firefly luciferase activity and plotted as a percentage of the control (cells co-transfected with the corresponding concentration of empty control or vehicle treated cells). Experiments were performed in triplicate wells of a 12-well plate and repeated at least three times.

Cholesterol Efflux Assays

Huh7 cells were seeded at a density of $2\times10^5$ cells per well and transfected with either a control mimic (CM) or miR-27b mimic or miR-148a mimic or a control inhibitor (CI) or miR-148a inhibitor (Inh-148a). Following 48 h of transfection, cells were either loaded with 0.5 μCi/ml $^3$H-cholesterol for 24 h. 12 h after loading, cells were incubated with 3 μM T090 to increase the expression of ABCA1. Then, cells were washed twice with PBS and incubated in DMEM supplemented with 2 mg/ml fatty-acid free BSA (FAFA-media) in the presence of an ACAT inhibitor (2 μmol/L) for 4 h prior to the addition of 50 μg/ml human ApoA1 in FAFA-media with or without the indicated treatments. Supernatants were collected after 6 h and expressed as a percentage of total cell $^3$H-cholesterol content (total effluxed $^3$H-cholesterol+cell-associated $^3$H-cholesterol).

Cellular Cholesterol Measurements

Huh7 cells were seeded at a density of $5\times10^5$ cells/well and transfected with either a control mimic (CM), miR-27b mimic, miR-148a mimic or a control inhibitor (CI), miR-27b inhibitor (Inh-27b), or miR-148a inhibitor (Inh-148a). Following 48 h transfection, cells were incubated with 30 μg/ml nLDL for 2 h. Intracellular cholesterol content was measured using the Amplex Red Cholesterol Assay Kit (Molecular Probes, Invitrogen), according to the manufacturer's instructions.

AAV8-Pre-miR-27b Vector mmu-pre-miR-27 (accession MI000142) was subcloned into an AAV8 vector and its expression was regulated under the control of a liver-specific thyroxine-binding globulin (TBG) promoter, as previously described (Kassim, Li et al. 2013). The AAV8 particles (AAV8.TBG.PI.mir27b.rBG) were generated at the University of Pennsylvania's Penn Vector Core. An empty AAV8 (AAV8.TBG.PI.Null.bGH), also provided by the Penn Vector Core, was used as a control in all experiments.

Mouse Studies

Eight-week-old male C57BL/6 mice were purchased from Jackson Laboratories (Bar Harbor, Me., USA) and kept under constant temperature and humidity in a 12 h controlled dark/light cycle. For miR-27b overexpression studies, mice were randomized into 2 groups: non-targeting AAV8 (AAV-Null, n=10) and pre-miR-27b AAV8 (AAV-27b, n=10). In one set of experiments (see FIG. 7A), mice fed a chow diet were treated once with $5\times10^{12}$ GC/kg AAV-Null (n=5) or $5\times10^{12}$ GC/kg (n=5) in PBS by retro-orbital injection. Blood samples were collected at 0, 2 and 4 weeks after treatment for lipid analysis and lipoprotein profile measurements (see below). Then mice were sacrificed, and hepatic gene expression and liver histology were analyzed (see above). In another set of experiments, mice were challenged with a Western diet [(WD) 9.5% casein, 0.3% DL-Methionine, 15% cornstarch, 40% sucrose, 5% cellulose, 21% anhydrous milk fat, 3.5% mineral mix, 1% vitamin mix, 0.4% calcium carbonate and 0.3% cholesterol] after 4 weeks of treatment with AAV-Null or AAV-27b, as outlined in FIG. 7L. Following 2 weeks of diet, blood was collected for lipid analysis and lipoprotein measurements. Mice were then sacrificed for gene expression analysis and liver histology. All animal experiments were approved by the Institutional Animal Care Use Committee of New York University Medical Center.

For miR-148a inhibition experiments, 8-week old male LDLR−/+;ApoB Tg mice (Taconic) were randomized into 3 groups: LNA control (n=7), LNA anti-miR-148a (n=7) or LNA-anti-miR-27b. Mice received i.p. injections of 5 mg/kg LNA control (5'-ACGTCTATACGCCCA-3'; SEQ ID NO:

51), LNA anti-miR-148a (5'-TTCTGTAGTGCACTG-3'; SEQ ID NO: 52), or LNA anti-miR-27b (5'-AACTTAGC-CACTGTGA-3'); SEQ ID NO: 54) oligonucleotides every three days for a total of two weeks (see FIG. 12A). Twenty-four hours after the final injection, mice were sacrificed and hepatic gene expression analyzed (see above). Blood samples were collected at day 1 and day 14 for lipid analysis (see below).

"Obese" (C57BL/6J-ob/ob) mice were purchased from Jackson Laboratories. In one set of experiments 5 male wild-type and 5 ob/ob mice were studied at 13 weeks of age. In another set of experiments, transgenic mice that overexpress the truncated form of human SREBP1c (amino acids 1-436) in the liver under the control of the PEPCK promoter were used (Shimano, 1997 #222). For these experiments 5 male wild-type and 5 male Tg-SREBP1c were studied at 12-weeks of age. Mice were maintained and sacrificed as previously described (Shimomura, 1999 #221).

For HFD studies, six-week old male C57BL6 (Jackson Laboratories) were placed on a chow diet or HFD containing cholesterol and 21% (wt/wt) fat (from Dyets Inc) for 12 weeks. At sacrifice, mice were fasted for 12-14 h before blood samples were collected by retro-orbital venous plexus puncture. Liver samples were collected and stored at −80° C. and total RNA was harvested for miRNA and gene expression analysis.

Plasma Lipid Analysis and Lipoprotein Profile Measurements

In the chow diet studies, mice were fasted for 12-14 h before blood samples were collected by retro-orbital venous plexus puncture. Plasma was separated by centrifugation and stored at −80° C. Total plasma cholesterol and HDL-cholesterol were enzymatically measured with the Cholesterol Assay Kit (Wako Diagnostics), according to the manufacturer's instructions. Total triglycerides were measured with the Wako Diagnostics Triglycerides Reagent. The lipid distribution in plasma lipoprotein fractions was assessed by fast-performance liquid chromatography (FPLC) gel filtration with 2 Superose 6 HR 10/30 columns (Pharmacia). Cholesterol in each fraction was enzymatically measured using the Amplex Red Cholesterol Assay Kit (Molecular Probes, Invitrogen). In another set of experiments, mice were fed with a WD for 2 weeks and blood samples were collected in non-fasting and fasting (3 h) conditions. Lipid analysis and lipoprotein fractionation were performed as described above.

Statistics

All data are expressed as mean SEM. Statistical differences were measured using either an unpaired Student's t test or 2-way ANOVA with Bonferroni correction for multiple comparisons when appropriate. A value of $P \leq 0.05$ was considered statistically significant. Data analysis was performed using GraphPad Prism Software Version 5.0a (GraphPad, San Diego, Calif.). *$P \leq 0.05$.

Results

Primary miRNA Screen Design and Optimization

Figure 8:
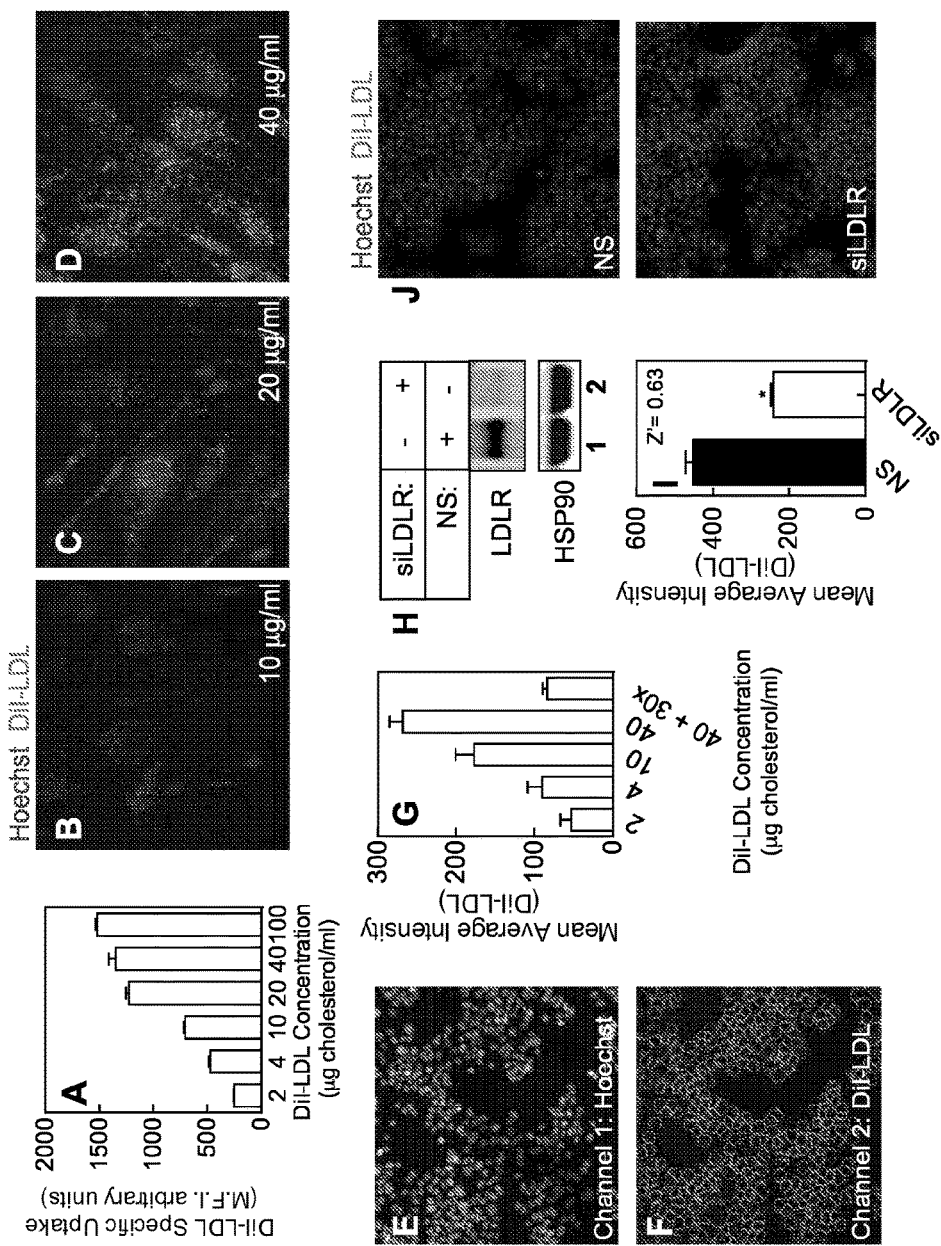
FIGS. 8A-J. Optimization of primary miRNA screen, Related to FIG. 1. (A) Flow cytometry analysis of DiI-LDL uptake in Huh7 cells incubated with varying concentrations of DiI-LDL (2-100 μg/ml) for 8 h at 37° C. (B-D) Representative images of DiI-LDL uptake in Huh7 cells incubated with 10 μg/ml (B), 20 μg/ml (C) and 40 μg/ml (D) DiI-LDL. Following 8 h incubation at 37° C., cells were washed, fixed, and stained with Hoechst; DiI-LDL staining is represented by darker grey, and stained nuclei are in darkest grey. (E and F) Representative images of cell segmentation used to quantify DiI-LDL uptake in a high-throughput format. Huh7 cells were incubated with 30 μg/ml DiI-LDL for 8 h at 37° C. Following this, cells were washed, fixed, counterstained with Hoechst, and imaged using the Cellomics ArrayScan. DiI-LDL uptake was quantified using the Cellomics Target Activation BioApplication. (G) Mean average intensity of DiI-LDL in Huh7 cells incubated with varying concentrations of DiI-LDL (2-40 μg/ml) in 384-well plates. Following incubation for 8 h at 37° C., cells were washed, fixed, stained, and imaged using the Cellomics ArrayScan. In certain wells, cells were incubated with 40 μg/ml DiI-LDL+ 30× unlabeled native LDL (nLDL) to show specificity of DiI-LDL uptake/quantification. (H) Western blot analysis of LDLR in Huh7 cells transfected with nonsilencing (NS) control siRNA or siRNA LDLR (siLDLR). HSP90 was used as a loading control. (I) Mean average intensity of DiI-LDL in Huh7 cells transfected with non-silencing (NS) control siRNA or siRNA LDLR (siLDLR) and incubated with 30

To systematically identify miRNAs that regulate LDLR activity, the present inventors developed an automated, high-throughput microscope-based screening assay that monitored the effect of miRNA overexpression on DiI-LDL uptake in human hepatic (Huh7) cells. In order to avoid confounding effects of lipoproteins in the media, the present inventors initially characterized the specific uptake of DiI-LDL in Huh7 cells incubated in 10% lipoprotein deficient serum (LPDS). To this end, the changes in LDLR activity were analyzed in Huh7 cells treated with increasing concentrations of DiI-LDL for 8 h. The cell-associated DiI-fluorescence was determined at the end of the incubation period by flow cytometry. As seen in FIGS. 8A-D, DiI-LDL uptake kinetics were saturable and showed complete saturation at approximately 20-40 µg/ml DiI-LDL cholesterol, which is in accordance with the well-known kinetic properties of the LDLR (Brown, Dana et al. 1973, Goldstein, Basu et al. 1976). Similar results were observed when cells were cultured in 384-well plates and fluorescence intensity was measured with automated fluorescent microscopy (FIGS. 8E-G). Importantly, LDL uptake was specific, as DiI accumulation was displaced when cells were incubated in the presence of 30× unlabeled LDL (FIG. 8G). The inventors further analyzed whether this system was suitable for functional genomic studies by assessing LDLR gene inactivation by RNA interference (RNAi). As expected, treatment of Huh7 cells with siRNA LDLR (siLDLR) significantly reduced LDLR expression at the protein level (FIG. 8E). Consistent with this, DiI-LDL uptake was also diminished in siLDLR-treated Huh7 cells compared to cells transfected with a non-silencing (NS) control siRNA (FIG. 8I-J). Importantly, the z-factor was determined to be greater than 0.5 (FIG. 8I, inset), indicative of a robust setup for our screen (Zhang, Chung et al. 1999).

Identification of miRNAs that Regulate LDLR Activity in Human Hepatic Cells

For the genome-wide miRNA screen, Huh7 cells were reverse transfected in triplicate with a library of 1719 distinct miRNAs (Life Technologies mirVana Mimic Library, miRBase release 17.0) and incubated with 30 µg/ml DiI-LDL cholesterol. Following 8 h of incubation, cells were washed, fixed and stained with Hoechst to distinguish nuclei (FIG. 1A, upper panel). In addition to internal controls on each screening replicate (see Methods), previously validated siRNAs against the LDLR and a non-silencing (NS) control siRNA were used as positive and negative controls, respectively (FIGS. 8H-J). Mean average intensity of DiI-LDL was determined on an individual cell basis (FIG. 1A, middle panel) using automated high-content image analysis software. To standardize measurements from different plates, phenotypic effects of each miRNA (i.e. those that increased or decreased average DiI intensity) were converted to robust Z-scores (Birmingham, Selfors et al. 2009) based on the median average intensity of each array plate. Notably, comparison of plate replicates (FIGS. 1B-D) and internal plate controls (FIG. 1E) suggested high reproducibility of the screen. Upon normalization, robust Z-scores for each individual miRNA were ranked and compared to their respective plate replicates (Table 2). While our screen identified miRNAs that both increased and decreased LDL uptake, the present inventors chose to focus on those miR-NAs whose overexpression decreased receptor activity, as pharmacological inhibitors of this miRNA subset represent potential therapeutic targets to lower LDL-cholesterol levels.

Given the propensity for off-target effects in high-throughput screening assays, a multi-step system was designed in order to narrow down candidates; specifically, miRNAs were subjected to five screening passes before chosen for further validation (FIG. 1A, lower panel). In the first pass, miRNAs were considered putative regulators of LDLR activity for which two or more replicate miRNAs yielded activities smaller than 0.8 median absolute deviations (MAD) away from plate medians (deviation ≤−0.8) (FIG. 1F). Although this criterion is less stringent than most cut-offs for high-throughput screenings (Birmingham, Selfors et al. 2009), this pass was designed to yield a significantly higher hit rate (423 miRNAs, ~25% of miRNAs screened) to allow for subsequent passes (Table 2). To minimize the risk of identifying false positives, the selection of miRNAs for follow-up evaluation in the ensuing passes was based on several criteria. Specifically, miRNAs were chosen for further validation if they: 1) had conserved predicted binding sites in the 3'UTR of the LDLR, 2) were highly expressed in human and mouse liver, 3) were modulated by dietary lipids, and 4) had high liver activity (i.e. high miRNA expression versus reduced target gene expression) (FIG. 1A, bottom panel and Table 1). Out of the 423 miRNAs identified from the initial pass, miR-27b and miR-148a (~0.1% of miRNAs screened) emerged as the most obvious and strongest positive hits, showing reduced LDLR activity (TargetScan v6.2, www.targetscan.org), conserved predicted binding sites in the 3'UTR of the LDLR, medium to high expression in human and mouse hepatic tissue (Barad, Meiri et al. 2004, Landgraf. Rusu et al. 2007, Vickers. Shoucri et al. 2013) and high liver activity (Arora and Simpson 2008). In addition, both of these miRNAs have previously been shown to be upregulated in the livers of mice fed a high fat diet (HFD) [(Vickers, Shoucri et al. 2013) Table 1], suggesting a possible physiological role for miR-27b and miR-148a in regulating lipid metabolism and therefore, highlighting them for further validation.

miR-27b and miR-148a are Regulated by Hepatic Lipid Content and Enriched in Lipid Metabolism Target Genes miR-27b is a member of the miR-23b~27b~24-1 miRNA cluster encoded within the intron of the alanine aminopeptidase gene (APO) on human chromosome 9 (FIG. 2A). The mature miRNA sequences of miR-23b, miR-27b and miR-24 are conserved among vertebrate species (FIG. 2A, lower panels). miR-148a is also highly conserved in vertebrates, however it is encoded within an intergenic region of human chromosome 7 (FIG. 2B). Dietary lipids regulate the hepatic expression of both miRNAs (FIG. 2C-P). Specifically, the expression levels of the mature and precursor forms of miR-27b and miR-148a (pri-, pre- and mature) were increased in mice and non-human primates fed a high-fat diet (HFD) compared to those fed a chow diet (FIG. 2I-P). Consistent with our in vivo observations, the mature and precursor forms of miR-27b and miR-148a were also significantly upregulated in Huh7 cells treated with 120 μg/ml native LDL (nLDL) (FIG. 2C-H). Furthermore, the mature form of miR-148a was also significantly upregulated in the livers of ob/ob mice (FIG. 2Q). Taken together, these results demonstrate the regulation of the miR-148a and miR-27b transcript by dietary lipids.

To gain insight into the function of miR-27b and miR-148a in regulating cholesterol homeostatsis (and more specifically, LDLR activity), their potential targets were analyzed using a rigorous bioinformatic algorithm (Mercer, Snijder et al. 2012). For this, predicted targets identified in three target-prediction websites (Targetscan, miRWalk, and miRanda) were assigned to functional annotation clusters using the public database, DAVID [http://david.abbc.ncifcr-f.gov (Huang da, Sherman et al. 2009)]. As shown, miR-27b and miR-148a target genes were enriched (E≥1.0) within 77 and 78 clusters, respectively, and several annotation networks. The functional cluster analysis was combined with data on protein-protein interactions between individual target genes enriched in lipid metabolism using the STRING v9 (Szklarczyk, Franceschini et al. 2011) and PANTHER databases (Thomas, Campbell et al. 2003). The results of this bioinformatic analysis are visually shown in FIG. 9 and indicate that both miRNAs target a vast network of lipid metabolism regulators, including LDLR, LDLRAP1, and ABCA1.

Further characterization of the aforementioned target genes revealed that miR-27b has one predicted binding site in the 3'UTR of LDLR and two predicted binding sites in the 3'UTR of LDLRAP1 and ABCA1 (FIG. 3A). miR-148a has two predicted binding sites in the 3'UTR of LDLR and one predicted binding site in the 3'UTR of ABCA1 (FIG. 3B). Notably, most of the miR-27b and miR-148a predicted binding sites are conserved between mammals (FIGS. 10A and 10B). As expected, 3'-UTR luciferase reporter assays revealed that the LDLR, LRLRAP1 and ABCA1 are directly regulated by miR-27b (FIG. 3C). Importantly, mutations of miR-27b target sites relieved miR-27b repression of LDLR, LRLRAP1 and ABCA1 3'UTR activity, consistent with a direct interaction of miR-27b with these sites (FIG. 3C). Similar to miR-27b, overexpression of miR-148a inhibited LDLR and ABCA1 3'UTR activity and specific point mutations in the predicted binding sites abolished this inhibitory effect (FIG. 3D). Together, these experiments identify the LDLR and ABCA1 as direct targets for both miR-27b and miR-148a, whereas ABCA1 and LDLRAP1 are direct targets of miR-27b only. As such, both of these miRNAs represent particularly useful targets to alter plasma levels of LDL and HDL cholesterol.

miR-27b and miR-148a Inhibit LDLR Expression and Regulate LDLR Activity

Figure 11:
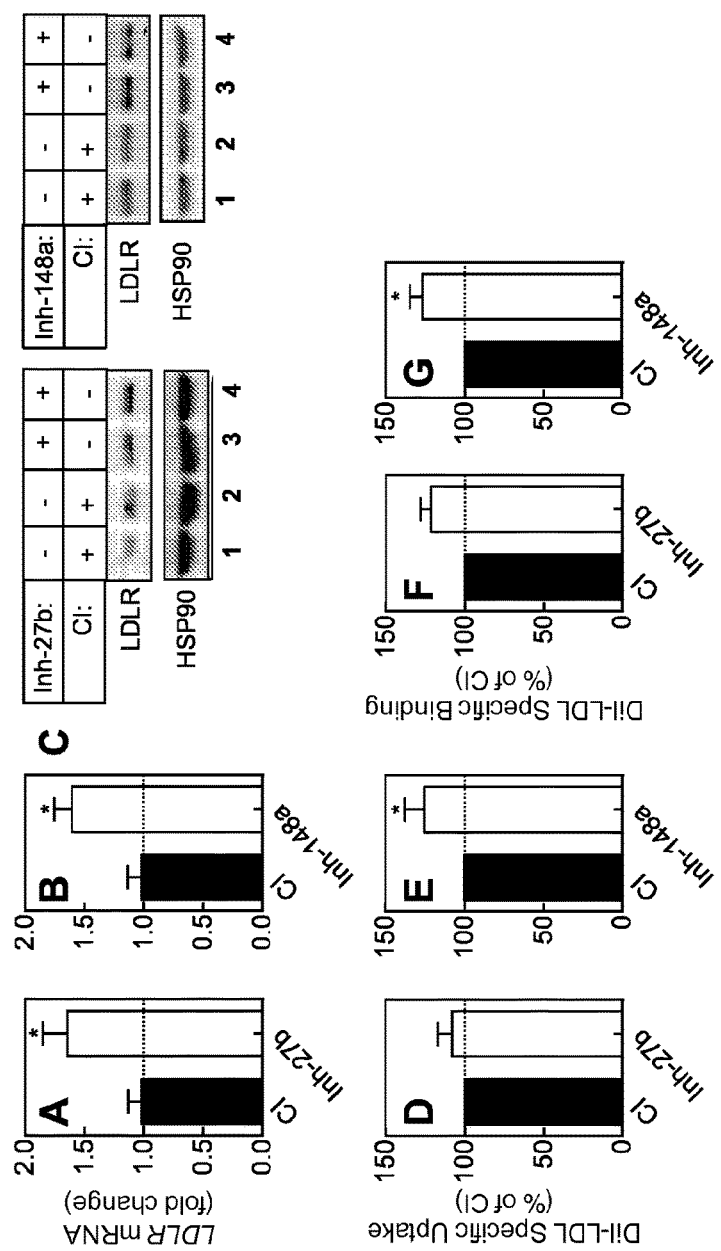

The effect of miR-27b and miR-148a overexpression and inhibition on LDLR mRNA and protein expression was determined next. Transfection of Huh7 cells with miR-27b and miR-148a, but not a control mimic (CM) significantly decreased LDLR mRNA and protein levels (FIGS. 4A and 4B). Conversely, inhibition of endogenous miR-27b and miR-148a increased the expression of the LDLR (FIGS. 4D and 4E). Similar results were observed in mouse hepatic cells (Hepa) transfected with antisense inhibitors of miR-27b (Inh-27b) and miR148a (Inh-148a) (FIGS. 11A-C). In addition, miR-27b also regulated the expression of LDL-RAP1 in Huh7 cells (FIGS. 4C and 4F), suggesting that this miRNA might control LDLR activity by direct targeting of the LDLR and by regulating its endocytosis.

Figure 5:
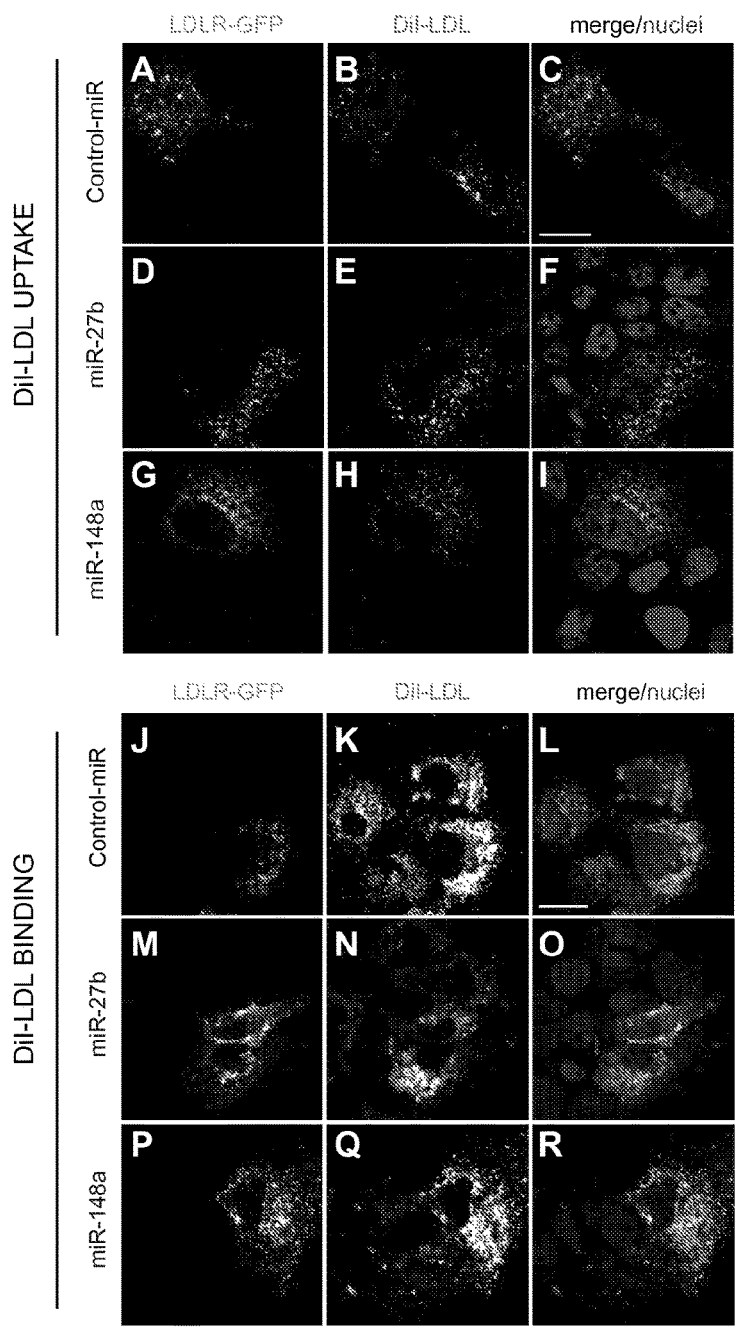
FIG. 5A-R. LDLR-GFP overexpression rescues LDLR activity in miR-27b- and miR-148a-transfected cells. (A-I) Huh7 cells were cotransfected with LDLR-GFP and a control mimic (CM, A-C), miR-27b mimic (D-F), or miR-148a mimic (G-I) and incubated with 30 μg/ml DiILDL for 2 h at 37° C. Following incubation, cells were washed, fixed and stained with TOPRO. In all panels, LDLR staining is represented by light grey, DiI-LDL staining is represented by darker grey, and stained nuclei are in darkest grey. Scale bar, 10 μm. (J-R) Huh7 cells were co-transfected with LDLR-GFP and a control mimic (CM, J-L), miR-27b mimic (M-O), or miR-148a mimic (PR) and incubated with 30 μg/ml DiI-LDL for 90 min at 4° C. Following incubation, cells were washed, fixed and stained with TOPRO. Scale bar, 10 μm. In panels (A) through (R), images are representative of ≥3 experiments that gave similar results.
Figure 6:
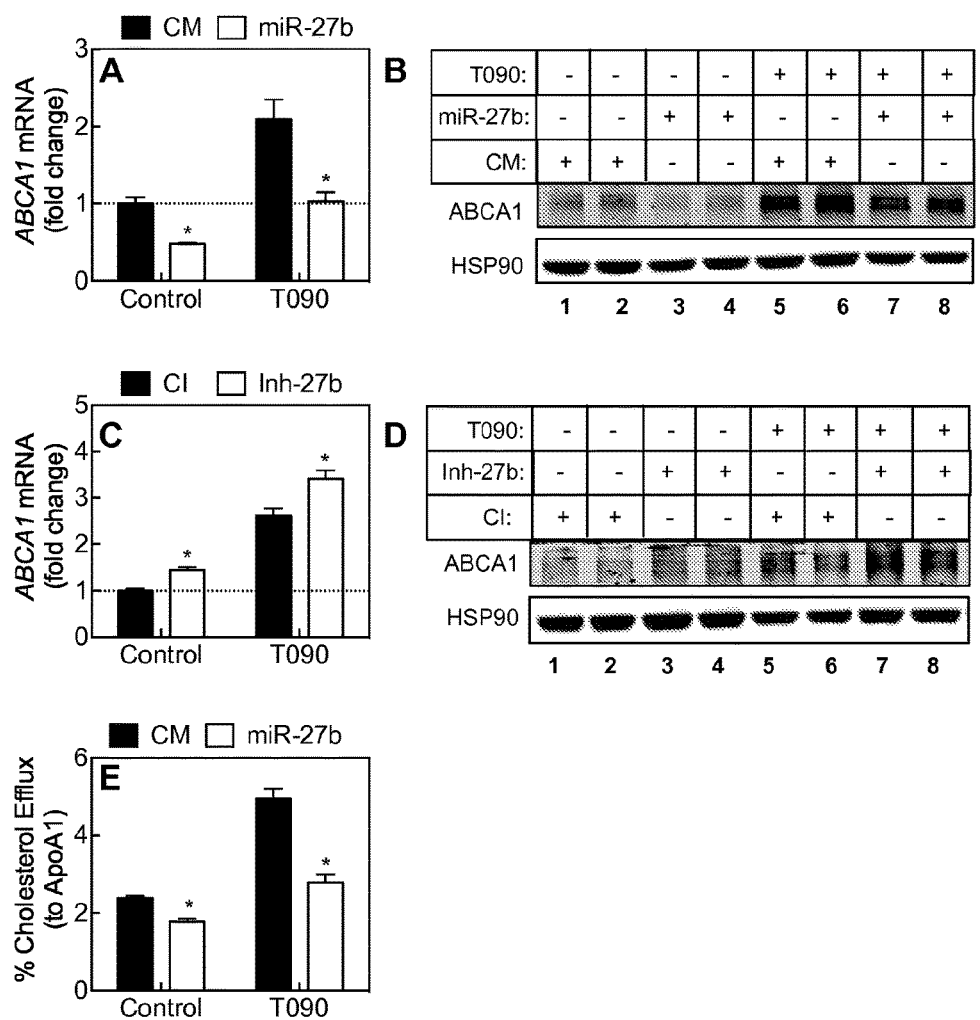
FIGS. 6A-E. miR-27b represses ABCA1 expression and regulates cholesterol efflux in human hepatic cells. (A) qRT-PCR analysis of ABCA1 expression in Huh7 cells transfected with a control mimic (CM) or miR-27b mimic in the absence or presence of T0901317 (T090). (B) Western blot analysis of ABCA1 expression in Huh7 cells transfected with a control mimic (CM) or miR-27b mimic in the absence or presence of T0901317 (T090). HSP90 was used as a loading control (C) qRT-PCR analysis of ABCA1 expression in Huh7 cells transfected with a control inhibitor (CI) or miR-27b inhibitor (Inh-27b) in the absence or presence of T0901317 (T090). (D) Western blot analysis of ABCA1 expression in Huh7 cells transfected with a control inhibitor (CI) or miR-27b inhibitor (Inh-27b) in the absence or presence of T0901317 (T090). HSP90 was used as a loading control. (E) Cholesterol efflux to ApoA1 in Huh7 cells transfected with a control mimic (CM) or miR-27b mimic and stimulated with T0901317 (T090). In panels (A) through (E) data are the mean±SEM and representative of ≥2 experiments in triplicate. *, P≤0.05 compared to cells transfected with CM within each treatment group (A. E). *, P≤0.05 compared to cells transfected with CI within each treatment group (C).
Figure 7:
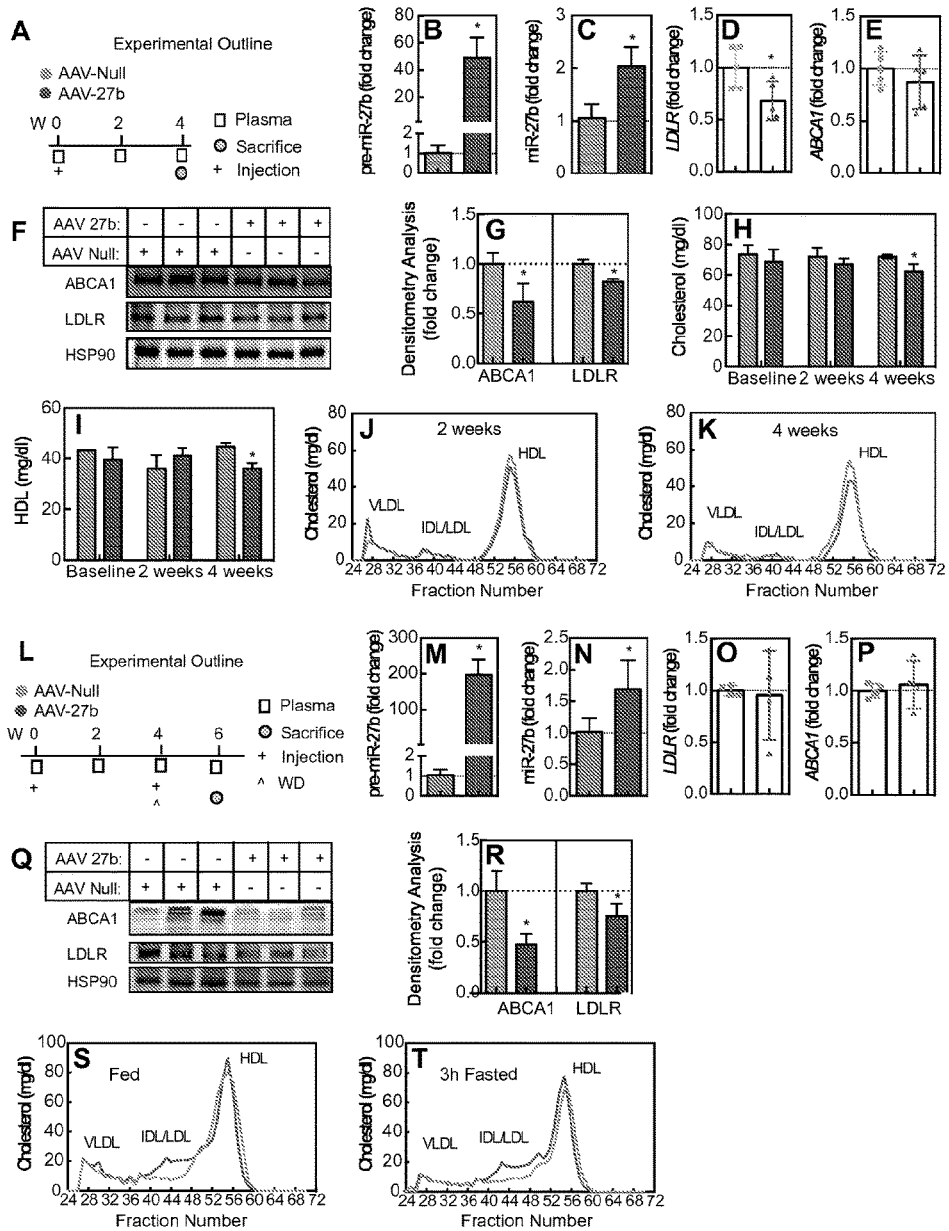
FIGS. 7A-T. miR-27b regulates plasma LDL and HDL levels in vivo. (A) Experimental outline of AAV-Null and AAV-pre-miR-27b (AAV-27b) treated mice (n=5 per group) fed a chow diet. (B and C) qRT-PCR analysis of pre-miR-27b (B) and miR-27b (C) levels in the livers of mice following 4 weeks treatment. *, P≤0.05 compared to AAV-Null treated mice. (D and E) qRT-PCR analysis of LDLR expression (D) and ABCA1 expression (E) in the livers of mice following 4 weeks treatment. *, P≤0.05 compared to AAV-Null treated mice. (F and G) Western blot analysis of LDLR and ABCA1 expression in the livers of mice following 4 weeks treatment. HSP90 was used as a loading control. Quantification of blot relative to HSP90 is shown in (G). Numbers are represented as fold-change compared to AAV-Null treated mice, *, P≤0.05. (H and I) Levels of total cholesterol (H) and HDL cholesterol (I) in the plasma of mice treated with AAV-Null or AAV-27b for 0, 2, and 4 weeks. *, P≤0.05 compared to AAV-Null treated mice within each treatment week. (J and K) Cholesterol content of FPLC-fractionated lipoproteins following 2 (J) and 4 weeks (K) of treatment with AAV-Null or AAV-27b. (L) Experimental outline of AAV-Null and AAV-pre-miR-27b (AAV-27b) treated mice (n=5 per group). Four weeks after the initial treatment, mice were injected a second time with AAV-Null or AAV-27b and challenged with a Western diet (WD) for the following 2 weeks. (M and N) qRT-PCR analysis of pre-miR-27b (M) and miR-27b (N) levels in the livers of mice following 6 weeks treatment. *, P≤0.05 compared to AAV-Null treated mice. (O and P) qRT-PCR analysis of LDLR expression (O) and ABCA1 expression (P) in the livers of mice following 6 weeks treatment. *, P≤0.05 compared to AAV-Null treated mice. (Q and R) Western blot analysis of LDLR and ABCA1 expression in the livers of mice following 6 weeks treatment. HSP90 was used as a loading control. Quantification of blot relative to HSP90 is shown in (R). Numbers are represented as fold-change compared to AAV-Null treated mice, *, P≤0.05. (S and T) Post-prandial (fed) and fasting (3 h) cholesterol content of FPLC-fractionated lipoproteins following 6 weeks treatment. In panels (B) through (E), (G) through (I), (M through P) and (R) data are the mean±SEM.

Defective hepatic LDLR activity results in elevated levels of LDL in the blood and is associated with an increased risk of atherosclerosis and coronary heart disease (Lusis 2000, Glass and Witztum 2001). To assess the role of miR-27b and miR-148a in regulating LDL uptake in human hepatic cells and to confirm findings from the primary screen, miR-27b and miR-148a were overexpressed or inhibited and DiI-LDL uptake and binding were assessed by flow cytometry. Transfection of Huh7 cells with miR-27b and miR-148b attenuated LDL specific uptake (FIGS. 4G-H) and binding (FIGS. 4I-J). Consistent with the inhibitory effect of miR-27b and miR-148a on LDLR activity, transfection of both miRNAs significantly reduced intracellular cholesterol concentration after incubation with nLDL (FIGS. 4K-L). Importantly, antagonists of endogenous miR-27b (Inh-27b) and miR-148a (Inh-148a) increased LDL uptake and binding in Huh7 (FIGS. 4M-P) and Hepa cells (FIGS. 11D-G). Intracellular cholesterol levels were also slightly, but significantly, increased in Huh7 cells overexpressing inhibitors of miR-27b (Inh-27b) and miR-148a (Inh-148a) (FIGS. 4Q-R). Additionally, when LDLR-antibody internalization and DiI-LDL uptake were analyzed by immunofluorescence, reduced LDLR internalization and a concomitant decrease in DiI-LDL uptake were observed in cells overexpressing miR-27b and miR-148a compared to controls (FIG. 4S). The inventors next determined whether the effect of miR-27b and miR-148a in regulating LDL uptake was rescued by overexpressing a LDLR-GFP cDNA construct that lacked the 3'UTR, thereby resistant to miR-27b and miR-148a inhibitory action. As previously shown in FIG. 4S, Huh7 cells transfected with miR-27b or miR-148a have a significant reduction in DiI-LDL uptake and binding when analyzed by immunofluresecnce (FIG. 5A-R). However, this effect was abrogated in cells that expressed the LDLR-GFP construct, suggesting that miR-27b and miR-148a regulate DiI-LDL uptake and binding by direct down-regulation of the LDLR (FIG. 5A-R). Thus, manipulation of cellular miR-27b and miR-148a alters LDLR activity, a critical step in controlling the levels of atherogenic lipoproteins in the blood.

miR-27b Regulates ABCA1 Expression and Cholesterol Efflux in Human Hepatic Cells ABCA1 µlays a major role in regulating cholesterol efflux from macrophages to ApoA1 and in the biogenesis of HDL in the liver, thereby controlling reverse cholesterol transport (RCT), a process that mediates the clearance of cholesterol from peripheral cells to the liver for excretion to the bile and feces (Oram and Vaughan 2000). To assess whether miR-27b regulates ABCA1 expression and cholesterol efflux from human hepatic cells, Huh7 cells were transfected with miR-27 mimics (miR-27b) or miR-27 antisense oligonucleotides (Inh-27b) and analyzed ABCA1 mRNA and protein levels and cholesterol efflux to ApoA1. As seen in FIG. 6A, miR-27 overexpression strongly reduced ABCA1 mRNA expression in basal conditions (control) and when cells were pre-treated with the LXR ligand T0901317 [(T090) (to directly stimulate ABCA1 expression)]. Similar effects were observed at the protein level (FIG. 6B). Most importantly, endogenous inhibition of miR-27b in human hepatic cells increased ABCA1 mRNA and protein levels (FIGS. 6C and 7D). In agreement with the known cellular functions of ABCA1, transfection of Huh7 cells with miR-27b significantly attenuated cholesterol efflux to ApoA1 (FIG. 6E).

miR-27b Levels Regulate Circulating LDL and HDL Cholesterol in Mice

Because miR-27b alters both LDL uptake and cholesterol efflux in human hepatic cells, the functional contribution of increased miR-27b levels on plasma lipids were next assessed in mice fed a chow or Western Diet (WD). To specifically alter miRNA expression in the liver, an adeno-associated virus serotype 8 (AAV8) vector encoding pre-miR-27b (AAV-27b) or a control vector (AAV-Null) were used. AAV8 vectors have previously been evaluated for liver directed gene transfer in murine models and show no signs of liver toxicity (Wang, Wang et al. 2010, Kassim, Li et al. 2013). For the chow diet studies, AAV-Null or AAV-27b vectors ($5 \times 10^{12}$ GC/kg) were delivered to 8-week old male C57BL/6 mice (n=5 per group) via retro-orbital injection; plasma lipids were measured after two and four weeks (FIG. 7A). To determine the efficacy of miR-27b over-expression, the expression of hepatic miR-27b and its target genes were measured after four weeks of treatment. As expected, pre-miR-27b expression levels were significantly higher in mice treated with AAV-27b compared to mice treated with AAV-Null (FIG. 7B). Similarly, the expression levels of mature miR-27b were also upregulated in mice injected with AAV-27b, but modestly when compared to pre-miR-27b levels (FIG. 7C). Consistent with our in vitro results, hepatic LDLR expression was significantly decreased in mice treated with AAV-27b (FIG. 7D), however no significant changes in ABCA1 mRNA were observed (FIG. 7E). Notably, both LDLR and ABCA1 protein levels were significantly reduced in the livers of mice treated with AAV-27b compared to those treated with AAV-Null (FIG. 7F-G). Given that decreased hepatic expression of ABCA1 would be predicted to reduce HDL biogenesis, circulating total and HDL-C levels were next measured in mice treated with AAV-Null or AAV-27b after over-night fasting. As expected, in vivo over-expression of miR-27b resulted in a progressive decline of total plasma HDL and cholesterol compared to controls (FIG. 7H-I). Consistent with this, analysis of lipoproteins by FPLC showed a prominent decrease in cholesterol content of the HDL fractions in mice treated with miR-27b for two and four weeks (FIG. 7J-K). Surprisingly, hepatic over-expression of miR-27b did not alter cholesterol content in the IDL/LDL fractions, despite decreased levels of the LDLR (FIG. 7J-K). Moreover, no significant differences in plasma triglycerides were observed (data not shown).

Because the rate of hepatic LDL-clearance is 40-fold greater in C57BL/6 mice than in humans (Dietschy, Turley et al. 1993), the efficacy of miR-27b over-expression on plasma lipids were further determined in mice challenged with a WD after four weeks of miR-27b treatment (FIG. 7L). Similar to mice fed a chow diet, hepatic levels of pre-miR-27b and mature miR-27b were significantly increased (FIG. 7M-N), while ABCA1 and LDLR protein expression were decreased (FIG. 7Q-R). No significant differences were observed in ABCA1 and LDLR mRNA levels (FIG. 7O-P). Next, post-prandial and fasting (3 h) plasma lipid levels were analyzed in mice treated with AAV-27b or AAV-Null. Fractionation of plasma lipoproteins revealed that IDL/LDL cholesterol was markedly increased in mice over-expressing miR-27b (FIG. 7S-T). Interestingly, no differences were observed in the HDL-cholesterol fraction in either the fed or fasted state (FIG. 7S-T), despite a striking down-regulation of ABCA1 in AAV-miR-27b treated mice. Taken together, these results suggest that manipulation of miR-27b levels in vivo alters LDLR and ABCA1 expression and plasma LDL and HDL cholesterol levels.

Modulation of miR-27b and miR-148a Expression Regulates LDLR Expression In Vivo

Figure 13:
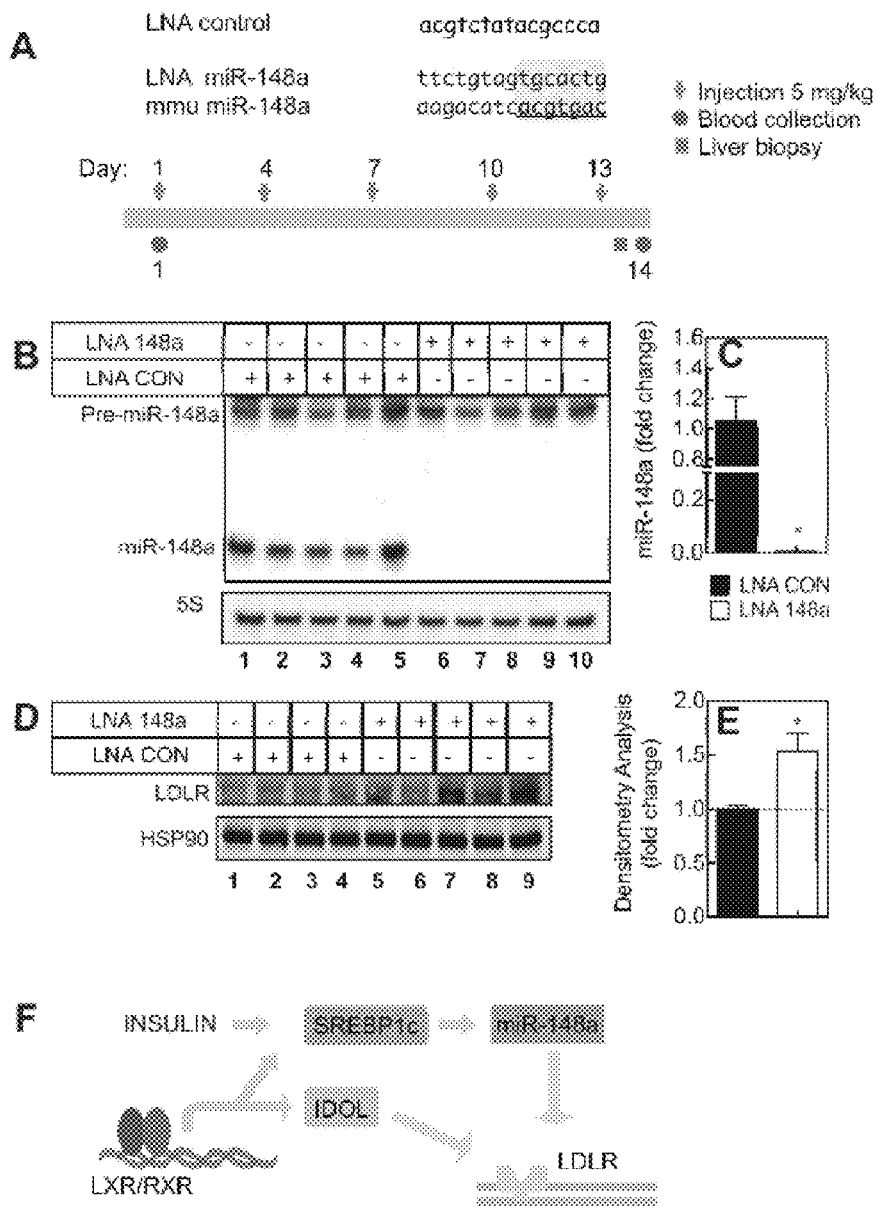
Figure 14:
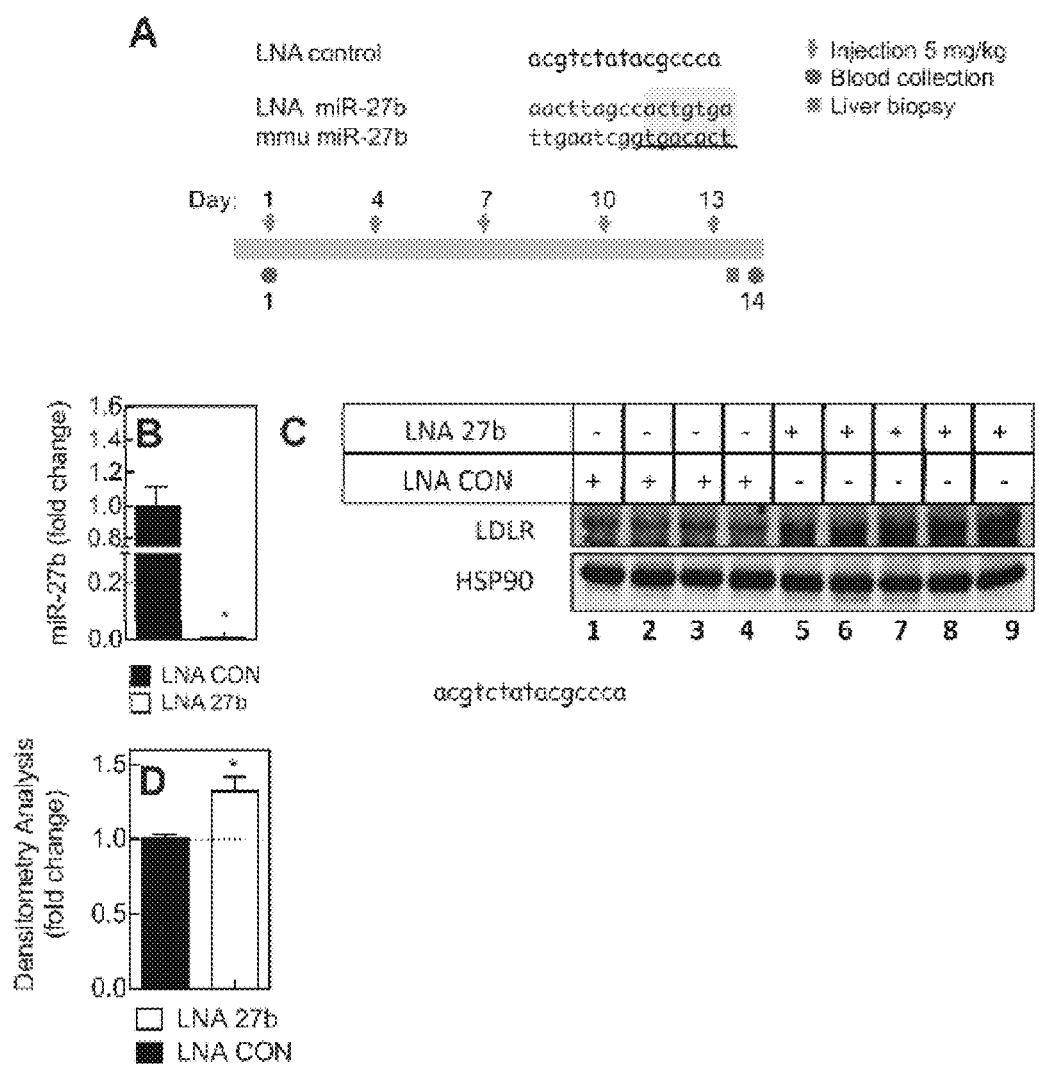

To ascertain the endogenous role of miR-27b and miR-148a in regulating LDLR expression and activity in vivo, miR-148a expression was inhibited using locked nucleic acid (LNA) miRNA inhibitors (primer sequences were 5'-TTCTGTAGTGCACTG-3' [SEQ ID NO: 52] and 5'-AACTTAGCCACTGTGA-3' [SEQ ID NO: 54]) (Exiqon). Because LDL levels in wild-type mice plasma are low (Dietschy, Turley et al. 1993), "humanized" mice (LDLR−/+;ApoBTg background) were used for the studies (Purcell-Huynh 1995). To inhibit hepatic miR-27b and miR-148a expression, mice were intraperitoneally injected every three days for a period of two weeks with 5 mg/kg of DNA/LNA mixmer antisense oligonucleotides against miR-148a (LNA 148a) or miR-27b (LNA 27b) (FIGS. 13A and 14A). A scrambled LNA oligonucleotide (LNA CON, 5'-ACGTCTATACGCCCA-3'; SEQ ID NO: 51) was used as a control. Twenty-four hours following the last injection, mice were sacrificed and serum and livers collected for plasma cholesterol and gene expression analysis, respectively. As expected, treatment with LNA anti-miR-148a (LNA 148a, 5'-TTCTGTAGTGCACTG-3'; SEQ ID NO: 52) and LNA anti-miR-27b (LNA 27b, 5'-AACTTAGCCACT-GTGA-3'; SEQ ID NO: 54) significantly reduced levels of hepatic miR-148a and miR-27b (FIGS. 13B-C and 14B). Importantly, and consistent with this, hepatic protein levels of LDLR were significantly increased in LNA 148a and LNA 27b treated mice compared to controls (FIGS. 13D-E and 14C-D). Further experiments are necessary to determine whether the anti-miR-27b or anti-miR-148a-induced expression of LDLR plays a functional role in decreasing levels of LDL-cholesterol. Nevertheless, taken together, these results suggest a physiological role for miR-148a in controlling hepatic LDLR expression in vivo.

Transcriptional Regulation of miR-148a by SREBP1c

Given that miR-148a is upregulated in the livers of ob/ob and high-fat-diet (HFD) fed mice, the present inventors next sought to determine how this intergenic miRNA is transcriptionally regulated. Previous reports have identified several transcriptional start sites (TSSs) located ~1.1 to ~1.6 kb upstream of the miR-148a sequence (Eponine, miRstart source) (Saini 2007). Importantly, these TSSs correlate with CpG islands and H3K4Me3 marks (Ernst 2010, Monteys 2010). Furthermore, upstream regions adjacent to the putative TSSs revealed active and weak promoter and enhancer regions involved in the regulation of miR-148a expression (FIG. 12A) (Ernst 2010). Intriguingly, a SREBP1 binding site was previously identified in this active promoter region using ChIP-seq (Gerstein 2012). The present inventors reasoned that SREBP1c, the predominant isoform of SREBP1 in the liver (Horton 2002), might be a transcriptional regulator of miR-148a expression. Therefore, to test whether SREBP1c could modulate miR-148a expression in vitro, Huh7 cells were transfected with a vector expressing FLAG-tagged nuclear SREBP1c (nSREPB1c) and miR-148a expression was measured by qRT-PCR. As shown in FIG. 12B-D, overexpression of nSREBP1c significantly increased the expression of miR-148a (mature and precursor forms), as well as the SREBP1c target gene, FASN, thereby suggesting that SREBP1c may regulate miR-148a expression by binding to its promoter. To further explore the in vivo relevance of SREBP1c-dependent regulation of miR-148a, the mature form of miR-148a was next measured in the livers of mice overexpressing a truncated form of human SREBP1c (Shimano 1997). qRT-PCR analysis showed that miR-148a was increased in the livers of SREBP1c transgenic (SREBP1c-Tg) mice compared to controls (FIG. 12E), corroborating the above in vitro findings that miR-148a is regulated by nSREBP1c.

The induction of hepatic SREBP1c is dependent on LXR agonists (Bobard 2005). Therefore, to determine whether miR-148a expression is affected by modulation of endogenous SREBP1c, mouse primary hepatocytes were treated with T090, a synthetic LXR-ligand, and miR-148a expression was assessed by qRT-PCR and Northern blotting. As shown in FIG. 12F, the expression of several LXR-regulated genes, including ABCA1, SREBP1c, and FASN were all significantly upregulated upon LXR-activation compared to vehicle-treated cells. Importantly, the precursor and mature forms of miR-148a were also induced by T090 treatment (FIGS. 12G-H). As insulin is the major activator of SREBP1c in the liver, the present inventors further validated whether miR-148a expression is affected by the insulin-mediated induction of SREBP1c. As seen in FIG. 12I, insulin treatment significantly upregulated FASN and SREBP1c expression in primary mouse hepatoctytes. Importantly, pre-miR-148a and miR-148a expression were also significantly increased in insulin-treated cells (FIGS. 12J-K). Furthermore, the inventors found that miR-148a promoter activity was induced in Hela cells overexpressing nuclear SREBP1c and Huh7 cells treated with insulin or T090 (FIGS. 12L-N). Collectively, these results demonstrate that activation of hepatic SREBP1c by LXR and insulin correlates with endogenous miR-148a expression. Thus, miR-148a may define a novel SREBP1c-dependent axis for regulating LDLR expression.

DISCUSSION

This example provides the identification of miRNAs that control LDLR activity. Amongst them, the inventors have characterized the role of miR-27b and miR-148a in regulating LDLR expression and activity. Both miRNAs are highly expressed in the liver and are regulated by hepatic lipid content. Mechanistically, it is disclosed herein that the aforementioned miRNAs directly target and inhibit the expression of the LDLR, thereby reducing LDL uptake in human hepatic cell lines. Moreover, miR-27b also regulates ABCA1 expression and cellular cholesterol export. Importantly, overexpression of miR-27b in mice increases plasma LDL-C and reduces circulating HDL-C, thus suggesting that antagonists of endogenous miR-27b may be useful as a therapeutic strategy for enhancing LDLR and ABCA1 expression. Indeed, when the inventors inhibited miR-27b expression using LNA antisense oligonucleotides, hepatic LDLR expression was significantly increased. In addition, miR-148a contains a SREBP1 binding site in its promoter region. Accordingly, induction of SREBP1c by overexpression constructs and by the LXR agonist, T090, and insulin increases miR-148a promoter activity and expression, thus defining a complementary pathway for controlling cholesterol uptake. Importantly, inhibition of miR-148a in mice increases hepatic LDLR expression, suggesting that antagonists of endogenous miR-148a may be useful as a therapeutic strategy for increasing LDLR activity and ultimately reducing levels of LDL-C.

Although several miRNAs, including miR-33, miR-144, miR-758 and miR-106b, have been shown to regulate ABCA1 and plasma HDL-C levels (Krutzfeldt, Rajewsky et al. 2005, Esau, Davis et al. 2006, Najafi-Shoushtari, Kristo et al. 2010, Ramirez, Davalos et al. 2011, Rayner, Esau et al. 2011, Kim, Yoon et al. 2012, de Aguiar Vallim, Tarling et al. 2013, Ramirez, Rotllan et al. 2013), little is known about miRNAs that control the expression of the LDLR and modulate LDL-C levels. To date, only the liver-restricted miR-122 has been shown to play a direct role in LDL cholesterol metabolism. Specifically, studies by Esau et al. and Elmen et al. have shown that antisense targeting of miR-122 in mice significantly reduces total plasma cholesterol and triglyceride levels, as well as hepatic steatosis (Esau, Davis et al. 2006. Elmen. Lindow et al. 2008). While these studies paved the way for the first experiments of miRNA targeting in non-human primates and shed light on the use of miR-122 inhibitors to treat dyslipidemias (Elmen, Lindow et al. 2008, Elmen, Lindow et al. 2008, Lanford, Hildebrandt-Eriksen et al. 2010), the mechanistic understanding by which anti-miR-122 mediates its effects on lipid homeostasis is still unclear. Unfortunately, this incomprehension, combined with adverse consequences of reduced HDL-C and increased risk of developing hepatocellular carcinomas, have challenged the fervent development of miR-122 antisense technologies (Esau, Davis et al. 2006, Elmen, Lindow et al. 2008)

Functional genomic screens can provide a direct and powerful approach to identify gene and/or miRNA functions in mammalian biology. Indeed, several in vitro screens based on miRNA expression libraries have proven to be highly useful (Voorhoeve, le Sage et al. 2006, Huang, Gumireddy et al. 2008, Izumiya, Okamoto et al. 2010, Poell, van Haastert et al. 2011). Although these types of screens circumvent the problem of identifying functionally relevant miRNA target genes, they inherently give rise to high rates of false positives and negatives. Furthermore, high-throughput identification of miRNA function relies on unnaturally high expression levels of miRNAs, which may cause artifacts and thwart the tissue-specific functional roles of certain miRNA genes. To address these problems, the present inventors integrated results from genome-wide screen with computational predictions from TargetScan, as well as preexisting deep sequencing data on miRNA expression and activity. With this method, the present inventors were able to narrow down our hit list from 25% of miRNAs screened to 0.12%, which is well within the range of acceptable 'hit' rates for genome-wide screens (Malo, Hanley et al. 2006). Nevertheless, it cannot be completely ruled out that some candidates have been discarded that may play a functional role in controlling LDL levels, as the present screen only focused on miRNAs that effect LDLR activity by direct repression of the LDLR. Furthermore, many miRNAs were found to significantly increase DiI-LDL uptake. Given the complex regulatory mechanisms governing the expression of the LDLR, it is likely that some of these miRNAs regulate LDLR activity by targeting post-transcriptional regulators of the LDLR, such as PCSK9 and IDOL (Benjannet, Rhainds et al. 2004, Zelcer, Hong et al. 2009).

Out of the 423 miRNAs identified to negatively regulate LDLR activity, miR-148a and miR-27b were selected for follow-up studies, miR-148a is an intergenic miRNA located on human chromosome 7 and has previously been shown to modulate cell transformation and tumor angiogenesis (Yu, Li et al. 2011, Xu, Jiang et al. 2013). Additionally, miR-148a is aberrantly expressed in several types of cancers, with its down-regulation well described in various solid tumors, such as gastric, colorectal, esophageal, and pancreatic carcinomas (Lujambio, Calin et al. 2008, Hummel, Watson et al. 2011, Zhang, Li et al. 2011, Zheng, Liang et al. 2011). Interestingly, miR-148a was recently described to be upregulated in differentiating liver progenitors and shown to play a role in the fate of the liver by inducing hepatospecific gene expression and suppressing tumor cell invasion (Gailhouste, Gomez-Santos et al. 2013). This study demonstrates the role of miR-148a in regulating LDLR activity indicating that miR-148a plays an important role in the liver. In addition to identifying miR-148a, the present screen also identified miR-148b, the second member of the miR-148 family, as a negative regulator of LDLR activity. Like miR-148a, miR-148b is predicted to target the LDLR, is highly expressed in human liver tissue, and is upregulated with dietary cholesterol. Several studies have also demonstrated a similar tumor suppressive function for this miRNA in ovarian cancer (Chang, Zhou et al. 2012).

As demonstrated herein, miR-148a controls LDLR activity and appears to be regulated by SREBP1c. LXR-mediated induction of SREBP1c results in increased expression of miR-148a and a resultant decrease in LDLR expression. While these results suggest that LDLR expression is regulated by the LXR-SREBP1c-dependent induction of miR-148a (FIG. 13F), one cannot rule out that the decrease in LDLR after T090 treatment is due to an increase in miR-185 or the LXR-Idol axis (Zelcer 2009, Yang 2014). Experiments using miR-148a inhibitors and LXR agonists can elucidate the mechanism by which miR-148a contributes to the post-transcriptional regulation of LDLR. Nevertheless, as miR-148a controls LDLR activity by directly binding to and repressing LDLR expression, these results may define a complementary LXR-SREBP1c-mediated mechanism for post-transcriptionally controlling the expression of LDLR, and thus, fine-tuning cholesterol homeostasis (FIG. 13E).

In the present example, the miRNA that has been characterized the most, miR-27b, is a member of the miR-27 family, of which there are two isoforms, miR-27a and miR-27b. While miR-27a is an intergenic miRNA, miR-27b is located within the 14$^{th}$ intron of the APO gene on human chromosome 9 and is a member of the miR-23b~27b~24-1 cluster. Unlike miR-148, miR-27 has been implicated in numerous cellular processes that regulate atherosclerosis, including angiogenesis, adipogenesis, inflammation, lipid metabolism, oxidative stress, insulin resistance and type-2 diabetes (Chen, Yin et al. 2012). Additionally, miR-27 levels correlate with clinical pathological factors and the prognosis of patients with atherosclerosis (Chen, Yin et al. 2012). Moreover, aberrant expression of miR-27 has been shown to be a predictor for unstable atherosclerotic plaques (Li, Cao et al. 2011, Staszel, Zapala et al. 2011).

In particular, miR-27 has been shown to directly target many lipid-metabolism transcription factors, including RXRα, PPARα, and PPARγ (Karbiener, Fischer et al. 2009, Kim, Kim et al. 2010, Kida, Nakajima et al. 2011, Shirasaki, Honda et al. 2013). In addition to these, here, identified and described herein are three novel targets for miR-27b, namely LDLR, LDLRAP1 and ABCA1. By inhibiting the expression of LDLR and LDLRAP1, miR-27b reduces DiI-LDL uptake and binding, and concomitantly decreases intracellular cholesterol concentrations in human hepatic cells. The decreased expression of hepatic LDLR and LDLRAP1 would be expected to augment circulating plasma LDL-C levels in vivo. Indeed, when miR-27b was over-expressed in the livers of mice fed a WD, a marked increase in IDL/LDL cholesterol was found. This increase in LDL-C suggests that miR-27b treatment either, 1) increases VLDL secretion or, 2) reduces lipoprotein clearance from the circulation. As the major route of clearance of ApoE- and ApoB-containing lipoproteins is by means of LDLR-mediated enodcytosis in the liver (Dietschy, Turley et al. 1993), the present results suggest that the reduction in LDL-C is mainly due to miR-27b-mediated repression of hepatic LDLR. While this does not rule out the possibility that miR-27b could be affecting VLDL secretion, it may establish a key role for miR-27b in regulating LDLR activity in vivo, thereby giving confidence that other miRNAs identified in this genome-wide screen also play functionally relevant roles in controlling LDL uptake. Recently, Shirasaki et al. reported that ABCA1 was a direct target of miR-27a in human hepatoma cells (Shirasaki, Honda et al. 2013). It is shown herein that the second member of the miR-27 family, miR-27b, also directly targets the 3'UTR of ABCA1 and represses ABCA1 mRNA and protein levels. In addition, this example demonstrates a role for miR-27b in regulating cholesterol efflux to ApoA1. Consistent with this result, mice fed a chow diet and treated with miR-27b show a progressive decline in HDL and total cholesterol levels.

Augmented expression of LDLR would be expected to decrease circulating plasma LDL-C levels in vivo, and thus reduce the burden of cardiovascular disease. Given the role of miR-148a and miR-27b in negatively regulating LDLR expression and activity, one would predict that inhibitors of these miRNAs would represent a novel therapeutic strategy for increasing hepatic LDLR expression and decreasing plasma LDL. Indeed, when the inventors inhibited miR-148a and miR-27b expression using LNA oligonucleotides in mice, they found a marked increase in hepatic LDLR expression, thus suggesting that the endogenous levels of miR-148a and miR-27b are important for regulating LDLR expression in vivo. Experiments using non-human primates and/or "humanized" mouse models that exhibit LDL-dominant lipoprotein profiles, such as Apobec−/−; CETPTg mice, should help characterize the endogenous role of miR-148a and miR-27b in regulating levels of LDL-C.

While the inventors cannot completely rule out the possibility that miR-27b and miR-148a may alter other pathways that contribute to LDL-C metabolism, the present study unequivocally establishes a key role for both miRNAs in regulating LDLR expression in vivo, thereby giving confidence that other miRNAs identified in this genome-wide screen also play functionally relevant roles in controlling LDL uptake. Indeed, single-nucleotide polymorphisms (SNPs) in the promoter region of miR-148a contribute to altered LDL-C and triglyceride levels in humans (FIG. 12A) (Do 2013, Global Lipids Genetics 2013). These genetic polymorphisms may affect the expression of miR-148a. For example, the T allele at rs472251 in the miR-148a gene was strongly associated with reduced LDL-C. While the mechanism by which this SNP contributes to altered LDL-C remains unknown, one can imagine a scenario where the SNP leads to decreased expression of miR-148a, thereby increasing LDLR expression and reducing levels of LDL-C. Experiments are therefore warranted to dissect the contribution of this variant to altered lipid levels and cardiovascular disease risk.

Altogether, these results underscore the importance of miRNAs in regulating LDLR expression. Specifically, this data highlights the therapeutic potential of suppressing miR-27b and miR-148a activity to simultaneously reduce circulating levels of LDL-C and increase levels of HDL-C, beneficial outcomes for reducing the global burden of atherosclerosis and related dyslipidemias.

REFERENCES

Ambros, V. (2004). "The functions of animal microRNAs." *Nature* 431(7006): 350-355.

Arora, A. and D. A. Simpson (2008). "Individual mRNA expression profiles reveal the effects of specific microRNAs." *Genome Biol* 9(5): R82.

Barad, O., et al. (2004). "MicroRNA expression detected by oligonucleotide microarrays: system establishment and expression profiling in human tissues." *Genome Res* 14(12): 2486-2494.

Bartel, D. P. (2004). "MicroRNAs: genomics, biogenesis, mechanism, and function." *Cell* 116(2): 281-297.

Bartel, D. P. (2009). "MicroRNAs: target recognition and regulatory functions." *Cell* 136(2): 215-233.

Benjannet, S., et al. (2004). "NARC-1/PCSK9 and its natural mutants: zymogen cleavage and effects on the low density lipoprotein (LDL) receptor and LDL cholesterol." *J Biol Chem* 279(47): 48865-48875.

Birmingham, A., et al. (2009). "Statistical methods for analysis of high-throughput RNA interference screens." *Nat Methods* 6(8): 569-575.

Bobard. A., Hainault, I., Ferre, P. Foufelle, F. & Bossard, P. Differential regulation of sterol regulatory element-binding protein 1c transcriptional activity by insulin and liver X receptor during liver development. *The Journal of biological chemistry* 280, 199-206, doi: 10.1074/jbc.M406522200 (2005)

Brown, M. S., et al. (1973). "Regulation of 3-hydroxy-3-methylglutaryl coenzyme A reductase activity in human fibroblasts by lipoproteins." *Proc Natl Acad Sci USA* 70(7): 2162-2166.

Brown, M. S. and J. L. Goldstein (1974). "Familial hypercholesterolemia: defective binding of lipoproteins to cultured fibroblasts associated with impaired regulation of 3-hydroxy-3-methylglutaryl coenzyme A reductase activity." *Proceedings of the National Academy of Sciences of the United States of America* 71(3): 788-792.

Brown, M. S. and J. L. Goldstein (1976). "Receptor-mediated control of cholesterol metabolism." *Science* 191 (4223): 150-154.

Brown, M. S. and J. L. Goldstein (1986). "A receptor-mediated pathway for cholesterol homeostasis." *Science* 232(4746): 34-47.

Brown, M. S. and J. L. Goldstein (1997). "The SREBP pathway: regulation of cholesterol metabolism by proteolysis of a membrane-bound transcription factor." *Cell* 89(3): 331-340.

Calvo, D., et al. (1998). "Human CD36 is a high affinity receptor for the native lipoproteins HDL, LDL, and VLDL." *J Lipid Res* 39(4): 777-788.

Chang, H., et al. (2012). "Increased expression of miR-148b in ovarian carcinoma and its clinical significance." *Mol Med Rep* 5(5): 1277-1280.

Chen, W. J., et al. (2012). "The magic and mystery of microRNA-27 in atherosclerosis." *Atherosclerosis* 222 (2): 314-323.

de Aguiar Vallim, T., et al. (2013). "MicroRNA-144 Regulates Hepatic ABCA1 and Plasma HDL Following Activation of the Nuclear Receptor FXR." *Circ Res*.

Dietschy, J. M., et al. (1993). "Role of liver in the maintenance of cholesterol and low density lipoprotein homeostasis in different animal species, including humans." *J Lipid Res* 34(10): 1637-1659.

Do, R. et al. Common variants associated with plasma triglycerides and risk for coronary artery disease. *Nature genetics* 45, 1345-1352, doi: 10.1038/ng.2795 (2013).

Global Lipids Genetics, C. et al. Discovery and refinement of loci associated with lipid levels. *Nature genetics* 45, 1274-1283, doi:10.1038/ng.2797 (2013).

Elmen, J., et al. (2008). "LNA-mediated microRNA silencing in non-human primates." *Nature* 452(7189): 896-899.

Elmen, J., et al. (2008). "Antagonism of microRNA-122 in mice by systemically administered LNA-antimiR leads to up-regulation of a large set of predicted target mRNAs in the liver." *Nucleic Acids Res* 36(4): 1153-1162.

Ernst, J. & Kellis, M. Discovery and characterization of chromatin states for systematic annotation of the human genome. *Nature biotechnology* 28, 817-825, doi:10.1038/nbt.1662 (2010).

Esau, C., et al. (2006). "miR-122 regulation of lipid metabolism revealed by in vivo antisense targeting." *Cell Metab* 3(2): 87-98.

Filipowicz, W., et al. (2008). "Mechanisms of post-transcriptional regulation by microRNAs: are the answers in sight?"*Nature reviews. Genetics* 9(2): 102-114.

Gailhouste, L., et al. (2013). "MiR-148a plays a pivotal role in the liver by promoting the hepatospecific phenotype and suppressing the invasiveness of transformed cells." *Hepatology*.

Gerstein, M. B. et al. Architecture of the human regulatory network derived from ENCODE data. *Nature* 489, 91-100, doi:10.1038/nature 11245 (2012).

Glass, C. K. and J. L. Witztum (2001). "Atherosclerosis. the road ahead." *Cell* 104(4): 503-516.

Goldstein, J. L., et al. (1976). "Release of low density lipoprotein from its cell surface receptor by sulfated glycosaminoglycans." *Cell* 7(1): 85-95.

Goldstein, J. L. and M. S. Brown (1990). "Regulation of the mevalonate pathway." *Nature* 343(6257): 425-430.

Gould, A. L., et al. (1998). "Cholesterol reduction yields clinical benefit: impact of statin trials." *Circulation* 97(10): 946-952.

Hennekens, C. H. (1998). "Increasing burden of cardiovascular disease: current knowledge and future directions for research on risk factors." *Circulation* 97(11): 1095-1102.

Horton, J. D., Goldstein, J. L. & Brown, M. S. SREBPs: activators of the complete program of cholesterol and fatty acid synthesis in the liver. *The Journal of clinical investigation* 109, 1125-1131, doi:10.1172/JCI15593 (2002).

Huang da, W., et al. (2009a). "Systematic and integrative analysis of large gene lists using DAVID bioinformatics resources." *Nat Protoc* 4(1): 44-57.

Huang da, W., Sherman, B. T. & Lempicki, R. A. Bioinformatics enrichment tools: paths toward the comprehensive functional analysis of large gene lists. *Nucleic acids research* 37, 1-13, doi: 10.1093/nar/gkn923 (2009b).

Huang, Q., et al. (2008). "The microRNAs miR-373 and miR-520c promote tumour invasion and metastasis." *Nat Cell Biol* 10(2): 202-210.

Hummel, R., et al. (2011). "Mir-148a improves response to chemotherapy in sensitive and resistant oesophageal adenocarcinoma and squamous cell carcinoma cells." *J Gastrointest Surg* 15(3): 429-438.

Izumiya, M., et al. (2010). "Functional screening using a microRNA virus library and microarrays: a new high-throughput assay to identify tumor-suppressive microRNAs." *Carcinogenesis* 31(8): 1354-1359.

Karbiener, M., et al. (2009). "microRNA miR-27b impairs human adipocyte differentiation and targets PPARgamma." *Biochem Biophys Res Commun* 390(2): 247-251.

Kassim, S. H., et al. (2013). "Adeno-associated virus serotype 8 gene therapy leads to significant lowering of plasma cholesterol levels in humanized mouse models of homozygous and heterozygous familial hypercholesterolemia." *Hum Gene Ther* 24(1): 19-26.

Kida, K., et al. (2011). "PPARalpha is regulated by miR-21 and miR-27b in human liver." *Pharm Res* 28(10): 2467-2476.

Kim, J., et al. (2012). "MiR-106b impairs cholesterol efflux and increases Abeta levels by repressing ABCA1 expression." *Exp Neurol* 235(2): 476-483.

Kim, S. Y., et al. (2010). "miR-27a is a negative regulator of adipocyte differentiation via suppressing PPARgamma expression." *Biochem Biophys Res Commun* 392(3): 323-328.

Krutzfeldt, J., et al. (2005). "Silencing of microRNAs in vivo with 'antagomirs'." *Nature* 438(7068): 685-689.

Landgraf, P., et al. (2007). "A mammalian microRNA expression atlas based on small RNA library sequencing." *Cell* 129(7): 1401-1414.

Lanford, R. E., et al. (2010). "Therapeutic silencing of microRNA-122 in primates with chronic hepatitis C virus infection." *Science* 327(5962): 198-201.

Li, T., et al. (2011). "Identification of miR-130a, miR-27b and miR-210 as serum biomarkers for atherosclerosis obliterans." *Clin Chim Acta* 412(1-2): 66-70.

Lujambio, A., et al. (2008). "A microRNA DNA methylation signature for human cancer metastasis." *Proc Natl Acad Sci USA* 105(36): 13556-13561.

Lusis, A. J. (2000). "Atherosclerosis." *Nature* 407(6801): 233-241.

Malo, N., et al. (2006). "Statistical practice in high-throughput screening data analysis." *Nat Biotechnol* 24(2): 167-175.

Maxfield, F. R. and I. Tabas (2005). "Role of cholesterol and lipid organization in disease." *Nature* 438(7068): 612-621.

Mercer, J., et al. (2012). "RNAi screening reveals proteasome- and Cullin3-dependent stages in vaccinia virus infection." *Cell Rep* 2(4): 1036-1047.

Mi, H. et al. PANTHER version 7: improved phylogenetic trees, orthologs and collaboration with the Gene Ontology Consortium. *Nucleic acids research* 38, D204-210, doi: 10.1093/nar/gkp 1019 (2010).

Monteys, A. M. et al. Structure and activity of putative intronic miRNA promoters. *Rna* 16, 495-505, doi: 10.1261/rna.1731910 (2010).

Najafi-Shoushtari, S. H., et al. (2010). "MicroRNA-33 and the SREBP host genes cooperate to control cholesterol homeostasis." *Science* 328(5985): 1566-1569.

Oram, J. F. and A. M. Vaughan (2000). "ABCA1-mediated transport of cellular cholesterol and phospholipids to HDL apolipoproteins." *Curr Opin Lipidol* 11(3): 253-260.

Park, S. W., et al. (2004). "Post-transcriptional regulation of low density lipoprotein receptor protein by proprotein convertase subtilisin/kexin type 9a in mouse liver." *J Biol Chem* 279(48): 50630-50638.

Poell, J. B., et al. (2011). "Functional microRNA screening using a comprehensive lentiviral human microRNA expression library." *BMC Genomics* 12: 546.

Purcell-Huynh, D. A. et al. Transgenic mice expressing high levels of human apolipoprotein B develop severe atherosclerotic lesions in response to a high-fat diet. *The Journal of clinical investigation* 95, 2246-2257, doi:10.1172/JCI117915 (1995).

Ramirez. C. M., et al. (2011). "MicroRNA-758 regulates cholesterol efflux through posttranscriptional repression of ATP-binding cassette transporter A1." *Arterioscler Thromb Vasc Biol* 31(11): 2707-2714.

Ramirez, C. M., et al. (2013). "Control of Cholesterol Metabolism and Plasma HDL Levels by miRNA-144." *Circ Res.*

Rayner, K. J., et al. (2011). "Inhibition of miR-33a/b in non-human primates raises plasma HDL and lowers VLDL triglycerides." *Nature* 478(7369): 404-407.

Saini, H. K., Griffiths-Jones, S. & Enright, A. J. Genomic analysis of human microRNA transcripts. *Proceedings of the National Academy of Sciences of the United States of America* 104, 17719-17724, doi:10.1073/pnas.0703890104 (2007).

Shimano, H. et al. Isoform 1c of sterol regulatory element binding protein is less active than isoform 1a in livers of transgenic mice and in cultured cells. *The Journal of clinical investigation* 99, 846-854, doi:10.1172/JCI119248 (1997).

Shirasaki, T., et al. (2013). "MicroRNA-27a Regulates Lipid Metabolism and Inhibits Hepatitis C Virus Replication in Human Hepatoma Cells." *J Virol* 87(9): 5270-5286.

Sjouke, B., et al. (2011). "Familial hypercholesterolemia: present and future management." *Current cardiology reports* 13(6): 527-536.

Staszel, T., et al. (2011). "Role of microRNAs in endothelial cell pathophysiology." *Pol Arch Med Wewn* 121(10): 361-366.

Suarez, Y., et al. (2004). "Synergistic upregulation of low-density lipoprotein receptor activity by tamoxifen and lovastatin." *Cardiovascular research* 64(2): 346-355.

Szklarczyk, D., et al. (2011). "The STRING database in 2011: functional interaction networks of proteins, globally integrated and scored." *Nucleic Acids Res* 39 (Database issue): D561-568.

Thomas, P. D., et al. (2003). "PANTHER: a library of protein families and subfamilies indexed by function." *Genome Res* 13(9): 2129-2141.

Vickers, K. C., et al. (2013). "MicroRNA-27b is a regulatory hub in lipid metabolism and is altered in dyslipidemia." *Hepatoloy* 57(2): 533-542.

Voorhoeve, P. M., et al. (2006). "A genetic screen implicates miRNA-372 and miRNA-373 as oncogenes in testicular germ cell tumors." *Cell* 124(6): 1169-1181.

Wang, L., et al. (2010). "Systematic evaluation of AAV vectors for liver directed gene transfer in murine models." *Mol Ther* 18(1): 118-125.

Xu, Q., et al. (2013). "A regulatory circuit of miR-148a/152 and DNMT1 in modulating cell transformation and tumor angiogenesis through IGF-IR and IRS1." *J Mol Cell Biol* 5(1): 3-13.

Yang, M. et al. Identification of miR-185 as a regulator of de novo cholesterol biosynthesis and low density lipoprotein uptake. *Journal of lipid research* 55, 226-238, doi: 10.1194/jlr.M041335 (2014).

Yu, J., et al. (2011). "MiR-148a inhibits angiogenesis by targeting ERBB3." *J Biomed Res* 25(3): 170-177.

Zelcer, N., et al. (2009). "LXR regulates cholesterol uptake through Idol-dependent ubiquitination of the LDL receptor." *Science* 325(5936): 100-104.

Zhang, H., et al. (2011). "MiR-148a promotes apoptosis by targeting Bcl-2 in colorectal cancer." *Cell Death Differ* 18(11): 1702-1710.

Zhang, J. H., et al. (1999). "A Simple Statistical Parameter for Use in Evaluation and Validation of High Throughput Screening Assays." *J Biomol Screen* 4(2): 67-73.

Zheng, B., et al. (2011). "MicroRNA-148a suppresses tumor cell invasion and metastasis by downregulating ROCK1 in gastric cancer." *Clin Cancer Res* 17(24): 7574-7583.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein, including all patents, published patent applications, and published scientific articles, are incorporated by reference in their entireties for all purposes.

TABLE 1

Top hits from primary miRNA screen.

| Number | Plate | Well | miRNA | Replicate 1 | Replicate 2 | Replicate 3 | Rank |
|---|---|---|---|---|---|---|---|
| 1 | HM-01 | I1 | hsa-miR-140-5p | −2.31 | −1.93 | −2.25 | I |
| 2 | HM-02 | P11 | hsa-miR-876-3p | −2.09 | −2.11 | −2.12 | I |
| 3 | HM-02 | B14 | hsa-miR-519a | −2.08 | −2.03 | −2.10 | I |
| 4 | HM-01 | A5 | hsa-miR-133b | −2.04 | −2.02 | −1.93 | II |
| 5 | HM-01 | A2 | hsa-miR-133a | −1.88 | −2.11 | −1.96 | II |
| 6 | HM-03 | A15 | hsa-miR-1244 | −2.03 | −1.82 | −2.08 | II |
| 7 | HM-02 | A19 | hsa-miR-128 | −2.04 | −1.81 | −2.05 | II |
| 8 | HM-01 | O3 | hsa-miR-520e | −1.97 | −1.78 | −1.83 | II |
| 9 | HM-02 | J13 | hsa-miR-520d-3p | −1.76 | −1.73 | −1.75 | II |
| 10 | HM-01 | F17 | hsa-miR-520b | −1.79 | −1.60 | −1.78 | II |
| 11 | HM-02 | F3 | hsa-miR-520c-3p | −1.81 | −1.77 | −1.52 | II |
| 12 | HM-01 | O13 | hsa-miR-520a-3p | −1.67 | −1.80 | −1.62 | II |
| 13 | HM-01 | K11 | hsa-miR-148b | −1.63 | −1.80 | −1.62 | II |
| 14 | HM-01 | K9 | hsa-miR-148a | −1.69 | −1.68 | −1.61 | II |
| 15 | HM-01 | G5 | hsa-miR-372 | −1.45 | −1.93 | −1.61 | II |
| 16 | HM-01 | C15 | hsa-miR-302b | −1.60 | −1.76 | −1.49 | II |
| 17 | HM-01 | D17 | hsa-miR-373 | −1.55 | −1.77 | −1.44 | II |
| 18 | HM-01 | B5 | hsa-miR-302a | −1.43 | −1.68 | −1.61 | II |
| 19 | HM-01 | E12 | hsa-miR-302c | −1.38 | −1.67 | −1.52 | II |
| 20 | HM-01 | B3 | hsa-miR-302d | −1.09 | −1.77 | −1.50 | II |
| 21 | HM-02 | O19 | hsa-miR-17 | −1.48 | −1.08 | −1.60 | II |
| 22 | HM-01 | J13 | hsa-miR-330-5p | −1.28 | −1.24 | −1.42 | II |
| 23 | HM-02 | M1 | hsa-miR-454 | −1.08 | −1.40 | −1.41 | II |
| 24 | HM-05 | F12 | hsa-miR-4644 | −1.08 | −1.55 | −1.00 | II |
| 25 | HM-02 | F22 | hsa-miR-619d | −1.33 | −0.92 | −1.38 | II |
| 26 | HM-01 | A9 | hsa-miR-328 | −1.14 | −1.32 | −1.12 | II |
| 27 | HM-01 | B13 | hsa-miR-93 | −1.06 | −1.39 | −1.13 | II |
| 28 | HM-01 | A21 | hsa-miR-20a | −0.88 | −1.35 | −1.14 | II |
| 29 | HM-01 | C5 | hsa-miR-106b | −1.27 | −1.13 | −0.98 | II |
| 30 | HM-02 | E13 | hsa-miR-758 | −1.24 | −1.26 | −0.85 | II |
| 31 | HM-02 | E15 | hsa-miR-153 | −0.83 | −1.25 | −1.25 | II |
| 32 | HM-01 | C8 | hsa-miR-130a | −0.96 | −1.22 | −1.03 | II |
| 33 | HM-01 | I8 | hsa-miR-326 | −0.95 | −1.01 | −1.03 | III |
| 34 | HM-01 | F21 | hsa-miR-410 | −0.84 | −1.13 | −0.89 | III |
| 35 | HM-02 | E18 | hsa-miR-185 | −1.32 | −0.95 | −0.48 | III |
| 36 | HM-02 | E12 | hsa-miR-653 | −0.92 | −0.87 | −0.92 | III |
| 37 | HM-01 | P3 | hsa-miR-411 | −0.70 | −1.08 | −0.92 | III |
| 38 | HM-01 | K6 | hsa-miR-24 | −0.97 | −0.98 | −0.61 | III |
| 39 | HM-01 | G10 | hsa-miR-19b | −0.74 | −0.87 | −0.76 | III |
| 40 | HM-01 | K10 | hsa-miR-27b | −0.86 | −1.07 | −0.26 | III |

TABLE 1-continued

Top hits from primary miRNA screen.

| Number | Targets LDLR[1] | Conserved[1] | Human Liver Expression O. Barad et al[2] | Human Liver Expression P. Landgraf et al[3] | Mouse Liver Expression Vickers et al[4] | Liver Activity[5] | Response to Cholesterol[4] |
|---|---|---|---|---|---|---|---|
| 1 | yes | yes | / | / | low | low | ↑HFD |
| 2 | yes | yes | / | / | / | / | / |
| 3 | yes | no | / | / | / | / | / |
| 4 | yes | no | / | / | / | low | / |
| 5 | yes | no | / | / | / | low | / |
| 6 | yes | yes | / | / | / | / | / |
| 7 | yes | yes | / | / | low | high | ↓HFD |
| 8 | yes | no | / | / | / | high | / |
| 9 | yes | no | / | / | / | / | / |
| 10 | yes | no | / | / | / | / | / |
| 11 | yes | no | / | / | / | / | / |
| 12 | yes | no | / | / | / | / | / |
| 13 | yes | yes | medium | very low | low | medium | ↑↑↑HFD |
| 14 | yes | yes | medium | very low | high | medium | ↑↑↑HFD |
| 15 | yes | no | / | / | / | / | / |
| 16 | yes | no | / | / | / | / | / |
| 17 | yes | no | / | / | / | / | / |
| 18 | yes | no | / | / | / | / | / |
| 19 | yes | no | / | / | / | / | / |
| 20 | yes | no | / | / | / | / | / |
| 21 | yes | yes | / | medium | medium | / | ↓HFD |
| 22 | yes | no | / | / | / | / | / |
| 23 | yes | yes | / | / | / | / | / |
| 24 | yes | no | / | / | / | / | / |
| 25 | yes | yes | / | / | / | / | / |
| 26 | yes | yes | / | / | medium | / | ↑HFD |
| 27 | yes | yes | low | very low | medium | medium | ↑↑↑HFD |
| 28 | yes | yes | / | / | low | high | ↑HFD |
| 29 | yes | yes | / | / | low | high | ↑HFD |
| 30 | yes | no | / | / | / | / | / |
| 31 | yes | no | / | / | / | high | / |
| 32 | yes | yes | / | / | high | medium | ↓↓HFD |
| 33 | yes | no | / | / | / | high | / |
| 34 | yes | no | / | / | / | / | / |
| 35 | yes | no | / | medium | low | medium | — |
| 36 | yes | no | / | / | / | / | / |
| 37 | yes | no | / | / | / | / | / |
| 38 | yes | no | high | high | medium | low | ↑↑↑HFD |
| 39 | yes | yes | / | very low | medium | high | ↑↑↑HFD |
| 40 | yes | yes | medium | medium | medium | high | ↑↑ HFD |

Notes:
Slashes denote those miRNAs not reported in each study.
Minus signs indicate no change in expression.
Number of arrows indicates levels of fold change in expression, high fat diet (HFD)/chow diet (CD) (↑low to ↑↑↑high fold-change).
[1]TargetScan,
[2]Barad et al,
[3]Landgra et al.,
[4]Vickers et al
[5]Arora et al.

TABLE 2

| Number | Plate | Well | miRNA | Robust Z-score Replicate 1 | Robust Z-score Replicate 2 | Robust Z-score Replicate 3 | Average Robust '-score | Rank |
|---|---|---|---|---|---|---|---|---|
| 1 | HM-03 | E1 | hsa-miR-1255a | −3.209681303 | −3.382890194 | −3.091428844 | −3.228000114 | I |
| 2 | HM-03 | I3 | hsa-miR-1255b | −3.016979738 | −3.147914181 | −2.693712192 | −2.952868704 | I |
| 3 | HM-05 | M1 | hsa-miR-4652-5p | −2.900565971 | −2.823968077 | −2.949064402 | −2.891199483 | I |
| 4 | HM-04 | C2 | hsa-miR-3681 | −2.706948805 | −2.767203709 | −2.969691767 | −2.81461476 | I |
| 5 | HM-02 | L12 | hsa-miR-342-5p | −2.776879425 | −2.751693566 | −2.79365765 | −2.77407688 | I |
| 6 | HM-03 | C10 | hsa-miR-1293 | −2.778260441 | −2.773749701 | −2.768698403 | −2.773569515 | I |
| 7 | HM-03 | N19 | hsa-miR-3191 | −2.809752784 | −2.699266072 | −2.720612102 | −2.74321032 | I |
| 8 | HM-03 | B2 | hsa-miR-3190 | −2.646012537 | −2.580964523 | −2.702258698 | −2.643078586 | I |
| 9 | HM-04 | G17 | hsa-miR-3907 | −2.690364228 | −2.532473724 | −2.696701071 | −2.639846341 | I |
| 10 | HM-03 | L20 | hsa-miR-3165 | −2.569512983 | −2.614007911 | −2.484835397 | −2.556118764 | I |
| 11 | HM-03 | L17 | hsa-miR-3150 | −2.644726155 | −2.53383707 | −2.44158049 | −2.540047905 | I |
| 12 | HM-05 | I22 | hsa-miR-3689d | −2.469044112 | −2.46347802 | −2.588983779 | −2.507168637 | I |

TABLE 2-continued

| Number | Plate | Well | miRNA | Robust Z-score Replicate 1 | Replicate 2 | Replicate 3 | Average Robust '-score | Rank |
|---|---|---|---|---|---|---|---|---|
| 13 | HM-05 | D14 | hsa-miR-4438 | −2.280161605 | −2.708215479 | −2.481381479 | −2.489919521 | I |
| 14 | HM-04 | P9 | hsa-miR-4747-5p | −2.4447603 | −2.468239745 | −2.514147716 | −2.47571592 | I |
| 15 | HM-01 | A13 | hsa-miR-7 | −2.491442455 | −2.626188554 | −2.225504264 | −2.447711758 | I |
| 16 | HM-03 | O17 | hsa-miR-1204 | −2.461842325 | −2.539909163 | −2.335968606 | −2.445904698 | I |
| 17 | HM-03 | K22 | hsa-miR-205* | −2.430120398 | −2.518957651 | −2.382407381 | −2.443828477 | I |
| 18 | HM-04 | O21 | hsa-miR-3918 | −1.833886184 | −2.486387803 | −2.677799507 | −2.332691165 | I |
| 19 | HM-05 | M7 | hsa-miR-4667-5p | −2.352870252 | −2.204442549 | −2.318373156 | −2.291895319 | I |
| 20 | HM-01 | L11 | hsa-miR-363* | −2.310495627 | −2.298951756 | −2.190286772 | −2.266578052 | I |
| 21 | HM-03 | C12 | hsa-miR-1294 | −2.318833988 | −2.24271413 | −2.219364614 | −2.260304244 | I |
| 22 | HM-01 | J7 | hsa-let-7a-2* | −3.396741646 | −1.605689203 | −1.75972987 | −2.254053573 | I |
| 23 | HM-04 | A10 | hsa-miR-3911 | −2.326859342 | −2.071208589 | −2.360043085 | −2.252703672 | I |
| 24 | HM-05 | M3 | hsa-miR-4655-5p | −2.260810036 | −2.187609747 | −2.276743625 | −2.241721136 | I |
| 25 | HM-04 | E10 | rno-miR-2964 | −2.064881584 | −2.814329288 | −1.815472393 | −2.231561089 | I |
| 26 | HM-02 | J20 | hsa-miR-19b-1* | −2.202739842 | −2.262286387 | −2.210357592 | −2.22512794 | I |
| 27 | HM-03 | C19 | hsa-miR-1185 | −2.135622262 | −2.264734401 | −2.26038982 | −2.220248828 | I |
| 28 | HM-03 | D17 | hsa-miR-548s | −2.196936301 | −2.211475026 | −2.194317015 | −2.200909448 | I |
| 29 | HM-04 | H3 | hsa-miR-4701-3p | −2.238925432 | −1.902903164 | −2.372429924 | −2.171419507 | I |
| 30 | HM-01 | I1 | hsa-miR-140-5p | −2.310196736 | −1.932993019 | −2.249446184 | −2.164211979 | I |
| 31 | HM-05 | K13 | hsa-miR-4425 | −1.957902147 | −2.299183286 | −2.230984572 | −2.162690002 | I |
| 32 | HM-05 | K15 | hsa-miR-4714-5p | −2.263436869 | −2.186151821 | −2.017809505 | −2.155799398 | I |
| 33 | HM-01 | E14 | hsa-miR-519c-3p | −1.852520576 | −2.137453557 | −2.463761119 | −2.151247104 | I |
| 34 | HM-03 | K4 | hsa-miR-1973 | −2.095337939 | −2.09229791 | −2.245051212 | −2.144229021 | I |
| 35 | HM-02 | A10 | hsa-miR-624 | −2.298842291 | −1.995000683 | −2.101441241 | −2.131761405 | I |
| 36 | HM-02 | O21 | hsa-miR-544 | −2.046430225 | −2.126431866 | −2.195889012 | −2.122917035 | I |
| 37 | HM-03 | H12 | hsa-miR-3144-5p | −2.287130444 | −1.949471856 | −2.129521344 | −2.12210788 | I |
| 38 | HM-04 | O5 | hsa-miR-3926 | −2.110938555 | −1.999067861 | −2.244004637 | −2.118003684 | I |
| 39 | HM-02 | P11 | hsa-miR-876-3p | −2.085346784 | −2.111813959 | −2.118075004 | −2.105078582 | I |
| 40 | HM-05 | I17 | hsa-miR-4527 | −2.082271768 | −1.984442972 | −2.228637564 | −2.098450768 | I |
| 41 | HM-01 | L20 | hsa-miR-609 | −2.063756592 | −2.165310756 | −2.065013059 | −2.098026803 | I |
| 42 | HM-02 | F10 | hsa-miR-519b-3p | −2.111103943 | −2.008598201 | −2.152743433 | −2.090815192 | I |
| 43 | HM-04 | P12 | hsa-miR-4522 | −2.146286517 | −1.860064325 | −2.238867521 | −2.081739454 | I |
| 44 | HM-02 | I20 | hsa-miR-367* | −2.069463937 | −2.073191779 | −2.079407642 | −2.074021119 | I |
| 45 | HM-05 | A6 | hsa-miR-4690-5p | −2.635407273 | −1.652076411 | −1.917311719 | −2.068265135 | I |
| 46 | HM-02 | B14 | hsa-miR-519a | −2.076790745 | −2.025372465 | −2.097936693 | −2.066699968 | I |
| 47 | HM-01 | N10 | hsa-miR-640 | −2.279160971 | −2.022429998 | −1.893679009 | −2.065089993 | I |
| 48 | HM-02 | C8 | hsa-miR-19b-2* | −2.055090714 | −2.053284112 | −2.080895651 | −2.063090159 | I |
| 49 | HM-01 | K17 | hsa-miR-451 | −2.07297483 | −2.014390169 | −2.06913086 | −2.052165286 | I |
| 50 | HM-04 | H2 | hsa-miR-4450 | −2.123710733 | −1.925877431 | −2.081639894 | −2.043742686 | I |
| 51 | HM-05 | G17 | hsa-miR-4664-5p | −2.029955265 | −2.159639046 | −1.934587414 | −2.041393909 | I |
| 52 | HM-04 | O17 | hsa-miR-3674 | −2.046680655 | −2.072134844 | −1.995818447 | −2.038211315 | I |
| 53 | HM-02 | A6 | hsa-miR-19a* | −1.896317313 | −1.953284356 | −2.211475131 | −2.020358934 | I |
| 54 | HM-03 | E13 | hsa-miR-1262 | −1.888022138 | −2.03381113 | −2.132126936 | −2.017996685 | I |
| 55 | HM-03 | H9 | hsa-miR-3149 | −2.140729878 | −1.97116692 | −1.929658457 | −2.013851751 | I |
| 56 | HM-05 | M11 | hsa-miR-4697-5p | −2.00591981 | −2.130668231 | −1.890093697 | −2.008893913 | I |
| 57 | HM-03 | E12 | hsa-miR-1302 | −2.03984022 | −1.953347745 | −2.021976668 | −2.005054878 | I |
| 58 | HM-03 | N3 | hsa-miR-3140 | −2.080340323 | −1.919338274 | −2.007529498 | −2.002402699 | I |
| 59 | HM-05 | B7 | hsa-miR-4694-5p | −1.99108583 | −1.956507988 | −2.057976553 | −2.00185679 | I |
| 60 | HM-01 | A5 | hsa-miR-133b | −2.043219379 | −2.021202135 | −1.934964473 | −1.999795329 | II |
| 61 | HM-01 | I9 | hsa-miR-147 | −2.008158202 | −1.931734608 | −2.046243113 | −1.995378641 | II |
| 62 | HM-01 | A2 | hsa-miR-133a | −1.881434015 | −2.105694419 | −1.959536126 | −1.98222152 | II |
| 63 | HM-01 | P22 | hsa-miR-644 | −1.968237228 | −1.967786763 | −1.996279546 | −1.977434512 | II |
| 64 | HM-03 | A15 | hsa-miR-1244 | −2.028418781 | −1.824805301 | −2.078453994 | −1.977226025 | II |
| 65 | HM-04 | D17 | hsa-miR-4675 | −2.012043347 | −1.903229517 | −2.016292849 | −1.977188571 | II |
| 66 | HM-04 | C17 | hsa-miR-3612 | −1.919212946 | −1.927540518 | −2.078491572 | −1.975081679 | II |
| 67 | HM-03 | B11 | hsa-miR-3157 | −1.784150628 | −2.033020004 | −2.101939532 | −1.973036721 | II |
| 68 | HM-05 | O5 | hsa-miR-3922-5p | −2.095462069 | −1.904598565 | −1.914455746 | −1.97150546 | II |
| 69 | HM-02 | A19 | hsa-miR-128 | −2.042047562 | −1.80562867 | −2.049300133 | −1.965658788 | II |
| 70 | HM-05 | P19 | hsa-miR-4716-3p | −1.764110036 | −2.13226995 | −1.974177086 | −1.956899024 | II |
| 71 | HM-03 | B9 | hsa-miR-4259 | −1.968511903 | −1.89879361 | −2.00280763 | −1.956704381 | II |
| 72 | HM-05 | F14 | hsa-miR-4673 | −1.849093451 | −2.048934802 | −1.958242881 | −1.952090378 | II |
| 73 | HM-03 | P9 | hsa-miR-3127 | −2.038605676 | −1.778443346 | −2.033736728 | −1.950261917 | II |
| 74 | HM-05 | H13 | hsa-miR-4746-3p | −1.830904468 | −1.884548596 | −2.128441393 | −1.947964819 | II |
| 75 | HM-04 | J20 | hsa-miR-4786-3p | −1.879998715 | −1.903426438 | −2.048351834 | −1.943996425 | II |
| 76 | HM-04 | J3 | hsa-miR-4790-3p | −1.981585742 | −1.882251099 | −1.94022232 | −1.934686387 | II |
| 77 | HM-05 | A22 | hsa-miR-4695-3p | −1.995994826 | −1.620446279 | −2.175966982 | −1.930802695 | II |
| 78 | HM-03 | K2 | hsa-miR-2110 | −1.994566548 | −1.844760916 | −1.901832083 | −1.913719849 | II |
| 79 | HM-04 | K7 | hsa-miR-3913 | −1.849091408 | −1.839822537 | −2.028597161 | −1.905837035 | II |
| 80 | HM-03 | J22 | hsa-miR-3186-3p | −1.897996663 | −1.915182306 | −1.864562529 | −1.892580499 | II |
| 81 | HM-03 | C6 | hsa-miR-1291 | −1.951858001 | −1.82444395 | −1.866082482 | −1.880794811 | II |
| 82 | HM-03 | B19 | hsa-miR-3134 | −1.957994288 | −1.709327209 | −1.97364626 | −1.880322586 | II |
| 83 | HM-04 | I3 | hsa-miR-3681* | −1.814934468 | −1.733827486 | −2.077209086 | −1.875357013 | II |
| 84 | HM-04 | O22 | hsa-miR-3136-3p | −1.762602706 | −1.980704219 | −1.879864109 | −1.874390344 | II |
| 85 | HM-02 | I4 | hsa-miR-92a-2* | −1.851925973 | −1.720112495 | −2.024384789 | −1.865474419 | II |
| 86 | HM-01 | O3 | hsa-miR-520e | −1.972289449 | −1.776169143 | −1.829223697 | −1.85922743 | II |
| 87 | HM-02 | C2 | hsa-miR-208b | −1.71616061 | −1.849724452 | −2.003755399 | −1.85654682 | II |
| 88 | HM-03 | P6 | hsa-miR-3170 | −1.976887245 | −1.828189879 | −1.686301336 | −1.830459487 | II |

TABLE 2-continued

| Number | Plate | Well | miRNA | Robust Z-score | | | Average Robust '-score | Rank |
|---|---|---|---|---|---|---|---|---|
| | | | | Replicate 1 | Replicate 2 | Replicate 3 | | |
| 89 | HM-01 | L8 | hsa-miR-650 | −2.006974206 | −1.827341395 | −1.656617081 | −1.830310894 | II |
| 90 | HM-05 | C6 | hsa-miR-4725-3p | −1.80597643 | −1.806131223 | −1.869944101 | −1.827350585 | II |
| 91 | HM-04 | O7 | hsa-miR-3915 | −1.602942461 | −1.774420294 | −2.089030639 | −1.822131131 | II |
| 92 | HM-04 | C19 | hsa-miR-4689 | −1.843930274 | −1.760678224 | −1.856440611 | −1.820351503 | II |
| 93 | HM-04 | O3 | hsa-miR-3605-5p | −1.815306605 | −1.763135705 | −1.877760803 | −1.818734371 | II |
| 94 | HM-05 | F2 | hsa-miR-4735-3p | −1.774112753 | −1.830631518 | −1.834387553 | −1.813043941 | II |
| 95 | HM-05 | B22 | hsa-miR-4701-5p | −1.965353758 | −1.587082328 | −1.855770068 | −1.802735384 | II |
| 96 | HM-04 | E8 | hsa-miR-3622a-5p | −2.074788788 | −1.351614716 | −1.943783223 | −1.790062242 | II |
| 97 | HM-05 | K9 | hsa-miR-4676-3p | −1.727475316 | −1.795656358 | −1.831967956 | −1.78503321 | II |
| 98 | HM-04 | J15 | hsa-miR-4738-5p | −2.02199457 | −1.503906842 | −1.805200643 | −1.777034019 | II |
| 99 | HM-01 | I4 | hsa-miR-208a | −1.811356846 | −1.77181419 | −1.72928977 | −1.770820268 | II |
| 100 | HM-05 | G4 | hsa-miR-4677-5p | −1.887501559 | −1.802043047 | −1.62164743 | −1.770397346 | II |
| 101 | HM-05 | F9 | hsa-miR-3160-5p | −2.031821522 | −1.770011067 | −1.484014662 | −1.761949084 | II |
| 102 | HM-02 | K6 | hsa-miR-625 | −1.680428981 | −1.706139035 | −1.882438212 | −1.75633541 | II |
| 103 | HM-05 | D17 | hsa-miR-4513 | −1.840889663 | −1.836047629 | −1.571310146 | −1.749415813 | II |
| 104 | HM-02 | J13 | hsa-miR-520d-3p | −1.758868367 | −1.733876527 | −1.745135076 | −1.74595999 | II |
| 105 | HM-03 | K16 | hsa-miR-365* | −1.721900241 | −1.730581067 | −1.770133605 | −1.740871849 | II |
| 106 | HM-01 | L9 | hsa-miR-499-5p | −1.772552712 | −1.644090545 | −1.784184935 | −1.733609397 | II |
| 107 | HM-05 | B5 | hsa-miR-3177-5p | −1.372540192 | −1.918528697 | −1.899761565 | −1.730276818 | II |
| 108 | HM-01 | F17 | hsa-miR-520b | −1.787801167 | −1.604461934 | −1.776292363 | −1.722851821 | II |
| 109 | HM-02 | E5 | hsa-miR-765 | −1.664111691 | −1.774585054 | −1.677918855 | −1.705585533 | II |
| 110 | HM-02 | F3 | hsa-miR-520c-3p | −1.813117317 | −1.772217021 | −1.521032786 | −1.702122375 | II |
| 111 | HM-01 | O13 | hsa-miR-520a-3p | −1.666273873 | −1.802271274 | −1.619309851 | −1.695951666 | II |
| 112 | HM-03 | N2 | hsa-miR-3179 | −1.797411089 | −1.782821727 | −1.504796967 | −1.695009928 | II |
| 113 | HM-03 | J20 | ppy-miR-1269 | −1.756934039 | −1.746595961 | −1.577338391 | −1.693622797 | II |
| 114 | HM-05 | C12 | hsa-miR-4525 | −1.751857562 | −1.710858207 | −1.614054974 | −1.692256914 | II |
| 115 | HM-04 | L22 | hsa-miR-4658 | −1.674661447 | −1.663204856 | −1.733608428 | −1.690491577 | II |
| 116 | HM-01 | K11 | hsa-miR-148b | −1.62630329 | −1.802069367 | −1.623674524 | −1.684015727 | II |
| 117 | HM-02 | K21 | hsa-miR-224 | −1.754619168 | −1.687385479 | −1.595675913 | −1.679226853 | II |
| 118 | HM-03 | F2 | hsa-miR-3186-5p | −1.577374055 | −1.683519624 | −1.756784425 | −1.672559368 | II |
| 119 | HM-03 | B7 | hsa-miR-4270 | −1.834464067 | −1.704996238 | −1.470379962 | −1.669946755 | II |
| 120 | HM-05 | C1 | hsa-miR-4654 | −1.653878546 | −1.853962954 | −1.483673849 | −1.663838449 | II |
| 121 | HM-01 | G5 | hsa-miR-372 | −1.454040037 | −1.926476882 | −1.608574192 | −1.66303037 | II |
| 122 | HM-01 | G19 | hsa-miR-380* | −1.520397355 | −1.777139274 | −1.687490212 | −1.661675613 | II |
| 123 | HM-01 | K9 | hsa-miR-148a | −1.685567485 | −1.676518937 | −1.612944096 | −1.658343506 | II |
| 124 | HM-05 | O1 | hsa-miR-4712-3p | −1.777491867 | −1.594477002 | −1.587828142 | −1.653265671 | II |
| 125 | HM-04 | A11 | hsa-miR-3680 | −1.925490304 | −1.268164771 | −1.76192918 | −1.651861418 | II |
| 126 | HM-03 | E14 | hsa-miR-1206 | −1.696381544 | −1.63978279 | −1.613348859 | −1.649837731 | II |
| 127 | HM-04 | N16 | hsa-miR-4520a-3p | −1.778069104 | −1.423621713 | −1.743393645 | −1.648361487 | II |
| 128 | HM-01 | B2 | hsa-miR-552 | −1.584268445 | −1.741632939 | −1.60651749 | −1.644139624 | II |
| 129 | HM-03 | K1 | hsa-miR-1272 | −1.694589471 | −1.567000257 | −1.669335525 | −1.643641751 | II |
| 130 | HM-02 | J10 | hsa-miR-629 | −1.558801392 | −1.62615586 | −1.703902344 | −1.629619865 | II |
| 131 | HM-03 | B6 | hsa-miR-3154 | −1.647659209 | −1.557705192 | −1.668314568 | −1.624559656 | II |
| 132 | HM-01 | C15 | hsa-miR-302b | −1.602368744 | −1.757831191 | −1.492617293 | −1.617605743 | II |
| 133 | HM-01 | B4 | hsa-miR-588 | −1.564350804 | −1.737379799 | −1.546223392 | −1.615984665 | II |
| 134 | HM-05 | P1 | hsa-miR-4772-5p | −1.840629054 | −1.600305645 | −1.395601918 | −1.612178872 | II |
| 135 | HM-01 | O1 | hsa-miR-520g | −1.259415042 | −1.857057367 | −1.69604212 | −1.60417151 | II |
| 136 | HM-04 | F9 | hsa-miR-4720-3p | −1.568311643 | −1.600331328 | −1.610291866 | −1.592978279 | II |
| 137 | HM-01 | D17 | hsa-miR-373 | −1.55360632 | −1.77477107 | −1.436333697 | −1.588237029 | II |
| 138 | HM-05 | C9 | hsa-miR-4743 | −1.811794488 | −1.55620184 | −1.395384293 | −1.58778642 | II |
| 139 | HM-01 | M18 | hsa-miR-432* | −1.768246943 | −1.474648831 | −1.517179906 | −1.586691893 | II |
| 140 | HM-01 | J18 | hsa-miR-659 | −1.597783279 | −1.504691885 | −1.638210314 | −1.580228493 | II |
| 141 | HM-01 | B5 | hsa-miR-302a | −1.430569686 | −1.676749531 | −1.6088655 | −1.572061572 | II |
| 142 | HM-05 | N5 | hsa-miR-4712-5p | −1.567159209 | −1.651888864 | −1.478578621 | −1.565878515 | II |
| 143 | HM-01 | C10 | hsa-miR-507 | −1.483456453 | −1.534974494 | −1.639617633 | −1.55268286 | II |
| 144 | HM-05 | C14 | hsa-miR-1587 | −1.556551115 | −1.553473358 | −1.511133924 | −1.540386132 | II |
| 145 | HM-02 | H12 | hsa-let-7g* | −1.428613419 | −1.505027007 | −1.651477618 | −1.528372681 | II |
| 146 | HM-04 | P3 | hsa-miR-3545-5p | −0.909042123 | −1.693259223 | −1.972924854 | −1.5250754 | II |
| 147 | HM-01 | E12 | hsa-miR-302c | −1.383009759 | −1.667194691 | −1.520812736 | −1.523672396 | II |
| 148 | HM-02 | O1 | hsa-miR-193b | −1.594628508 | −1.542473737 | −1.433779137 | −1.523627127 | II |
| 149 | HM-04 | I11 | hsa-miR-3657 | −1.514639405 | −1.429552837 | −1.623115155 | −1.522435799 | II |
| 150 | HM-03 | H1 | hsa-miR-3147 | −1.487384969 | −1.51080409 | −1.508600021 | −1.502263027 | II |
| 151 | HM-05 | E18 | hsa-miR-4493 | −1.558707142 | −1.706269557 | −1.197392644 | −1.487463114 | II |
| 152 | HM-01 | B3 | hsa-miR-302d | −1.090645045 | −1.766887607 | −1.504676583 | −1.454069745 | II |
| 153 | HM-03 | K20 | hsa-miR-2113 | −1.532122284 | −1.572570408 | −1.215015698 | −1.439902797 | II |
| 154 | HM-01 | A15 | hsa-miR-378* | −1.185140507 | −1.621978195 | −1.509964841 | −1.439027848 | II |
| 155 | HM-05 | E15 | hsa-miR-4730 | −1.643997667 | −1.189844918 | −1.47234641 | −1.435396332 | II |
| 156 | HM-05 | N1 | hsa-miR-4765 | −1.447294738 | −1.359807753 | −1.480068322 | −1.429056938 | II |
| 157 | HM-05 | E10 | hsa-miR-4713-5p | −1.802122273 | −1.332325831 | −1.147632357 | −1.427360154 | II |
| 158 | HM-05 | D9 | hsa-miR-2467-3p | −1.401571121 | −1.491315344 | −1.38160198 | −1.424829482 | II |
| 159 | HM-03 | F10 | hsa-miR-3119 | −1.359753318 | −1.428289103 | −1.478875667 | −1.422289137 | II |
| 160 | HM-04 | K8 | hsa-miR-3605-3p | −1.448146221 | −1.324419002 | −1.462324836 | −1.41163002 | II |
| 161 | HM-02 | F11 | hsa-miR-193b* | −1.411728093 | −1.37006378 | −1.44523663 | −1.409009501 | II |
| 162 | HM-01 | G11 | hsa-miR-297 | −1.269425704 | −1.694175156 | −1.240070817 | −1.401223892 | II |
| 163 | HM-04 | H16 | hsa-miR-4487 | −1.54539505 | −1.164388998 | −1.490416573 | −1.400066874 | II |
| 164 | HM-02 | P4 | hsa-miR-541 | −1.420007095 | −1.276917498 | −1.502226138 | −1.39971691 | II |

TABLE 2-continued

| Number | Plate | Well | miRNA | Robust Z-score | | | Average Robust '- score | Rank |
|---|---|---|---|---|---|---|---|---|
| | | | | Replicate 1 | Replicate 2 | Replicate 3 | | |
| 165 | HM-03 | P19 | hsa-miR-3139 | −1.497396598 | −1.402817389 | −1.287268411 | −1.395827466 | II |
| 166 | HM-02 | O19 | hsa-miR-17 | −1.484538402 | −1.079581255 | −1.597718354 | −1.387279337 | II |
| 167 | HM-02 | G3 | hsa-miR-526b* | −1.399441154 | −1.715143219 | −1.042694215 | −1.385759529 | II |
| 168 | HM-05 | J13 | hsa-miR-4667-3p | −1.214125607 | −1.583272782 | −1.324311417 | −1.373903262 | II |
| 169 | HM-04 | C10 | hsa-miR-3680* | −1.347659375 | −1.35197462 | −1.421075503 | −1.373569833 | II |
| 170 | HM-03 | A20 | hsa-miR-1288 | −1.285111741 | −1.37001816 | −1.430848116 | −1.361992672 | II |
| 171 | HM-04 | C1 | hsa-miR-3163 | −1.136557015 | −1.320101415 | −1.628998457 | −1.361885629 | II |
| 172 | HM-02 | I16 | hsa-miR-422a | −1.317537724 | −1.332041502 | −1.426595594 | −1.35872494 | II |
| 173 | HM-03 | I13 | hsa-miR-1269 | −1.660390126 | −0.975129764 | −1.435591988 | −1.357037293 | II |
| 174 | HM-04 | A15 | hsa-miR-544b | −1.337852723 | −1.298467413 | −1.42950295 | −1.355274362 | II |
| 175 | HM-05 | C7 | hsa-miR-4781-3p | −1.547573331 | −1.386263803 | −1.121460658 | −1.351765931 | II |
| 176 | HM-01 | A20 | hsa-miR-18b | −1.282276019 | −1.44853586 | −1.31083038 | −1.347214086 | II |
| 177 | HM-02 | O12 | hsa-miR-144* | −1.188867661 | −1.4892187 | −1.363052218 | −1.347046193 | II |
| 178 | HM-03 | M16 | hsa-miR-2116 | −1.381207577 | −1.354168475 | −1.29608192 | −1.343819324 | II |
| 179 | HM-05 | J21 | hsa-miR-4731-5p | −1.366062116 | −1.308168194 | −1.345148647 | −1.339792986 | II |
| 180 | HM-03 | O19 | hsa-miR-1282 | −1.511772127 | −1.402798368 | −1.102380305 | −1.3389836 | II |
| 181 | HM-05 | F18 | hsa-miR-378i | −1.343647297 | −1.300490241 | −1.353842172 | −1.332659903 | II |
| 182 | HM-04 | B11 | hsa-miR-4802-5p | −1.389402137 | −1.202989177 | −1.399358572 | −1.330583295 | II |
| 183 | HM-01 | H14 | hsa-miR-637 | −1.150278182 | −1.509963723 | −1.309028449 | −1.323090118 | II |
| 184 | HM-03 | D4 | hsa-miR-3162 | −1.124648686 | −1.415718936 | −1.426208651 | −1.322192091 | II |
| 185 | HM-03 | N11 | hsa-miR-3187 | −1.22734619 | −1.487364976 | −1.241760302 | −1.318823829 | II |
| 186 | HM-04 | H20 | hsa-miR-4687-3p | −1.224867473 | −1.233764055 | −1.497187218 | −1.318606249 | II |
| 187 | HM-01 | M12 | hsa-miR-517c | −1.300833686 | −1.454263758 | −1.187234623 | −1.314110689 | II |
| 188 | HM-03 | M21 | hsa-miR-1208 | −1.463997305 | −1.448994115 | −1.026416569 | −1.313135996 | II |
| 189 | HM-01 | J13 | hsa-miR-330-5p | −1.283836985 | −1.240257056 | −1.415200713 | −1.313098252 | II |
| 190 | HM-03 | C5 | hsa-miR-1250 | −1.478946374 | −1.214561084 | −1.239019443 | −1.3108423 | II |
| 191 | HM-02 | D7 | hsa-miR-92a-1* | −1.385245613 | −1.152628014 | −1.387921674 | −1.308598434 | II |
| 192 | HM-02 | M1 | hsa-miR-454 | −1.077560809 | −1.398563052 | −1.412476631 | −1.296200164 | II |
| 193 | HM-03 | E10 | hsa-miR-1178 | −1.243383173 | −1.362273832 | −1.273192411 | −1.292949807 | II |
| 194 | HM-01 | P19 | hsa-miR-654-5p | −1.338823114 | −1.463997866 | −1.073633011 | −1.29215133 | II |
| 195 | HM-02 | I19 | hsa-miR-183* | −1.365072397 | −1.186073239 | −1.312082842 | −1.287742826 | II |
| 196 | HM-02 | B5 | hsa-miR-517a | −1.283377059 | −1.235687593 | −1.338089647 | −1.2857181 | II |
| 197 | HM-05 | J4 | hsa-miR-4781-5p | −1.45106976 | −1.137406706 | −1.263425207 | −1.283967224 | II |
| 198 | HM-03 | L6 | hsa-miR-3175 | −1.240971006 | −1.288310209 | −1.31096435 | −1.280081855 | II |
| 199 | HM-05 | C17 | hsa-miR-4740-5p | −1.270966305 | −1.350400061 | −1.213246686 | −1.278204351 | II |
| 200 | HM-03 | E16 | hsa-miR-1180 | −1.219134583 | −1.246184494 | −1.368010836 | −1.277776638 | II |
| 201 | HM-03 | D3 | hsa-miR-4313 | −1.373577136 | −1.181247757 | −1.278153552 | −1.277659481 | II |
| 202 | HM-02 | J16 | hsa-miR-145* | −1.270146605 | −1.229010701 | −1.33213918 | −1.277098829 | II |
| 203 | HM-05 | H18 | hsa-miR-4460 | −1.371188167 | −1.266605574 | −1.185725931 | −1.274506557 | II |
| 204 | HM-02 | I22 | hsa-miR-489 | −1.238261589 | −1.104696415 | −1.470820799 | −1.271259601 | II |
| 205 | HM-03 | E3 | hsa-miR-1256 | −1.337352325 | −1.104764166 | −1.355231654 | −1.265782715 | II |
| 206 | HM-04 | B17 | hsa-miR-4435 | −1.311727573 | −1.221795498 | −1.249863953 | −1.261129008 | II |
| 207 | HM-03 | D2 | hsa-miR-378b | −1.215027549 | −1.273919473 | −1.289120553 | −1.259355859 | II |
| 208 | HM-04 | B21 | hsa-miR-3975 | −1.35155776 | −1.27809592 | −1.134487665 | −1.254713782 | II |
| 209 | HM-05 | C8 | hsa-miR-3972 | −1.222902861 | −1.198012866 | −1.338446536 | −1.253120754 | II |
| 210 | HM-04 | P17 | hsa-miR-4665-5p | −1.280320688 | −1.161482474 | −1.301847344 | −1.247883402 | II |
| 211 | HM-05 | B10 | hsa-miR-4779 | −1.195896564 | −1.435176082 | −1.106535291 | −1.245869312 | II |
| 212 | HM-04 | C13 | hsa-miR-3136 | −1.088771612 | −1.223550662 | −1.403485424 | −1.238602566 | II |
| 213 | HM-01 | N18 | hsa-miR-555 | −1.364945043 | −1.170447086 | −1.165792816 | −1.233728315 | II |
| 214 | HM-04 | P16 | hsa-miR-378h | −1.186490874 | −1.18377722 | −1.330017357 | −1.233428484 | II |
| 215 | HM-04 | E21 | hsa-miR-3665 | −1.353545512 | −1.077956043 | −1.265957419 | −1.232486325 | II |
| 216 | HM-05 | N11 | hsa-miR-4677-3p | −1.173230641 | −1.423086146 | −1.086812158 | −1.227709648 | II |
| 217 | HM-03 | K13 | hsa-miR-1202 | −1.327439134 | −1.180891862 | −1.173756229 | −1.227362408 | II |
| 218 | HM-03 | J7 | hsa-miR-3118 | −1.188627079 | −1.269780778 | −1.219380876 | −1.225929578 | II |
| 219 | HM-01 | G7 | hsa-miR-132 | −0.92460311 | −1.380564484 | −1.350843662 | −1.218670419 | II |
| 220 | HM-05 | F12 | hsa-miR-4644 | −1.084459549 | −1.547512948 | −1.004916106 | −1.212296201 | II |
| 221 | HM-02 | P15 | hsa-miR-148b* | −1.082018906 | −1.25539874 | −1.285550079 | −1.207655909 | II |
| 222 | HM-02 | H15 | hsa-miR-93* | −1.135302501 | −1.243667655 | −1.24384973 | −1.207605229 | II |
| 223 | HM-02 | F22 | hsa-miR-519d | −1.327189365 | −0.917613947 | −1.376973225 | −1.207258846 | II |
| 224 | HM-01 | D10 | hsa-miR-491-5p | −1.040460343 | −1.35086467 | −1.228951774 | −1.206758929 | II |
| 225 | HM-02 | L5 | hsa-miR-628-5p | −1.079242909 | −1.326319432 | −1.208950193 | −1.204837511 | II |
| 226 | HM-04 | A14 | hsa-miR-3691 | −1.477035074 | −0.849946989 | −1.272486866 | −1.199822976 | II |
| 227 | HM-02 | L3 | hsa-miR-338-5p | −1.215276292 | −1.222582665 | −1.159123527 | −1.199094162 | II |
| 228 | HM-03 | C13 | hsa-miR-664* | −1.291522468 | −1.086253149 | −1.217513716 | −1.198429778 | II |
| 229 | HM-02 | F18 | hsa-miR-18a | −1.175333977 | −1.25774601 | −1.148691332 | −1.193923773 | II |
| 230 | HM-01 | A9 | hsa-miR-328 | −1.135526479 | −1.321266155 | −1.123025813 | −1.193272816 | II |
| 231 | HM-05 | E2 | hsa-miR-3688-5p | −1.411953882 | −1.211711296 | −0.955623322 | −1.193096133 | II |
| 232 | HM-01 | B13 | hsa-miR-93 | −1.058243512 | −1.393525437 | −1.125702357 | −1.192490436 | II |
| 233 | HM-01 | K8 | hsa-miR-34b* | −1.423108568 | −1.120164311 | −1.022091602 | −1.188454827 | II |
| 234 | HM-04 | K3 | hsa-miR-3689a-5p | −1.118209872 | −1.31140185 | −1.118796636 | −1.182802786 | II |
| 235 | HM-05 | G2 | hsa-miR-2682* | −1.360571124 | −0.852189242 | −1.326533565 | −1.179764643 | II |
| 236 | HM-03 | I17 | hsa-miR-1238 | −1.357641402 | −1.323043951 | −0.844459903 | −1.175048419 | II |
| 237 | HM-02 | E4 | hsa-miR-323b-5p | −1.391627809 | −0.937644984 | −1.191396923 | −1.173556572 | II |
| 238 | HM-01 | G8 | hsa-miR-493* | −1.160359142 | −1.233789681 | −1.109892563 | −1.168013796 | II |
| 239 | HM-01 | K15 | hsa-miR-517b | −1.177343754 | −1.108480924 | −1.214090505 | −1.166638394 | II |
| 240 | HM-04 | C6 | hsa-miR-3679-3p | −1.387295688 | −1.037371736 | −1.070314968 | −1.164994131 | II |

TABLE 2-continued

| Number | Plate | Well | miRNA | Robust Z-score Replicate 1 | Replicate 2 | Replicate 3 | Average Robust '-score | Rank |
|---|---|---|---|---|---|---|---|---|
| 241 | HM-03 | B16 | hsa-miR-3137 | −1.094834636 | −1.093548932 | −1.304853437 | −1.164412335 | II |
| 242 | HM-01 | J14 | hsa-miR-425 | −0.944496222 | −1.274817794 | −1.266263058 | −1.161859025 | II |
| 243 | HM-05 | O10 | hsa-miR-4474-3p | −0.993292889 | −1.231903964 | −1.252376553 | −1.159191135 | II |
| 244 | HM-04 | F2 | hsa-miR-4745-3p | −1.276108071 | −1.034729318 | −1.155587673 | −1.155475021 | II |
| 245 | HM-03 | J1 | hsa-miR-3199 | −1.198666646 | −1.090629941 | −1.165965865 | −1.15175415 | II |
| 246 | HM-04 | P18 | hsa-miR-4445 | −1.105536099 | −1.203307116 | −1.144197158 | −1.151013458 | II |
| 247 | HM-04 | E17 | hsa-miR-3607-5p | −1.484007296 | −0.95882992 | −1.008695693 | −1.15051097 | II |
| 248 | HM-04 | D1 | hsa-miR-4680-5p | −1.127749775 | −1.084474638 | −1.238753936 | −1.150326116 | II |
| 249 | HM-02 | F17 | hsa-miR-450b-3p | −1.193375887 | −1.068563273 | −1.172692119 | −1.144877093 | II |
| 250 | HM-03 | C4 | hsa-miR-1207-5p | −1.120420134 | −1.30923899 | −1.000937198 | −1.143532107 | II |
| 251 | HM-04 | L12 | hsa-miR-4524 | −0.884573273 | −1.21178866 | −1.317355534 | −1.137905822 | II |
| 252 | HM-03 | F12 | hsa-miR-3160 | −1.249651168 | −1.097053187 | −1.066743142 | −1.137815832 | II |
| 253 | HM-02 | F1 | hsa-miR-202 | −1.025775063 | −1.162377922 | −1.209386215 | −1.132513066 | II |
| 254 | HM-03 | A16 | hsa-miR-1286 | −1.147289383 | −1.268508915 | −0.980108888 | −1.131969062 | II |
| 255 | HM-01 | A21 | hsa-miR-20a | −0.884025363 | −1.354738918 | −1.144591712 | −1.127785331 | II |
| 256 | HM-01 | C5 | hsa-miR-106b | −1.268143974 | −1.12797139 | −0.983898786 | −1.126671383 | II |
| 257 | HM-01 | K18 | hsa-miR-433 | −1.355095375 | −0.986691786 | −1.031373869 | −1.12438701 | II |
| 258 | HM-03 | I15 | hsa-miR-1270 | −1.125546387 | −1.147818233 | −1.077680237 | −1.117014952 | II |
| 259 | HM-02 | E13 | hsa-miR-758 | −1.238321309 | −1.262286508 | −0.848456898 | −1.116354905 | II |
| 280 | HM-05 | O20 | hsa-miR-4684-3p | −1.025948878 | −1.188650148 | −1.127461927 | −1.114020318 | II |
| 261 | HM-02 | B22 | hsa-miR-23b* | −1.220144573 | −1.042264005 | −1.077411926 | −1.113273405 | II |
| 262 | HM-03 | L18 | hsa-miR-3184 | −1.317174415 | −1.221184756 | −0.799806609 | −1.112721927 | II |
| 263 | HM-01 | E15 | hsa-miR-153 | −0.828489955 | −1.253444548 | −1.254289908 | −1.112074804 | II |
| 264 | HM-01 | E22 | hsa-miR-296-5p | −1.151447043 | −1.184835321 | −0.991354676 | −1.109212347 | II |
| 265 | HM-02 | K19 | hsa-miR-579 | −0.970488618 | −1.039251418 | −1.311423239 | −1.107054425 | II |
| 266 | HM-02 | L7 | hsa-miR-132* | −0.83114844 | −1.10186601 | −1.387614353 | −1.106876268 | II |
| 267 | HM-01 | B20 | hsa-miR-31 | −0.982560346 | −1.031367972 | −1.290194993 | −1.101374437 | II |
| 268 | HM-01 | I10 | hsa-miR-124* | −0.710146195 | −1.274597282 | −1.317416065 | −1.100719847 | II |
| 269 | HM-02 | F6 | hsa-miR-129* | −1.073899428 | −1.045044634 | −1.183128837 | −1.100690966 | II |
| 270 | HM-05 | K6 | hsa-miR-4684-5p | −1.166629134 | −1.187919726 | −0.944684684 | −1.099744515 | II |
| 271 | HM-04 | C14 | hsa-miR-3934 | −1.100830705 | −1.142353293 | −1.049194012 | −1.097459337 | II |
| 272 | HM-05 | D10 | hsa-miR-4659b-3p | −1.286303319 | −1.140064745 | −0.861570133 | −1.095979399 | II |
| 273 | HM-04 | L15 | hsa-miR-4502 | −1.025762102 | −0.970681348 | −1.289606391 | −1.095349947 | II |
| 274 | HM-04 | K9 | hsa-miR-3943 | −1.019378809 | −1.14328679 | −1.115748787 | −1.092804795 | II |
| 275 | HM-02 | G14 | hsa-miR-452 | −0.881739934 | −1.204455443 | −1.191709594 | −1.09263499 | II |
| 276 | HM-03 | O6 | hsa-miR-2117 | −1.001757239 | −1.182220457 | −1.092721915 | −1.092233204 | II |
| 277 | HM-04 | L7 | hsa-miR-4703-3p | −1.09738902 | −1.056706726 | −1.113488195 | −1.089194647 | II |
| 278 | HM-05 | H9 | hsa-miR-4430 | −1.111587906 | −0.893050578 | −1.255501887 | −1.086713457 | II |
| 279 | HM-01 | C2 | hsa-miR-497 | −0.674789253 | −1.32967805 | −1.229311933 | −1.077926412 | II |
| 280 | HM-02 | F20 | hsa-miR-892b | −1.148617767 | −1.13385003 | −0.94934178 | −1.077269859 | II |
| 281 | HM-04 | G9 | hsa-miR-3150b | −1.063555397 | −0.970448917 | −1.190911511 | −1.074971942 | II |
| 282 | HM-04 | I14 | hsa-miR-3922 | −1.12492918 | −1.021533189 | −1.076494065 | −1.074318811 | II |
| 283 | HM-01 | C8 | hsa-miR-130a | −0.964601368 | −1.219118048 | −1.027680705 | −1.070466707 | II |
| 284 | HM-04 | I19 | hsa-miR-3682 | −0.619152798 | −1.322908575 | −1.247079584 | −1.063046986 | II |
| 285 | HM-02 | D5 | hsa-miR-185* | −1.039055739 | −1.02613659 | −1.118870563 | −1.061354297 | II |
| 286 | HM-02 | O8 | hsa-miR-29b-2* | −0.972879942 | −1.069015579 | −1.122826027 | −1.05490711 | II |
| 287 | HM-05 | I11 | hsa-miR-4693-3p | −1.116181077 | −0.888204035 | −1.159619074 | −1.054668062 | II |
| 288 | HM-03 | J2 | hsa-miR-3155 | −0.933797528 | −1.482904342 | −0.736624572 | −1.051108814 | II |
| 289 | HM-05 | L21 | hsa-miR-4664-3p | −1.052304301 | −1.095809931 | −0.985660336 | −1.044591523 | II |
| 290 | HM-01 | C13 | hsa-miR-129-3p | −1.055142169 | −1.153338665 | −0.913694161 | −1.040724998 | II |
| 291 | HM-05 | F22 | hsa-miR-4784 | −1.021083282 | −1.011052716 | −1.077458984 | −1.036531661 | II |
| 292 | HM-02 | N18 | hsa-miR-450b-5p | −0.888674809 | −1.099264674 | −1.119697663 | −1.035879048 | II |
| 293 | HM-05 | P17 | hsa-miR-3064-3p | −1.139759519 | −0.962084355 | −1.004911829 | −1.035585234 | II |
| 294 | HM-04 | H6 | hsa-miR-4642 | −1.153915062 | −0.904978809 | −1.047219701 | −1.035371191 | II |
| 295 | HM-01 | D14 | hsa-miR-601 | −0.901755641 | −1.168689721 | −1.032944298 | −1.03446322 | II |
| 296 | HM-05 | B18 | hsa-miR-4669 | −1.230783691 | −1.07215434 | −0.795668319 | −1.032868783 | II |
| 297 | HM-02 | N3 | hsa-miR-636 | −0.955413675 | −1.118312405 | −1.020848617 | −1.031524899 | II |
| 298 | HM-02 | E6 | hsa-miR-30c-1* | −1.069665177 | −0.962341465 | −1.03901474 | −1.023673794 | II |
| 299 | HM-05 | F3 | hsa-miR-4708-3p | −0.988783075 | −1.031756623 | −1.046895238 | −1.022478312 | II |
| 300 | HM-01 | H3 | hsa-miR-193a-3p | −1.301444837 | −0.657739758 | −1.106828162 | −1.022004253 | II |
| 301 | HM-02 | O10 | hsa-miR-483-5p | −0.809976074 | −1.092644808 | −1.141888248 | −1.014836377 | II |
| 302 | HM-05 | G1 | hsa-miR-378d | −1.384496728 | −0.669844089 | −0.988980124 | −1.014440314 | II |
| 303 | HM-05 | C5 | hsa-miR-3545-3p | −0.97011928 | −1.004222808 | −1.060891713 | −1.0117446 | II |
| 304 | HM-02 | A14 | hsa-miR-29b-1* | −1.025156769 | −0.916764702 | −1.08057302 | −1.007498164 | II |
| 305 | HM-04 | A16 | hsa-miR-3664 | −1.089211288 | −0.97115098 | −0.96075813 | −1.007040133 | II |
| 306 | HM-05 | I3 | hsa-miR-4505 | −1.013741677 | −0.847818275 | −1.149163501 | −1.003574484 | II |
| 307 | HM-05 | N17 | hsa-miR-4515 | −0.9003029 | −1.148833999 | −0.960477812 | −1.003204904 | II |
| 308 | HM-05 | I7 | hsa-miR-4788 | −0.99369584 | −0.841570117 | −1.173729167 | −1.002998375 | II |
| 309 | HM-05 | I5 | hsa-miR-4681 | −0.884680093 | −1.001658271 | −1.120048861 | −1.002129075 | II |
| 310 | HM-04 | L11 | hsa-miR-4459 | −1.146487816 | −0.715485926 | −1.133351247 | −0.998441663 | III |
| 311 | HM-02 | I8 | hsa-miR-326 | −0.947064699 | −1.013210351 | −1.032601301 | −0.99762545 | III |
| 312 | HM-04 | D16 | hsa-miR-4749-5p | −1.022527441 | −0.934103755 | −1.035107068 | −0.997246088 | III |
| 313 | HM-04 | B5 | hsa-miR-4718 | −0.925052514 | −0.931411117 | −1.131021322 | −0.995828318 | III |
| 314 | HM-02 | L2 | hsa-miR-744* | −0.928262257 | −1.049704579 | −0.986277669 | −0.988081502 | III |
| 315 | HM-01 | M10 | hsa-miR-195 | −1.103294622 | −0.960512647 | −0.900202808 | −0.988003359 | III |
| 316 | HM-01 | N3 | hsa-miR-646 | −1.038977971 | −0.977094423 | −0.928127838 | −0.981400077 | III |

TABLE 2-continued

| Number | Plate | Well | miRNA | Robust Z-score Replicate 1 | Replicate 2 | Replicate 3 | Average Robust '-score | Rank |
|---|---|---|---|---|---|---|---|---|
| 317 | HM-04 | D9 | hsa-miR-4432 | −0.953899734 | −0.999110652 | −0.971080045 | −0.97469681 | III |
| 318 | HM-02 | K17 | hsa-miR-671-3p | −1.010065401 | −1.090100705 | −0.823382982 | −0.974516363 | III |
| 319 | HM-01 | O14 | hsa-miR-199a-5p | −1.105691194 | −0.973409941 | −0.840963165 | −0.973354767 | III |
| 320 | HM-04 | H17 | hsa-miR-4688 | −1.177183421 | −0.767090917 | −0.9563529 | −0.966875746 | III |
| 321 | HM-03 | C14 | hsa-miR-1206 | −1.033710826 | −0.898936235 | −0.965450253 | −0.966032438 | III |
| 322 | HM-02 | B16 | hsa-miR-510 | −1.162353311 | −0.858587347 | −0.870831334 | −0.963923998 | III |
| 323 | HM-01 | P13 | hsa-miR-557 | −0.933790849 | −1.032828875 | −0.924918061 | −0.963845928 | III |
| 324 | HM-03 | P12 | hsa-miR-3176 | −1.099027698 | −0.95036835 | −0.840574737 | −0.963323595 | III |
| 325 | HM-03 | D1 | hsa-miR-3131 | −0.901557092 | −1.092808326 | −0.894860886 | −0.963075435 | III |
| 326 | HM-02 | P5 | hsa-miR-149* | −0.762397657 | −0.91890423 | −1.207820626 | −0.963040838 | III |
| 327 | HM-02 | H10 | hsa-miR-486-3p | −1.109340865 | −0.72392094 | −1.048641769 | −0.960634525 | III |
| 328 | HM-05 | C18 | hsa-miR-3942-3p | −0.836971141 | −1.140712487 | −0.903241404 | −0.960308344 | III |
| 329 | HM-05 | D4 | hsa-miR-4436a | −1.047597278 | −0.916150446 | −0.913559024 | −0.959102249 | III |
| 330 | HM-05 | O11 | hsa-miR-4518 | −0.900373586 | −0.949009605 | −1.013809487 | −0.954397559 | III |
| 331 | HM-01 | F21 | hsa-miR-410 | −0.837858483 | −1.128995226 | −0.887269242 | −0.951374317 | III |
| 332 | HM-03 | J14 | hsa-miR-4321 | −1.064132141 | −0.887201559 | −0.898763352 | −0.950032351 | III |
| 333 | HM-04 | N13 | hsa-miR-4800-5p | −1.129367947 | −0.812758195 | −0.907433882 | −0.949853341 | III |
| 334 | HM-01 | D8 | hsa-miR-642a | −0.885675195 | −1.002613361 | −0.9528775 | −0.947055352 | III |
| 335 | HM-04 | L9 | hsa-miR-4715-5p | −0.879220472 | −0.975021192 | −0.980618258 | −0.944953307 | III |
| 336 | HM-02 | L18 | hsa-miR-576-3p | −0.846767046 | −0.802403672 | −1.178640245 | −0.942603654 | III |
| 337 | HM-05 | L9 | hsa-miR-4650-5p | −1.063771164 | −0.916588576 | −0.839626848 | −0.939988868 | III |
| 338 | HM-03 | E22 | hsa-miR-1908 | −0.929251765 | −0.930531859 | −0.955240692 | −0.938341438 | III |
| 339 | HM-04 | N14 | hsa-miR-4728-5p | −0.594333545 | −1.17364633 | −1.04663568 | −0.938205185 | III |
| 340 | HM-05 | M8 | hsa-miR-4782-3p | −0.855326107 | −0.946258629 | −1.004987819 | −0.935524185 | III |
| 341 | HM-05 | E19 | hsa-miR-4507 | −0.913761887 | −1.14195252 | −0.749545447 | −0.935086618 | III |
| 342 | HM-05 | J7 | hsa-miR-4439 | −1.082993264 | −0.656999358 | −1.048679816 | −0.929557479 | III |
| 343 | HM-05 | D20 | hsa-miR-4750 | −0.956539449 | −0.873692746 | −0.951411549 | −0.927214581 | III |
| 344 | HM-04 | K2 | hsa-miR-3925 | −0.749655355 | −0.94891974 | −1.081829424 | −0.926801506 | III |
| 345 | HM-02 | O22 | hsa-miR-30c-2* | −0.968719134 | −0.906139703 | −0.903902953 | −0.92625393 | III |
| 346 | HM-05 | A3 | hsa-miR-4427 | −0.758674518 | −0.806152995 | −1.213920018 | −0.926249177 | III |
| 347 | HM-02 | C15 | hsa-miR-769-3p | −1.017032761 | −0.840256043 | −0.908061291 | −0.921783365 | III |
| 348 | HM-05 | L7 | hsa-miR-4725-5p | −0.97397926 | −0.917403757 | −0.861009367 | −0.917464128 | III |
| 349 | HM-02 | E18 | hsa-miR-185 | −1.324894543 | −0.945312244 | −0.475664481 | −0.915290423 | III |
| 350 | HM-02 | F4 | hsa-miR-885-5p | −0.987142774 | −0.987374692 | −0.766139667 | −0.913552341 | III |
| 351 | HM-03 | F15 | hsa-miR-3138 | −0.875209755 | −0.963779511 | −0.89826011 | −0.912416459 | III |
| 352 | HM-02 | A12 | hsa-miR-504 | −0.906857148 | −0.862071794 | −0.957350274 | −6.908759739 | III |
| 353 | HM-02 | E12 | hsa-miR-653 | −0.923649715 | −0.869512415 | −0.918711012 | −0.903957714 | III |
| 354 | HM-05 | K21 | hsa-miR-4672 | −0.991309957 | −1.028147183 | −0.691771377 | −0.903742839 | III |
| 355 | HM-01 | P3 | hsa-miR-411 | −0.703811073 | −1.078304918 | −0.923850439 | −0.90198881 | III |
| 356 | HM-03 | G19 | hsa-miR-1236 | −0.646751716 | −1.015216849 | −1.016043162 | −0.892670576 | III |
| 357 | HM-01 | K20 | hsa-miR-130b | −0.857689519 | −0.842884656 | −0.975768505 | −0.892114227 | III |
| 358 | HM-02 | A21 | hsa-miR-22* | −0.969795022 | −0.836465618 | −0.864442191 | −0.890234277 | III |
| 359 | HM-03 | A18 | hsa-miR-1287 | −0.953259671 | −0.734633008 | −0.980239914 | −0.889377531 | III |
| 360 | HM-05 | H7 | hsa-miR-4699-5p | −0.910566737 | −0.654409301 | −1.090011155 | −0.884995731 | III |
| 361 | HM-02 | A3 | hsa-miR-556-5p | −1.023995857 | −0.754801886 | −0.863727922 | −0.880841888 | III |
| 362 | HM-01 | A18 | hsa-miR-192 | −0.67135344 | −1.045721469 | −0.919317648 | −0.878797519 | III |
| 363 | HM-04 | G5 | hsa-miR-3675-3p | −0.850749479 | −0.799505385 | −0.979403561 | −0.876552808 | III |
| 364 | HM-04 | J16 | hsa-miR-378e | −0.841202287 | −0.852803271 | −0.930850808 | −0.874952122 | III |
| 365 | HM-03 | G1 | hsa-miR-1183 | −0.847763677 | −0.566855871 | −1.208651207 | −0.874423585 | III |
| 366 | HM-04 | C22 | hsa-miR-3678-5p | −0.854098506 | −0.824821595 | −0.930719906 | −0.86987967 | III |
| 367 | HM-03 | N9 | hsa-miR-3180-3p | −0.958960193 | −0.789761374 | −0.854467965 | −0.867729844 | III |
| 368 | HM-01 | D22 | hsa-miR-604 | −0.822047193 | −0.99560758 | −0.778398986 | −0.865351253 | III |
| 369 | HM-04 | J8 | hsa-miR-3677-5p | −0.670712845 | −0.89346009 | −1.025877798 | −0.863350244 | III |
| 370 | HM-04 | L9 | hsa-miR-183 | −0.709191245 | −1.033512344 | −0.846267103 | −0.863010231 | III |
| 371 | HM-01 | J3 | hsa-miR-423-5p | −0.986016605 | −1.000500896 | −0.600197043 | −0.862238182 | III |
| 372 | HM-02 | K18 | hsa-miR-378 | −0.7934869 | −0.878267812 | −0.914716138 | −0.86215695 | III |
| 373 | HM-05 | M21 | hsa-miR-4520b-3p | −0.881249215 | −0.874729117 | −0.829890736 | −0.861956356 | III |
| 374 | HM-04 | D7 | hsa-miR-4639-3p | −0.858424964 | −0.936156379 | −0.789939121 | −0.861506821 | III |
| 375 | HM-03 | D18 | hsa-miR-3124 | −0.965271069 | −0.836663926 | −0.780137346 | −0.86069078 | III |
| 376 | HM-03 | E18 | hsa-miR-1304 | −0.965271069 | −0.836663926 | −0.780137346 | −0.86069078 | III |
| 377 | HM-04 | L6 | hsa-miR-3913-3p | −0.671182679 | −0.934769788 | −0.969982129 | −0.858644865 | III |
| 378 | HM-03 | C16 | hsa-miR-1295 | −0.843165669 | −0.962181939 | −0.76499644 | −0.856781349 | III |
| 379 | HM-01 | K6 | hsa-miR-24 | −0.968730443 | −0.982887939 | −0.614050897 | −0.855223093 | III |
| 380 | HM-01 | H21 | hsa-miR-708 | −1.047094727 | −0.255578585 | −1.261409558 | −0.85469429 | III |
| 381 | HM-01 | M11 | hsa-miR-212 | −0.894030557 | −0.807633909 | −0.847769601 | −0.849811356 | III |
| 382 | HM-04 | B6 | hsa-miR-4693-5p | −0.84057038 | −0.703894417 | −0.991756183 | −0.845406993 | III |
| 383 | HM-02 | C19 | hsa-miR-766 | −0.85307092 | −0.906454938 | −0.770003376 | −0.843176411 | III |
| 384 | HM-04 | L17 | hsa-miR-4683 | −0.826371333 | −0.789306965 | −0.906891262 | −0.84085652 | III |
| 385 | HM-04 | M5 | hsa-miR-3939 | −1.001273823 | −0.540249056 | −0.957890443 | −0.833137774 | III |
| 386 | HM-04 | J12 | hsa-miR-4794 | −0.850661248 | −0.66319225 | −0.982402839 | −0.832085446 | III |
| 387 | HM-04 | I1 | hsa-miR-3938 | −0.94699259 | −0.656688845 | −0.874594995 | −0.82675891 | III |
| 388 | HM-02 | L8 | hsa-miR-218-1* | −0.69352024 | −0.903349161 | −0.859189494 | −0.818686298 | III |
| 389 | HM-02 | O17 | hsa-miR-33a | −0.896622113 | −0.613545014 | −0.928980757 | −0.813049295 | III |
| 390 | HM-02 | F5 | hsa-miR-523 | −0.814820943 | −0.663829887 | −0.956897247 | −0.811849359 | III |
| 391 | HM-03 | E5 | hsa-miR-1257 | −0.713237487 | −0.822340669 | −0.897284046 | −0.810954067 | III |
| 392 | HM-05 | B4 | hsa-miR-4717-5p | −0.740245202 | −0.872539445 | −0.818834207 | −0.810539618 | III |

TABLE 2-continued

| Number | Plate | Well | miRNA | Robust Z-score Replicate 1 | Replicate 2 | Replicate 3 | Average Robust '-score | Rank |
|---|---|---|---|---|---|---|---|---|
| 393 | HM-02 | L20 | hsa-miR-920 | −0.882969106 | −0.647284635 | −0.892928652 | −0.807727464 | III |
| 394 | HM-03 | F20 | hsa-miR-3152 | −0.901923545 | −0.887326887 | −0.619947528 | −0.803065987 | III |
| 395 | HM-05 | H5 | hsa-miR-4536 | −0.445342203 | −1.004624922 | −0.93243386 | −0.794133662 | III |
| 396 | HM-02 | M2 | hsa-miR-7-2* | −0.411188922 | −0.939745119 | −1.022205477 | −0.791046506 | III |
| 397 | HM-03 | M4 | hsa-miR-2278 | −0.891774562 | −0.8890239 | −0.586002471 | −0.788933644 | III |
| 398 | HM-01 | G10 | hsa-miR-19b | −0.735221955 | −0.874775769 | −0.75565233 | −0.788550018 | III |
| 399 | HM-04 | J18 | hsa-miR-4778-3p | −0.849372479 | −0.641084558 | −0.871836879 | −0.787431305 | III |
| 400 | HM-03 | I19 | hsa-miR-1271 | −0.81932422 | −0.957936545 | −0.584299763 | −0.787186842 | III |
| 401 | HM-03 | B5 | hsa-miR-3180-5p | −0.845541115 | −0.843274642 | −0.669397636 | −0.786071131 | III |
| 402 | HM-02 | L19 | hsa-miR-126 | −0.883834375 | −0.665431966 | −0.808644388 | −0.785970243 | III |
| 403 | HM-03 | G20 | hsa-miR-675* | −0.971043187 | −0.809630326 | −0.571474401 | −0.784049305 | III |
| 404 | HM-04 | M10 | hsa-miR-4650-3p | −0.677473036 | −0.832074687 | −0.83723548 | −0.782261068 | III |
| 405 | HM-02 | M15 | hsa-let-7f-2* | −0.804177029 | −0.67013142 | −0.866435223 | −0.78024789 | III |
| 406 | HM-02 | H6 | hsa-miR-509-3p | −0.815506352 | −0.825941243 | −0.689130708 | −0.776859435 | III |
| 407 | HM-05 | I2 | hsa-miR-4738-3p | −0.866372248 | −0.636928806 | −0.82682818 | −0.776709744 | III |
| 408 | HM-05 | M14 | hsa-miR-4668-5p | −0.80085335 | −0.813488205 | −0.706002414 | −0.77344799 | III |
| 409 | HM-04 | P14 | hsa-miR-4468 | −0.509761685 | −0.836185446 | −0.964878607 | −0.770275559 | III |
| 410 | HM-03 | G6 | hsa-miR-1911* | −1.283299178 | −0.171406022 | −0.846044673 | −0.766916624 | III |
| 411 | HM-01 | E8 | hsa-miR-199b-5p | −0.579792329 | −0.864530076 | −0.846791134 | −0.763704513 | III |
| 412 | HM-04 | L14 | hsa-miR-4762-3p | −0.568540987 | −0.801951317 | −0.910074028 | −0.760188777 | III |
| 413 | HM-05 | F11 | hsa-miR-4514 | −1.019445149 | −0.848900917 | −0.397932635 | −0.755426234 | III |
| 414 | HM-01 | A6 | hsa-miR-96 | −1.087817095 | −0.125749438 | −1.038025367 | −0.750530633 | III |
| 415 | HM-01 | O18 | hsa-miR-15b | −0.91870351 | −0.949234954 | −0.337854066 | −0.735264177 | III |
| 416 | HM-01 | K10 | hsa-miR-27b | −0.857838344 | −1.072097448 | −0.257445899 | −0.72912723 | III |
| 417 | HM-03 | D21 | hsa-miR-378c | −0.88517595 | −0.433705161 | −0.802056044 | −0.706979052 | III |
| 418 | HM-02 | M5 | hsa-miR-16-2* | −0.384936655 | −0.87218882 | −0.851759584 | −0.702961686 | III |
| 419 | HM-01 | I15 | hsa-miR-15a | −0.23503617 | −0.84052635 | −0.862107521 | −6.645890013 | III |
| 420 | HM-01 | J2 | hsa-miR-630 | −2.654612783 | −2.271200847 | 3.088938576 | −0.612291685 | III |
| 421 | HM-05 | G20 | hsa-miR-4510 | −0.950936475 | −1.10397215 | 0.347210578 | −0.569232682 | III |
| 422 | HM-02 | H22 | hsa-miR-542-5p | −1.042106852 | −0.958861061 | 0.29377745 | −0.569063488 | III |
| 423 | HM-03 | F5 | hsa-miR-4269 | −2.266711413 | 3.019057483 | −1.983176641 | −0.410276857 | III |

What is claimed is:

1. A pharmaceutical composition comprising (i) an oligonucleotide, wherein said oligonucleotide is capable of decreasing the level and/or activity of miR-148a and comprises a sequence complimentary to nucleotides 2-8 at the 5' end of the mature miRNA sequence of miR-148a, and (ii) one or more active substances selected from the group consisting of statins, niacin, bile-acid resins, fibric acid derivatives, cholesterol absorption inhibitors, and lipid-lowering drugs.

2. The pharmaceutical composition of claim 1, wherein the mature miRNA sequence of miR-148a is 5'-UCAGUG-CACUACAGAACUUUGU-3' (SEQ ID NOS: 6, 60-61).

3. The pharmaceutical composition of claim 1, wherein said oligonucleotide comprises the sequence 5'-(T/U)GCAC(T/U)G-3' (SEQ ID NO: 117).

4. The pharmaceutical composition of claim 1, wherein said oligonucleotide is a modified oligonucleotide.

5. A pharmaceutical composition comprising
  (i) a first oligonucleotide, wherein said first oligonucleotide is capable of decreasing the level and/or activity of miR-148a and comprises a sequence complimentary to nucleotides 2-8 at the 5' end of the mature miRNA sequence of miR-148a,
  (ii) a second oligonucleotide, wherein said second oligonucleotide is capable of decreasing the level and/or activity of miR-27b, and/or a third oligonucleotide, wherein said third oligonucleotide is capable of decreasing the level and/or activity of miR-33, and
  (iii) a pharmaceutically acceptable carrier or excipient.

6. The pharmaceutical composition of claim 5, wherein the mature miRNA sequence of miR-148a is 5'-UCAGUG-CACUACAGAACUUUGU-3' (SEQ ID NOS: 6, 60-61).

7. The pharmaceutical composition of claim 5, wherein said first oligonucleotide comprises the sequence 5'-(T/U)GCAC(T/U)G-3' (SEQ ID NO: 117).

8. The pharmaceutical composition of claim 5, wherein said first oligonucleotide and/or said second oligonucleotide and/or said third oligonucleotide is a modified oligonucleotide.

9. The pharmaceutical composition of claim 5, wherein said second oligonucleotide comprises a sequence complimentary to nucleotides 2-8 at the 5' end of the mature miRNA sequence of miR-27b.

10. The pharmaceutical composition of claim 9, wherein the mature miRNA sequence of miR-27b is 5'-UUCACA-GUGGCUAAGUUCUGC-3' (SEQ ID NOS: 1, 58-59).

11. The pharmaceutical composition of claim 5, wherein said second oligonucleotide comprises the sequence 5'-AC(T/U)G(T/U)GA-3' (SEQ ID NO: 114).

* * * * *

SEQUENCE LISTING

<160> NUMBER OF SEQ ID NOS: 127

<210> SEQ ID NO 1
<211> LENGTH: 21
<212> TYPE: RNA
<213> ORGANISM: Homo sapiens
<220> FEATURE:
<223> OTHER INFORMATION: miR-27b

<400> SEQUENCE: 1
uucacagugg cuaaguucug c                                          21

<210> SEQ ID NO 2
<211> LENGTH: 97
<212> TYPE: RNA
<213> ORGANISM: Homo sapiens
<220> FEATURE:
<223> OTHER INFORMATION: miR-27b

<400> SEQUENCE: 2
accucucuaa caaggugcag agcuuagcug auuggugaac agugauuggu uuccgcuuug     60
uucacagugg cuaaguucug caccugaaga gaaggug                             97

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ABCA1 3' UTR (nt 3099-3119) - miR-148a target 1

<400> SEQUENCE: 3 auggaucua uuuuugcacu gg                                              22

<210> SEQ ID NO 4
<211> LENGTH: 18
<212> TYPE: RNA
<213> ORGANISM: Homo sapiens
<220> FEATURE:
<223> OTHER INFORMATION: ABCA1 3' UTR - miR-148a target 1

<400> SEQUENCE: 4 cuauuuugc acuggaau                                                   18

<210> SEQ ID NO 5
<211> LENGTH: 18
<212> TYPE: RNA
<213> ORGANISM: Pan troglodytes
<220> FEATURE:
<223> OTHER INFORMATION: ABCA1 3' UTR - miR-148a target 1

<400> SEQUENCE: 5 cuauuuugc acuggaau                                                   18

<210> SEQ ID NO 6
<211> LENGTH: 22
<212> TYPE: RNA
<213> ORGANISM: Homo sapiens
<220> FEATURE:
<223> OTHER INFORMATION: miR-148a

<400> SEQUENCE: 6
ucagugcacu acagaacuuu gu                                             22

<210> SEQ ID NO 7
<211> LENGTH: 68
<212> TYPE: RNA
<213> ORGANISM: Homo sapiens
<220> FEATURE:
<223> OTHER INFORMATION: miR-148a

<400> SEQUENCE: 7
gaggcaaagu ucugagacac uccgacucug aguaugauag aagucagugc acuacagaac    60
uuugucuc                                                             68

<210> SEQ ID NO 8
<211> LENGTH: 18
<212> TYPE: RNA
<213> ORGANISM: Mus musculus
<220> FEATURE:
<223> OTHER INFORMATION: ABCA1 3' UTR - miR-148a target 1

<400> SEQUENCE: 8 cuauuuugc acuggaau                                                   18

<210> SEQ ID NO 9
<211> LENGTH: 18
<212> TYPE: RNA
<213> ORGANISM: Rattus norvegicus
<220> FEATURE:
<223> OTHER INFORMATION: ABCA1 3' UTR - miR-148a target 1

<400> SEQUENCE: 9 cuauuuugc acuggaau                                                   18

```
<210> SEQ ID NO 10
<211> LENGTH: 18
<212> TYPE: RNA
<213> ORGANISM: Oryctolagus cuniculus
<220> FEATURE:
<223> OTHER INFORMATION: ABCA1 3' UTR - miR-148a target 1

<400> SEQUENCE: 10
cuauuuuugc acuggaau                                                 18

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Homo sapiens GAPDH primer sequence

<400> SEQUENCE: 11
ttgattttgg agggatctcg                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Homo sapiens GAPDH primer sequence

<400> SEQUENCE: 12
caatgacccc ttcattgacc                                               20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Homo sapiens LDLR primer sequence

<400> SEQUENCE: 13
tgatgggttc atctgaccag t                                             21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Homo sapiens LDLR primer sequence

<400> SEQUENCE: 14
agttggctgc gttaatgtga c                                             21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued

```
                          primer
<220> FEATURE:
<223> OTHER INFORMATION: Homo sapiens LDLRAP1 primer sequence

<400> SEQUENCE: 15
atcgtggcta cagctaaggc                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Homo sapiens LDLRAP1 primer sequence

<400> SEQUENCE: 16
caaacacctt gtcgtgcatc                                              20

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Homo sapiens ABCA1 primer sequence

<400> SEQUENCE: 17
tgtcctcata ccagttgaga gac                                          23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Homo sapiens ABCA1 primer sequence

<400> SEQUENCE: 18
ggtgatgttt ctgaccaatg tga                                          23

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Mus musculus LDLR primer sequence

<400> SEQUENCE: 19
ggtactggca accaccattg gg                                           22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Mus musculus LDLR primer sequence
```

```
<400> SEQUENCE: 20
gccaatcgac tcacgggttc ag                                                22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Mus musculus 18S primer sequence

<400> SEQUENCE: 21
ttccgataac gaacgagact ct                                                22

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Mus musculus 18S primer sequence

<400> SEQUENCE: 22
tggctgaacg ccacttgtc                                                    19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Homo sapiens pri-miR-27b primer sequence

<400> SEQUENCE: 23
gttcctggca tgctgatttg                                                   20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Homo sapiens pri-miR-27b primer sequence

<400> SEQUENCE: 24
ctaagctctg caccttgtta ga                                                22

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Mus musculus pri-miR-27b primer sequence

<400> SEQUENCE: 25
gttcctggca tgctgatttg                                                   20
```

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Mus musculus pri-miR-27b primer sequence

<400> SEQUENCE: 26
ctaagctctg caccttgtta ga                                            22

<210> SEQ ID NO 27
<211> LENGTH: 21
<212> TYPE: RNA
<213> ORGANISM: Homo sapiens
<220> FEATURE:
<223> OTHER INFORMATION: miR-23b

<400> SEQUENCE: 27
aucacauugc cagggauuac c                                             21

<210> SEQ ID NO 28
<211> LENGTH: 21
<212> TYPE: DNA
<213> ORGANISM: Homo sapiens
<220> FEATURE:
<223> OTHER INFORMATION: miR-23b genomic sequence

<400> SEQUENCE: 28
atcacattgc cagggattac c                                             21

<210> SEQ ID NO 29
<211> LENGTH: 21
<212> TYPE: DNA
<213> ORGANISM: Homo sapiens
<220> FEATURE:
<223> OTHER INFORMATION: miR-27b genomic sequence

<400> SEQUENCE: 29
ttcacagtgg ctaagttctg c                                             21

<210> SEQ ID NO 30
<211> LENGTH: 22
<212> TYPE: DNA
<213> ORGANISM: Homo sapiens
<220> FEATURE:
<223> OTHER INFORMATION: miR-148a genomic sequence

<400> SEQUENCE: 30
tcagtgcact acagaacttt gt                                            22

<210> SEQ ID NO 31
<211> LENGTH: 22
<212> TYPE: RNA
<213> ORGANISM: Homo sapiens
<220> FEATURE:
<223> OTHER INFORMATION: miR-24-1

<400> SEQUENCE: 31
uggcucaguu cagcaggaac ag                                            22

<210> SEQ ID NO 32
<211> LENGTH: 22
<212> TYPE: DNA

```
<213> ORGANISM: Homo sapiens
<220> FEATURE:
<223> OTHER INFORMATION: miR-24-1 genomic sequence

<400> SEQUENCE: 32
tggctcagtt cagcaggaac ag                                          22

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: antisense to miR-148a

<400> SEQUENCE: 33
acaaagttct gtagtgcac                                              19

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: antisense to miR-27b

<400> SEQUENCE: 34
agaacttagc cactgtga                                               18

<210> SEQ ID NO 35
<211> LENGTH: 16
<212> TYPE: DNA
<213> ORGANISM: Homo sapiens
<220> FEATURE:
<223> OTHER INFORMATION: LDLR 3' UTR - (nt 2469-2484) miR-27b target

<400> SEQUENCE: 35
cttactgtga tcaatt                                                 16

<210> SEQ ID NO 36
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LDLR 3' UTR (nt 2469-2484) with point mutations
      (PM1)

<400> SEQUENCE: 36
ctttgtgtga tcaatt                                                 16

<210> SEQ ID NO 37
<211> LENGTH: 11
<212> TYPE: DNA
<213> ORGANISM: Homo sapiens
<220> FEATURE:
<223> OTHER INFORMATION: LDLRAP1 3' UTR (nt 346-356) - miR-27b target

<400> SEQUENCE: 37
aggactgtga c                                                      11
```

```
<210> SEQ ID NO 38
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LDLRAP1 3' UTR (nt 346-356) with point
      mutations (PM1)

<400> SEQUENCE: 38
aggacgttga c                                                          11

<210> SEQ ID NO 39
<211> LENGTH: 11
<212> TYPE: DNA
<213> ORGANISM: Homo sapiens
<220> FEATURE:
<223> OTHER INFORMATION: LDLRAP1 3' UTR (nt 1317-1328) - miR-27b target

<400> SEQUENCE: 39
gacactgtga c                                                          11

<210> SEQ ID NO 40
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LDLRAP1 3' UTR (nt 1317-1328) with point
      mutations (PM2)

<400> SEQUENCE: 40
gacacgttga c                                                          11

<210> SEQ ID NO 41
<211> LENGTH: 12
<212> TYPE: DNA
<213> ORGANISM: Homo sapiens
<220> FEATURE:
<223> OTHER INFORMATION: ABCA1 3' UTR (nt 2282-2293) - miR-27b target

<400> SEQUENCE: 41
ggcactgtga ac                                                         12

<210> SEQ ID NO 42
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ABCA1 3' UTR (nt 2282-2293) with point
      mutations (PM1)

<400> SEQUENCE: 42
ggctgtgtga ac                                                         12

<210> SEQ ID NO 43
<211> LENGTH: 12
<212> TYPE: DNA
<213> ORGANISM: Homo sapiens
<220> FEATURE:
<223> OTHER INFORMATION: ABCA1 3' UTR (nt 2590-2601) - miR-27b target
```

```
<400> SEQUENCE: 43
acaactgtga at                                                        12

<210> SEQ ID NO 44
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ABCA1 3' UTR (nt 2590-2601) with point
      mutations (PM2)

<400> SEQUENCE: 44
acatgtgtga at                                                        12

<210> SEQ ID NO 45
<211> LENGTH: 12
<212> TYPE: DNA
<213> ORGANISM: Homo sapiens
<220> FEATURE:
<223> OTHER INFORMATION: LDLR 3' UTR (nt 869-880) - miR-148a target

<400> SEQUENCE: 45
ttttgcactg tt                                                        12

<210> SEQ ID NO 46
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LDLR 3' UTR (nt 869-880) with point mutations
      (PM1)

<400> SEQUENCE: 46
ttttgctgtg tt                                                        12

<210> SEQ ID NO 47
<211> LENGTH: 12
<212> TYPE: DNA
<213> ORGANISM: Homo sapiens
<220> FEATURE:
<223> OTHER INFORMATION: LDLR 3' UTR (nt 1971-1979) - miR-148a target

<400> SEQUENCE: 47
tgttgcactg at                                                        12

<210> SEQ ID NO 48
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LDLR 3' UTR (nt 1971-1979) with point mutations
      (PM2)

<400> SEQUENCE: 48
tgttgctgtg at                                                        12

<210> SEQ ID NO 49
<211> LENGTH: 11
```

```
<212> TYPE: DNA
<213> ORGANISM: Homo sapiens
<220> FEATURE:
<223> OTHER INFORMATION: ABCA1 3' UTR - (nt 3109-3119) miR-148a target

<400> SEQUENCE: 49
ttttgcactg g                                                          11

<210> SEQ ID NO 50
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ABCA1 3' UTR - (nt 3109-3119) with point
      mutations (PM1)

<400> SEQUENCE: 50
ttttgctcag g                                                          11

<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: antisense control

<400> SEQUENCE: 51
acgtctatac gccca                                                      15

<210> SEQ ID NO 52
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: antisense to miR-148a

<400> SEQUENCE: 52
ttctgtagtg cactg                                                      15

<210> SEQ ID NO 53
<211> LENGTH: 15
<212> TYPE: DNA
<213> ORGANISM: Mus musculus
<220> FEATURE:
<223> OTHER INFORMATION: miR-148a target sequence for antisense

<400> SEQUENCE: 53
cagtgcacta cagaa                                                      15

<210> SEQ ID NO 54
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: antisense to miR-27b

<400> SEQUENCE: 54
```

```
aacttagcca ctgtga                                                      16

<210> SEQ ID NO 55
<211> LENGTH: 16
<212> TYPE: DNA
<213> ORGANISM: Mus musculus
<220> FEATURE:
<223> OTHER INFORMATION: miR-27b target sequence for antisense

<400> SEQUENCE: 55
tcacagtggc taagtt                                                      16

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: probe for mature miR-148a

<400> SEQUENCE: 56
acaaagttct gtagtgcact ga                                               22

<210> SEQ ID NO 57
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Probe for 5s rRNA

<400> SEQUENCE: 57
caggcccgac cctgcttagc ttccgagaga tcagacgaga t                          41

<210> SEQ ID NO 58
<211> LENGTH: 21
<212> TYPE: RNA
<213> ORGANISM: Macaca mulatta
<220> FEATURE:
<223> OTHER INFORMATION: miR-27b

<400> SEQUENCE: 58
uucacagugg cuaaguucug c                                                21

<210> SEQ ID NO 59
<211> LENGTH: 21
<212> TYPE: RNA
<213> ORGANISM: Mus musculus
<220> FEATURE:
<223> OTHER INFORMATION: miR-27b

<400> SEQUENCE: 59
uucacagugg cuaaguucug c                                                21

<210> SEQ ID NO 60
<211> LENGTH: 22
<212> TYPE: RNA
<213> ORGANISM: Macaca mulatta
<220> FEATURE:
<223> OTHER INFORMATION: miR-148a

<400> SEQUENCE: 60
```
ucagugcacu acagaacuuu gu                                                    22

<210> SEQ ID NO 61
<211> LENGTH: 22
<212> TYPE: RNA
<213> ORGANISM: Mus musculus
<220> FEATURE:
<223> OTHER INFORMATION: miR-148a

<400> SEQUENCE: 61
ucagugcacu acagaacuuu gu                                                    22

<210> SEQ ID NO 62
<211> LENGTH: 21
<212> TYPE: RNA
<213> ORGANISM: Macaca mulatta
<220> FEATURE:
<223> OTHER INFORMATION: miR-23b

<400> SEQUENCE: 62
aucacauugc cagggauuac c                                                     21

<210> SEQ ID NO 63
<211> LENGTH: 21
<212> TYPE: RNA
<213> ORGANISM: Mus musculus
<220> FEATURE:
<223> OTHER INFORMATION: miR-23b

<400> SEQUENCE: 63
aucacauugc cagggauuac c                                                     21

<210> SEQ ID NO 64
<211> LENGTH: 22
<212> TYPE: RNA
<213> ORGANISM: Macaca mulatta
<220> FEATURE:
<223> OTHER INFORMATION: miR-24-1

<400> SEQUENCE: 64
uggcucaguu cagcaggaac ag                                                    22

<210> SEQ ID NO 65
<211> LENGTH: 22
<212> TYPE: RNA
<213> ORGANISM: Mus musculus
<220> FEATURE:
<223> OTHER INFORMATION: miR-24-1

<400> SEQUENCE: 65
uggcucaguu cagcaggaac ag                                                    22

<210> SEQ ID NO 66
<211> LENGTH: 21
<212> TYPE: DNA
<213> ORGANISM: Macaca mulatta
<220> FEATURE:
<223> OTHER INFORMATION: miR-23b genomic sequence

<400> SEQUENCE: 66
atcacattgc cagggattac c                                                     21

<210> SEQ ID NO 67
<211> LENGTH: 21
<212> TYPE: DNA
<213> ORGANISM: Mus musculus

```
<220> FEATURE:
<223> OTHER INFORMATION: miR-23b genomic sequence

<400> SEQUENCE: 67
atcacattgc cagggattac c                                              21

<210> SEQ ID NO 68
<211> LENGTH: 21
<212> TYPE: DNA
<213> ORGANISM: Macaca mulatta
<220> FEATURE:
<223> OTHER INFORMATION: miR-27b genomic sequence

<400> SEQUENCE: 68
ttcacagtgg ctaagttctg c                                              21

<210> SEQ ID NO 69
<211> LENGTH: 21
<212> TYPE: DNA
<213> ORGANISM: Mus musculus
<220> FEATURE:
<223> OTHER INFORMATION: miR-27b genomic sequence

<400> SEQUENCE: 69
ttcacagtgg ctaagttctg c                                              21

<210> SEQ ID NO 70
<211> LENGTH: 22
<212> TYPE: DNA
<213> ORGANISM: Macaca mulatta
<220> FEATURE:
<223> OTHER INFORMATION: miR-24-1 genomic sequence

<400> SEQUENCE: 70
tggctcagtt cagcaggaac ag                                             22

<210> SEQ ID NO 71
<211> LENGTH: 22
<212> TYPE: DNA
<213> ORGANISM: Mus musculus
<220> FEATURE:
<223> OTHER INFORMATION: miR-24-1 genomic sequence

<400> SEQUENCE: 71
tggctcagtt cagcaggaac ag                                             22

<210> SEQ ID NO 72
<211> LENGTH: 22
<212> TYPE: DNA
<213> ORGANISM: Macaca mulatta
<220> FEATURE:
<223> OTHER INFORMATION: miR-148a genomic sequence

<400> SEQUENCE: 72
tcagtgcact acagaacttt gt                                             22

<210> SEQ ID NO 73
<211> LENGTH: 22
<212> TYPE: DNA
<213> ORGANISM: Mus musculus
<220> FEATURE:
<223> OTHER INFORMATION: miR-148a genomic sequence

<400> SEQUENCE: 73
tcagtgcact acagaacttt gt                                             22
```

<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: LDLR 3' UTR (nt 2459-2479) - miR-27b target 1

<400> SEQUENCE: 74
gccugaaugu cuuacuguga u                                              21

<210> SEQ ID NO 75
<211> LENGTH: 17
<212> TYPE: RNA
<213> ORGANISM: Homo sapiens
<220> FEATURE:
<223> OTHER INFORMATION: LDLR 3' UTR - miR-27b target 1

<400> SEQUENCE: 75
ugucuuacug ugaucaa                                                   17

<210> SEQ ID NO 76
<211> LENGTH: 17
<212> TYPE: RNA
<213> ORGANISM: Pan troglodytes
<220> FEATURE:
<223> OTHER INFORMATION: LDLR 3' UTR - miR-27b target 1

<400> SEQUENCE: 76
ugucuuacug ugaucaa                                                   17

<210> SEQ ID NO 77
<211> LENGTH: 17
<212> TYPE: RNA
<213> ORGANISM: Mus musculus
<220> FEATURE:
<223> OTHER INFORMATION: LDLR 3' UTR - miR-27b target 1

<400> SEQUENCE: 77
uaucauacug ugaugga                                                   17

<210> SEQ ID NO 78
<211> LENGTH: 17
<212> TYPE: RNA
<213> ORGANISM: Rattus norvegicus
<220> FEATURE:
<223> OTHER INFORMATION: LDLR 3' UTR - miR-27b target 1

<400> SEQUENCE: 78
uaucauacug ugaugga                                                   17

<210> SEQ ID NO 79
<211> LENGTH: 17
<212> TYPE: RNA
<213> ORGANISM: Oryctolagus cuniculus
<220> FEATURE:
<223> OTHER INFORMATION: LDLR 3' UTR - miR-27b target 1

<400> SEQUENCE: 79
ggggucccug ugguuga                                                   17

<210> SEQ ID NO 80
<211> LENGTH: 21
<212> TYPE: RNA

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: ABCA1 3' UTR (nt 2273-2293) - miR-27b target 1

<400> SEQUENCE: 80
aaaaucaaaa ggcacuguga a                                             21

<210> SEQ ID NO 81
<211> LENGTH: 15
<212> TYPE: RNA
<213> ORGANISM: Homo sapiens
<220> FEATURE:
<223> OTHER INFORMATION: ABCA1 3' UTR - miR-27b target 2

<400> SEQUENCE: 81
aaaaggcacu gugaa                                                    15

<210> SEQ ID NO 82
<211> LENGTH: 15
<212> TYPE: RNA
<213> ORGANISM: Pan troglodytes
<220> FEATURE:
<223> OTHER INFORMATION: ABCA1 3' UTR - miR-27b target 1

<400> SEQUENCE: 82
aaaaggcacu gugaa                                                    15

<210> SEQ ID NO 83
<211> LENGTH: 13
<212> TYPE: RNA
<213> ORGANISM: Mus musculus
<220> FEATURE:
<223> OTHER INFORMATION: ABCA1 3' UTR - miR-27b target 1

<400> SEQUENCE: 83
caaaaguaag gca                                                      13

<210> SEQ ID NO 84
<211> LENGTH: 13
<212> TYPE: RNA
<213> ORGANISM: Rattus norvegicus
<220> FEATURE:
<223> OTHER INFORMATION: ABCA1 3' UTR - miR-27b target 1

<400> SEQUENCE: 84
caaaaauaag gca                                                      13

<210> SEQ ID NO 85
<211> LENGTH: 15
<212> TYPE: RNA
<213> ORGANISM: Oryctolagus cuniculus
<220> FEATURE:
<223> OTHER INFORMATION: ABCA1 3' UTR - miR-27b target 1

<400> SEQUENCE: 85
aaagggcacu gugaa                                                    15

<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: ABCA1 3' UTR (nt 2581-2601) - miR-27b target 2

<400> SEQUENCE: 86
aaacuuauua acaacuguga a                                             21

<210> SEQ ID NO 87
<211> LENGTH: 16
<212> TYPE: RNA
<213> ORGANISM: Homo sapiens
<220> FEATURE:
<223> OTHER INFORMATION: ABCA1 3' UTR - miR-27b target 2

<400> SEQUENCE: 87
aacaacugug aauaug                                                   16

<210> SEQ ID NO 88
<211> LENGTH: 16
<212> TYPE: RNA
<213> ORGANISM: Pan troglodytes
<220> FEATURE:
<223> OTHER INFORMATION: ABCA1 3' UTR - miR-27b target 2

<400> SEQUENCE: 88
aacaacugug aauaug                                                   16

<210> SEQ ID NO 89
<211> LENGTH: 13
<212> TYPE: RNA
<213> ORGANISM: Mus musculus
<220> FEATURE:
<223> OTHER INFORMATION: ABCA1 3' UTR - miR-27b target 2

<400> SEQUENCE: 89
aacugugaau aug                                                      13

<210> SEQ ID NO 90
<211> LENGTH: 13
<212> TYPE: RNA
<213> ORGANISM: Rattus norvegicus
<220> FEATURE:
<223> OTHER INFORMATION: ABCA1 3' UTR - miR-27b target 2

<400> SEQUENCE: 90
aacugugaau aug                                                      13

<210> SEQ ID NO 91
<211> LENGTH: 12
<212> TYPE: RNA
<213> ORGANISM: Oryctolagus cuniculus
<220> FEATURE:
<223> OTHER INFORMATION: ABCA1 3' UTR - miR-27b target 2

<400> SEQUENCE: 91
acugugaaga ug                                                       12

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LDLRAP1 3' UTR (nt 2581-2601) - miR-27b
      target 1
```

```
<400> SEQUENCE: 92
uguggguauc aggacuguga c                                              21

<210> SEQ ID NO 93
<211> LENGTH: 17
<212> TYPE: RNA
<213> ORGANISM: Homo sapiens
<220> FEATURE:
<223> OTHER INFORMATION: LDLRAP 1 3' UTR - miR-27b target 1

<400> SEQUENCE: 93
aucaggacug ugaccaa                                                   17

<210> SEQ ID NO 94
<211> LENGTH: 17
<212> TYPE: RNA
<213> ORGANISM: Pan troglodytes
<220> FEATURE:
<223> OTHER INFORMATION: LDLRAP 1 3' UTR - miR-27b target 1

<400> SEQUENCE: 94
aucaggacug ugaccaa                                                   17

<210> SEQ ID NO 95
<211> LENGTH: 17
<212> TYPE: RNA
<213> ORGANISM: Mus musculus
<220> FEATURE:
<223> OTHER INFORMATION: LDLRAP 1 3' UTR - miR-27b target 1

<400> SEQUENCE: 95
gucaggacaa ugaccaa                                                   17

<210> SEQ ID NO 96
<211> LENGTH: 17
<212> TYPE: RNA
<213> ORGANISM: Rattus norvegicus
<220> FEATURE:
<223> OTHER INFORMATION: LDLRAP 1 3' UTR - miR-27b target 1

<400> SEQUENCE: 96
guccagacaa ugaccaa                                                   17

<210> SEQ ID NO 97
<211> LENGTH: 18
<212> TYPE: RNA
<213> ORGANISM: Oryctolagus cuniculus
<220> FEATURE:
<223> OTHER INFORMATION: LDLRAP 1 3' UTR - miR-27b target 1

<400> SEQUENCE: 97
gcucaggacg gcgaccaa                                                  18

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LDLRAP1 3' UTR (nt 1308-1328) - miR-27b
      target 2

<400> SEQUENCE: 98
ucucuuugcu gacacuguga c                                              21
```

```
<210> SEQ ID NO 99
<211> LENGTH: 14
<212> TYPE: RNA
<213> ORGANISM: Homo sapiens
<220> FEATURE:
<223> OTHER INFORMATION: LDLRAP 1 3' UTR - miR-27b target 2

<400> SEQUENCE: 99
ugcugacacu guga                                                      14

<210> SEQ ID NO 100
<211> LENGTH: 14
<212> TYPE: RNA
<213> ORGANISM: Pan troglodytes
<220> FEATURE:
<223> OTHER INFORMATION: LDLRAP 1 3' UTR - miR-27b target 2

<400> SEQUENCE: 100
ugcugacacu guga                                                      14

<210> SEQ ID NO 101
<211> LENGTH: 17
<212> TYPE: RNA
<213> ORGANISM: Mus musculus
<220> FEATURE:
<223> OTHER INFORMATION: LDLRAP 1 3' UTR - miR-27b target 2

<400> SEQUENCE: 101
uucugaccug cagccgu                                                   17

<210> SEQ ID NO 102
<211> LENGTH: 17
<212> TYPE: RNA
<213> ORGANISM: Rattus norvegicus
<220> FEATURE:
<223> OTHER INFORMATION: LDLRAP 1 3' UTR - miR-27b target 2

<400> SEQUENCE: 102
uccugaccug cagccuu                                                   17

<210> SEQ ID NO 103
<211> LENGTH: 14
<212> TYPE: RNA
<213> ORGANISM: Oryctolagus cuniculus
<220> FEATURE:
<223> OTHER INFORMATION: LDLRAP 1 3' UTR - miR-27b target 2

<400> SEQUENCE: 103
ucccagcgcc gugg                                                      14

<210> SEQ ID NO 104
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LDLR 3' UTR (nt 859-879) - miR-148a target 1

<400> SEQUENCE: 104
uuguguuauu auuuugcacu gu                                             22

<210> SEQ ID NO 105
<211> LENGTH: 18
```

```
<212> TYPE: RNA
<213> ORGANISM: Homo sapiens
<220> FEATURE:
<223> OTHER INFORMATION: LDLR 3' UTR - miR-148a target 1

<400> SEQUENCE: 105
auuauuuugc acuguuuu                                                     18

<210> SEQ ID NO 106
<211> LENGTH: 18
<212> TYPE: RNA
<213> ORGANISM: Pan troglodytes
<220> FEATURE:
<223> OTHER INFORMATION: LDLR 3' UTR - miR-148a target 1

<400> SEQUENCE: 106
auuauuuugc acuguuuu                                                     18

<210> SEQ ID NO 107
<211> LENGTH: 17
<212> TYPE: RNA
<213> ORGANISM: Mus musculus
<220> FEATURE:
<223> OTHER INFORMATION: LDLR 3' UTR - miR-148a target 1

<400> SEQUENCE: 107
ccuagguugc acugacc                                                      17

<210> SEQ ID NO 108
<211> LENGTH: 18
<212> TYPE: RNA
<213> ORGANISM: Rattus norvegicus
<220> FEATURE:
<223> OTHER INFORMATION: LDLR 3' UTR - miR-148a target 1

<400> SEQUENCE: 108
ccuagguugc acuguuug                                                     18

<210> SEQ ID NO 109
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LDLR 3' UTR (nt 1959-1979) - miR-148a target 2

<400> SEQUENCE: 109
ccuguuuacu guugcacuga                                                   20

<210> SEQ ID NO 110
<211> LENGTH: 19
<212> TYPE: RNA
<213> ORGANISM: Homo sapiens
<220> FEATURE:
<223> OTHER INFORMATION: LDLR 3' UTR - miR-148a target 2

<400> SEQUENCE: 110
uuacuguugc acugauguc                                                    19

<210> SEQ ID NO 111
<211> LENGTH: 19
<212> TYPE: RNA
<213> ORGANISM: Pan troglodytes
<220> FEATURE:
<223> OTHER INFORMATION: LDLR 3' UTR - miR-148a target 2
```

```
<400> SEQUENCE: 111
uuacuguugc acugauguc                                                    19

<210> SEQ ID NO 112
<211> LENGTH: 15
<212> TYPE: RNA
<213> ORGANISM: Mus musculus
<220> FEATURE:
<223> OTHER INFORMATION: LDLR 3' UTR - miR-148a target 2

<400> SEQUENCE: 112
ugucacaugg guaac                                                        15

<210> SEQ ID NO 113
<211> LENGTH: 15
<212> TYPE: RNA
<213> ORGANISM: Rattus norvegicus
<220> FEATURE:
<223> OTHER INFORMATION: LDLR 3' UTR - miR-148a target 2

<400> SEQUENCE: 113
ugucacacgg gugac                                                        15

<210> SEQ ID NO 114
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: antisense to miR-27b (nt 2-8)
<220> FEATURE:
<221> NAME/KEY: modified_base
<222> LOCATION: (3)..(3)
<223> OTHER INFORMATION: u or t
<220> FEATURE:
<221> NAME/KEY: modified_base
<222> LOCATION: (5)..(5)
<223> OTHER INFORMATION: u or t

<400> SEQUENCE: 114 acngnga                                                                 7

<210> SEQ ID NO 115
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: antisense to miR-27b (nt 2-8)

<400> SEQUENCE: 115 actgtga                                                                 7

<210> SEQ ID NO 116
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
```

```
<223> OTHER INFORMATION: antisense to miR-27b (nt 2-8)

<400> SEQUENCE: 116 acuguga                                                                    7

<210> SEQ ID NO 117
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: antisense to miR-148a (nt 2-8)
<220> FEATURE:
<221> NAME/KEY: modified_base
<222> LOCATION: (1)..(1)
<223> OTHER INFORMATION: u or t
<220> FEATURE:
<221> NAME/KEY: modified_base
<222> LOCATION: (6)..(6)
<223> OTHER INFORMATION: u or t

<400> SEQUENCE: 117 ngcacng                                                                    7

<210> SEQ ID NO 118
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: antisense to miR-148a (nt 2-8)

<400> SEQUENCE: 118 tgcactg                                                                    7

<210> SEQ ID NO 119
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: antisense to miR-148a (nt 2-8)

<400> SEQUENCE: 119 ugcacug                                                                    7

<210> SEQ ID NO 120
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
ggtttggaga tggttataca atagttgt                                            28

<210> SEQ ID NO 121
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 121
cccggaaacg caagtcc                                                    17

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
ggagccatgg attgcacatt                                                 20

<210> SEQ ID NO 123
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
acaaagttgc tctgaaaaca aatca                                           25

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
ggaggtggtg atagccggta t                                               21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
tgggtaatcc atagagccca g                                               21

<210> SEQ ID NO 126
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
tgatggcaga caataactcc                                                 20

<210> SEQ ID NO 127
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 127
aaagtgcttt cccatcttcc                                                    20
```